United States Patent
Li

(10) Patent No.: US 10,173,074 B2
(45) Date of Patent: Jan. 8, 2019

(54) CANCER STEM CELL VACCINATION AND TREATMENT

(71) Applicant: The Regents of the University of Michigan, Ann Arbor, MI (US)

(72) Inventor: Qiao Li, Ann Arbor, MI (US)

(73) Assignee: The Regents of The University of Michigan, Ann Harbor, MI (US)

( * ) Notice: Subject to any disclaimer, the term of this patent is extended or adjusted under 35 U.S.C. 154(b) by 71 days.

(21) Appl. No.: 14/437,064

(22) PCT Filed: Oct. 24, 2013

(86) PCT No.: PCT/US2013/066578
§ 371 (c)(1),
(2) Date: Apr. 20, 2015

(87) PCT Pub. No.: WO2014/066615
PCT Pub. Date: May 1, 2014

(65) Prior Publication Data
US 2015/0265848 A1    Sep. 24, 2015

Related U.S. Application Data

(60) Provisional application No. 61/717,902, filed on Oct. 24, 2012.

(51) Int. Cl.
*A61K 51/00*      (2006.01)
*A61N 5/10*       (2006.01)
(Continued)

(52) U.S. Cl.
CPC ........ *A61N 5/1001* (2013.01); *A61K 39/0011* (2013.01); *A61K 45/06* (2013.01);
(Continued)

(58) Field of Classification Search
CPC ........ A61K 2039/505; A61K 47/48569; A61K 47/48561; A61K 39/39558;
(Continued)

(56) References Cited

FOREIGN PATENT DOCUMENTS

WO    WO 0172341 A2 * 10/2001    ......... A61K 31/7048
WO    WO 2008/039874     4/2008
(Continued)

OTHER PUBLICATIONS

Kim et al. 'ALDH Activity Selectively Defines an Enhanced Tumor-Initiating Cell Population Relative to CD133 Expression in Human Pancreatic Adenocarcinoma.' Plose One 6(6):1-11 (e20636). Jun. 13, 2011.*

(Continued)

*Primary Examiner* — Christine H Matthews
(74) *Attorney, Agent, or Firm* — Casimir Jones, S.C.; Jason R. Bond

(57) ABSTRACT

The present invention relates to methods, systems, and compositions for treating and preventing cancer in a subject with the combination of radiation therapy and antigen presenting cells that have been exposed cancer stem cells or a portion thereof. In certain embodiments, the antigen presenting cells are dendritic cells that have been pulsed with ALDH$^{high}$ cancer stem cells.

3 Claims, 39 Drawing Sheets

(51) Int. Cl.
    *A61K 39/00* (2006.01)
    *A61K 45/06* (2006.01)
(52) U.S. Cl.
    CPC ............ *A61K 51/00* (2013.01); *A61N 5/1077* (2013.01); *A61K 2039/5154* (2013.01); *A61K 2039/5158* (2013.01); *A61N 2005/1024* (2013.01); *A61N 2005/1098* (2013.01)
(58) Field of Classification Search
    CPC .......... A61K 47/48584; A61K 47/4863; A61K 39/0011; A61K 47/48538; A61K 47/48592; A61K 47/486; A61K 47/48607; A61K 47/48615; A61K 47/48623; C07K 16/30; C07K 16/2833; C07K 14/4748; A61N 5/10; A61N 2005/1098
    See application file for complete search history.

(56) References Cited

FOREIGN PATENT DOCUMENTS

| WO | WO 2008070047 A2 * | 6/2008 | ......... C07K 14/4748 |
| WO | WO 2009064301 A1 * | 5/2009 | ....... G01N 33/57426 |
| WO | WO 2010011893 A1 * | 1/2010 | ......... A61K 39/0011 |
| WO | WO 2014/066615 | 5/2014 | |

OTHER PUBLICATIONS

Teitz-Tennenbaum et al. 'Radiotherapy Potentiates the Therapeutic Efficacy of Intratumoral 5 Dendritic Cell Administration'. Cancer Research. 63: 8466-8475. Dec. 1, 2003.*
Agarwala, Improving survival in patients with high-risk and metastatic melanoma: immunotherapy leads the way. Am J Clin Dermatol. 2003;4(5):333-346.
Awad et al., High ALDH activity identifies chemotherapy-resistant Ewing's sarcoma stem cells that retain sensitivity to EWS-FLI1 inhibition. PLoS One. Nov. 11, 2010;5(11):e13943.
Bao et al., Glioma stem cells promote radioresistance by preferential activation of the DNA damage response. Nature. 2006;444(7120):756-760.
Bertrand et al., Targeting Head and Neck Cancer Stem Cells to Overcome Resistance to Photon and Carbon Ion Radiation. Stem Cell Rev. Feb. 2014;10(1):114-26.
Boonyaratanakornkit et al., Selection of Tumorigenic Melanoma Cells Using ALDH. J Invest Dermatol. 2010;130(12):2799-2808.
Brown et al., Recognition and killing of brain tumor stem-like initiating cells by CD8+ cytolytic T cells. Cancer Res. 2009;69(23):8886-8893.
Carpentino et al., Aldehyde Dehydrogenase-Expressing Colon Stem Cells Contribute to Tumorigenesis in the Transition from Colitis to Cancer. Cancer Res. 2009;69(20):8208-8215.
Chang et al., A phase I trial of tumor lysate-pulsed dendritic cells in the treatment of advanced cancer. Clin Cancer Res. 2002;8(4):1021-1032.
Chang et al., Immunogenetic therapy of human melanoma utilizing autologous tumor cells transduced to secrete granulocyte-macrophage colony-stimulating factor. Hum Gene Ther 2000;11:839-50.
Chang et al., Phase II trial of autologous tumor vaccination, anti-CD3-activated vaccine-primed lymphocytes, and interleukin-2 in stage IV renal cell cancer. J Clin Oncol. 2003;21(5):884-890.
Charafej-Jauffret et al., Aldehyde Dehydrogenase 1-Positive Cancer Stem Cells Mediate Metastasis and Poor Clinical Outcome in Inflammatory Breast Cancer. Clinical Cancer Research. 2010;16(1):45-55.
Chen et al., Understanding and targeting cancer stem cells: therapeutic implications and challenges. Acta Pharmacol Sin. 2013;34(6):732-740.
Clay et al., Single-marker identification of head and neck squamous cell carcinoma cancer stem cells with aldehyde dehydrogenase. Head Neck 2010;32:1195-201.
Contag et al., Definition of an Enhanced Immune Cell Therapy in Mice That Can Target Stem-Like Lymphoma Cells. Cancer Res. 2010;70(23):9837-9845.
Dannull et al., Enhancement of vaccine-mediated antitumor immunity in cancer patients after depletion of regulatory T cells. J Clin Invest 2005;115:3623-33.
Deleo, Targeting cancer stem cells with ALDH1A1-based immunotherapy. Oncoimmunology. May 1, 2012;1(3):385-387.
Deng et al., Distinct Expression Levels and Patterns of Stem Cell Marker, Aldehyde Dehydrogenase Isoform 1 (ALDH1), in Human Epithelial Cancers. PLoS One. 2010;5(4):e10277.
Dougan et al., Immune therapy for cancer. Annu Rev Immunol. 2009;27:83-117.
Duarte et al., Preventive cancer stem cell-based vaccination reduces liver metastasis development in a rat colon carcinoma syngeneic model. Stem Cells. 2013;31(3):423-432.
Garcia-Hernandez et al., Prostate stem cell antigen vaccination induces a longterm protective immune response against prostate cancer in the absence of autoimmunity. Cancer Res. 2008;68(3):861-869.
Ginestier et al., ALDH1 is a marker of normal and malignant human mammary stem cells and a predictor of poor clinical outcome. Cell Stem Cell. 2007;1(5):555-567.
Huang et al., Aldehyde Dehydrogenase 1 is a Marker for Normal and Malignant Human Colonic Stem Cells (SC) and Tracks SC Overpopulation during Colon Tumorigenesis. Cancer Res. 2009;69(8):3382-3389.
Ito et al., Anti-CD137 monoclonal antibody administration augments the antitumor efficacy of dendritic cell-based vaccines. Cancer Res. 2004;64(22):8411-8419.
Jachetti et al., Prostate cancer stem cells are targets of both innate and adaptive immunity and elicit tumor-specific immune responses. Oncoimmunology. May 1, 2013;2(5):e2452.
Januchowski et al., The role of aldehyde dehydrogenase (ALDH) in cancer drug resistance. Biomed Pharmacother. 2013;67(7):669-80.
Kalbasi et al., Radiation and immunotherapy: a synergistic combination. J Clin Invest. 2013;123(7):2756-2763.
Kirk et al., T cell-dependent antitumor immunity mediated by secondary lymphoid tissue chemokine: augmentation of dendritic cell-based immunotherapy. Cancer Res 2001;61:2062-70.
Kjaergaard et al., Active immunotherapy for advanced intracranial murine tumors by using dendritic cell-tumor cell fusion vaccines. J Neurosurg 2005;103:156-64.
Le Magnen et al., Characterization and Clinical Relevance of ALDHbright Populations in Prostate Cancer. Clin Cancer Res. 2013;19(19):5361-5371.
Li et al., In vivo sensitized and in vitro activated B cells mediate tumor regression in cancer adoptive immunotherapy. J Immunol 2009;183:3195-203.
Li et al., Intrinsic resistance of tumorigenic breast cancer cells to chemotherapy. J Natl Cancer I. 2008;100(9):672-679.
Liao et al., Susceptibility to cytotoxic T cell lysis of cancer stem cells derived from cervical and head and neck tumor cell lines. J Cancer Res Clin Oncol. 2013;139(1):159-170.
Mina et al., Rethinking the metastatic cascade as a therapeutic target. Nat Rev Clin Oncol. 2011;8(6):325-332.
Moyer et al., Intratumoral dendritic cells and chemoradiation for the treatment of murine squamous cell carcinoma. J Immunother 2008;31:885-95.
Nandi et al., Low-dose radiation enhances survivin-mediated virotherapy against malignant glioma stem cells. Cancer Res. 2008;68(14):5778-5784.
Ning et al., Abstract 3322: Protective antitumor immunity induced by ALDEFLUOR+ enriched cancer stem cells. Cancer Research: Apr. 15, 2010; vol. 70, Issue 8, Supplement 1, 1 page.
Ning et al., Cancer Stem Cell Vaccination Confers Significant Antitumor Immunity. Cancer Res. 2012;72(7):1853-1864.
Pan et al., Concise Review: Targeting Cancer Stem Cells Using Immunologic Approaches. Stem Cells. Jul. 2015;33(7):2085-92.

(56) References Cited

OTHER PUBLICATIONS

Pearce et al., Characterization of cells with a high aldehyde dehydrogenase activity from cord blood and acute myeloid leukemia samples. Stem Cells. 2005;23(6):752-760.

Pellegatta et al., Neurospheres enriched in cancer stem-like cells are highly effective in eliciting a dendritic cell-mediated immune response against malignant gliomas. Cancer Res. 2006;66(21):10247-10252.

Phillips et al., The response of CD24(−/low)/CD44(+) breast cancer-initiating cells to radiation. J Natl Cancer I. 2006;98(24):1777-1785.

Prieto et al., Enrichment of CD8+ cells from melanoma tumor-infiltrating lymphocyte cultures reveals tumor reactivity for use in adoptive cell therapy. J Immunother 2010;33:547-56.

Prince et al., Evaluation of the immunogenicity of ALDH(high) human head and neck squamous cell carcinoma cancer stem cells in vitro. Oral Oncol. Aug. 2016;59:30-42.

Redman et al., Phase Ib trial assessing autologous, tumor-pulsed dendritic cells as a vaccine administered with or without IL-2 in patients with metastatic melanoma. J Immunother. 2008;31(6):591-598.

Shafee et al., Cancer stem cells contribute to cisplatin resistance in Brca1/p53-mediated mouse mammary tumors. Cancer Res 2008;68:3243-50.

Tanigawa et al., Antitumor reactivity of lymph node cells primed in vivo with dendritic cell-based vaccines. J Immunother. 2001;24(6):493-501.

Teitz-Tennenbaum et al., Targeting cancer stem cells via dendritic-cell vaccination. Oncoimmunology. 2012;1(8):1401-1403.

Tupchong et al., Randomized Study of Preoperative Versus Postoperative Radiation-Therapy in Advanced Head and Neck-Carcinoma—Long-Term Follow-up of Rtog Study 73-03. Int J Radiat Oncol. 1991;20(1):21-28.

Valent et al., Heterogeneity of neoplastic stem cells: theoretical, functional, and clinical implications. Cancer Res. 2013;73(3):1037-1045.

Van Den Hoogen et al., High Aldehyde Dehydrogenase Activity Identifies Tumor-Initiating and Metastasis-Initiating Cells in Human Prostate Cancer. Cancer Res. 2010;70(12):5163-5173.

Visus et al., Targeting ALDH(bright) human carcinoma-initiating cells with ALDH1A1—specific CD8(+) T cells. Clin Cancer Res. 2011;17(19):6174-6184.

Xu et al., Antigen-Specific T-Cell Response from Dendritic Cell Vaccination Using Cancer Stem-Like Cell-Associated Antigens. Stem Cells. 2009;27(8):1734-1740.

Yamauchi et al., Induction of cancer metastasis by cyclophosphamide pretreatment of host mice: An opposite effect of chemotherapy. Cancer Res. 2008;68(2):516-520.

Yasuda et al., Ovarian Cancer Stem Cells Are Enriched in Side Population and Aldehyde Dehydrogenase Bright Overlapping Population. PLoS One. 2013;8(8):e6818.

Zhou et al., Promise of cancer stem cell vaccine. Hum Vaccin Immunother. 2015;11(12):2796-9.

International Search Report and Written Opinion for PCT/US2013/066578, dated Jan. 17, 2014, 12 pages.

* cited by examiner

A

C

A

A

FIG. 22
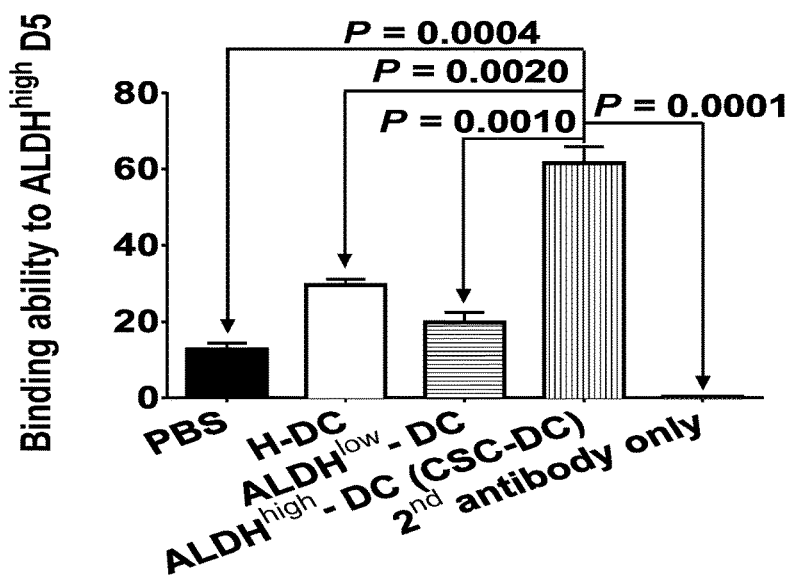
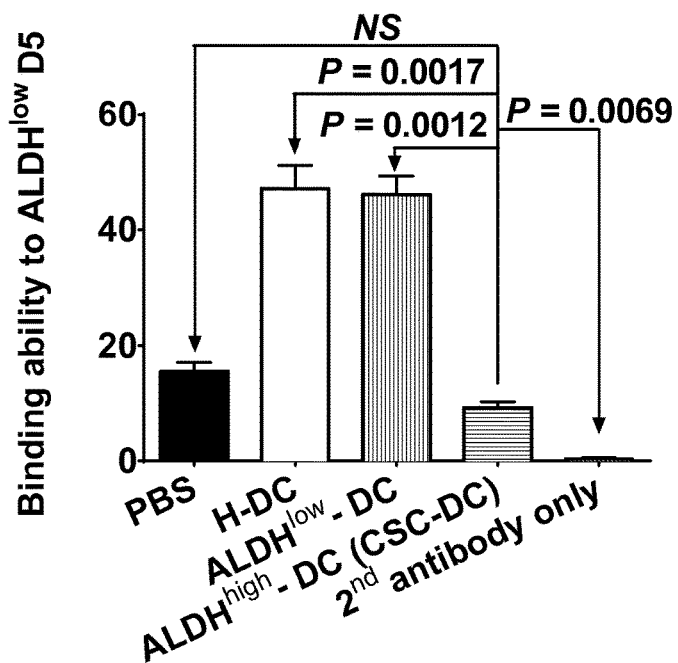

FIG. 23
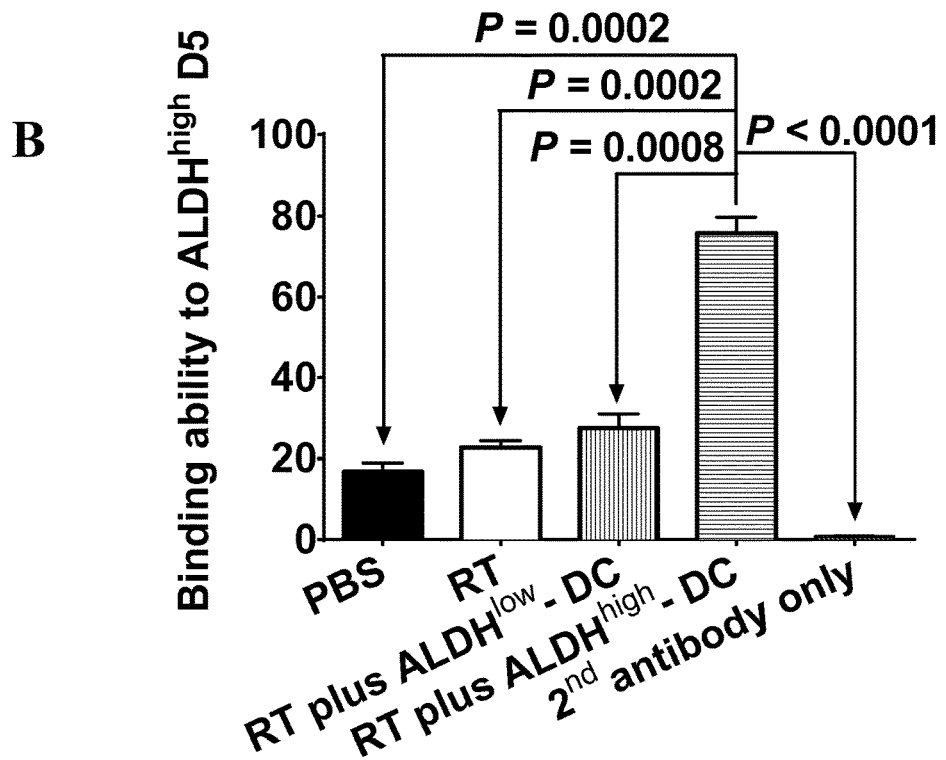
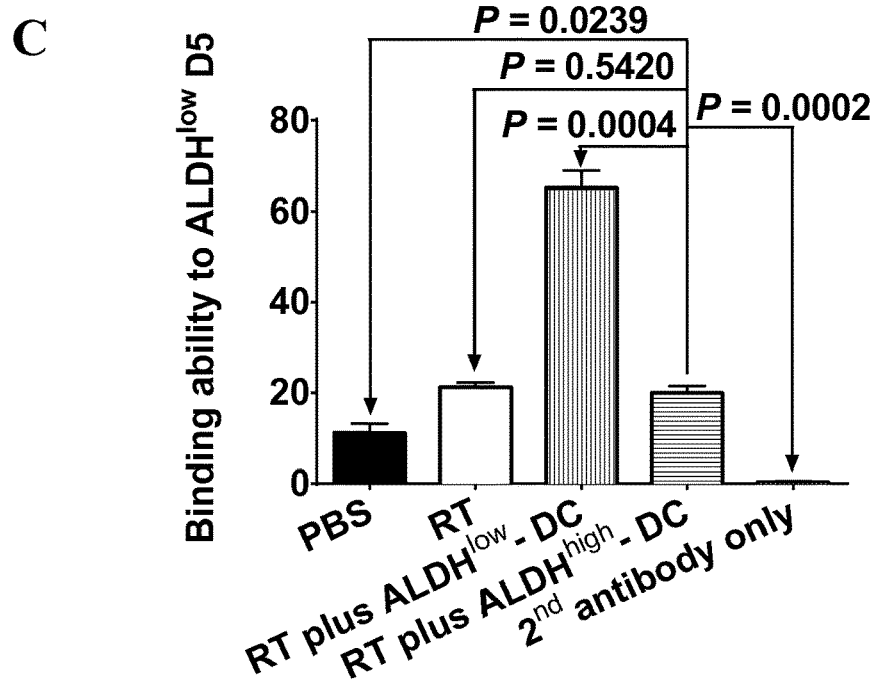

CANCER STEM CELL VACCINATION AND TREATMENT

The present application claims priority to U.S. Provisional application Ser. No. 61/717,902 filed Oct. 24, 2012, which is herein incorporated by reference in its entirety.

This invention was made with government support under National Institutes of Health Grant No. CA82529. The government has certain rights in the invention.

FIELD OF THE INVENTION

The present invention relates to methods, systems, and compositions for treating and preventing cancer in a subject with the combination of radiation therapy and antigen presenting cells that have been exposed cancer stem cells or a portion thereof. In certain embodiments, the antigen presenting cells are dendritic cells that have been pulsed with ALDEFLUOR+/ALDH$^{high}$ cancer stem cells.

BACKGROUND OF THE INVENTION

Clinical trials to treat patients with cancer using adoptively transferred T cells (1-3) or dendritic cells (DC; refs. 4-6) have shown therapeutic efficacy for patients with advanced diseases. However, the clinical responses to such immunotherapeutic approaches have been confined to a limited percentage of treated patients. Generally, bulk tumor masses with heterogeneous populations of cancer cells have been used as a source of antigen either to generate effector T cells or to prime DC vaccines. Human tumors are composed of heterogeneous tumor cell clones that differ with respect to proliferation, differentiation, and ability to initiate daughter tumors. The inability to target cancer stem cells (CSC) with current immune approaches may be a significant factor for treatment failures.

The identification of human CSCs (7-17) presents a new paradigm for the development of cancer treatments. These stem cells have been shown to be relatively resistant to conventional chemotherapeutic regimens and radiation (18, 19) and are postulated to be the cells responsible for the relapse and progression of cancers after such therapies. In an analogous fashion, the CSC phenomenon may adversely affect the development of effective immunotherapies for cancer. These therapies have involved targeting cells that express differentiated tumor antigens. However, such antigens may be selectively expressed on differentiated tumor cells. CSCs that do not express these antigens may thus escape these immunologic interventions.

SUMMARY OF THE INVENTION

The present invention relates to methods, systems, and compositions for treating and preventing cancer in a subject with the combination of radiation therapy and antigen presenting cells that have been exposed cancer stem cells or a portion thereof. In certain embodiments, the antigen presenting cells are dendritic cells that have been pulsed with ALDEFLUOR+/ALDH$^{high}$ cancer stem cells.

In some embodiments, the present invention provides methods of treating (and/or preventing) cancer in a subject (or in a subject suspected of having cancer) comprising: treating a subject with the combination of an effective amount of radiation therapy and administration of an effective amount of antigen presenting cells, such that at least some cancer cells in the subject are killed, wherein the antigen presenting cells have been exposed to cancer stem cells or at least an antigenic portion of the cancer stem cells. In certain embodiments, the antigen presenting cells comprise dendritic cells. In other embodiments, the antigen presenting cells comprise macrophages. In further embodiments, the antigen presenting cells comprise B-cells.

In particular embodiments, the treating of the subject increases the length of survival of the subject compared to the length of survival with radiation therapy without administration of the antigen presenting cells. In further embodiments, the at least an antigenic portion of the cancer stem cells comprises a cell lysate of the cancer stem cells. In particular embodiments, the cancer stem cells are ALDH+, or CD44+CD24$^{-/low}$, or CD44+CD24+ or CD44+ $\alpha_2\beta_1^{hi}$CD133+, or CD44+BMI1+, or CD44+EpCAM$^{high}$, or CD44+CK5+CK20−, or CD44+ESA+.

In particular embodiments, the subject is a human. In further embodiments, the subject has a cancer selected from the group consisting of: melanoma, breast cancer, prostate cancer, pancreatic cancer, lung cancer, liver cancer, brain cancer, head and neck squamous cell carcinoma, skin cancer, and colon cancer. In other embodiments, the methods further comprise further treating the subject with a chemotherapeutic agent. In additional embodiments, the chemotherapeutic agent is selected from Table 1. In other embodiments, the radiation therapy comprises external beam radiation therapy. In certain embodiments, the radiation therapy comprises internal radiation therapy.

In certain embodiments, the present invention provides systems comprising: a) antigen presenting cells that have been exposed to cancer stem cells or at least an antigenic portion of the cancer stem cells, and b) a radioactive implant configured for use in internal radiation cancer therapy. In some embodiments, the antigen presenting cells comprise dendritic cells. In particular embodiments, the cancer stem cells are ALDEFLUOR+/ALDH$^{high}$.

In additional embodiments, the present invention provides systems comprising: a) antigen presenting cells that have been exposed to cancer stem cells or at least an antigenic portion of the cancer stem cells, and b) a device configured to emit radiation used during external radiation cancer therapy. In further embodiments, the antigen presenting cells comprise dendritic cells. In additional embodiments, the cancer stem cells are ALDEFLUOR+/ALDH$^{high}$.

In some embodiments, the present invention provides compositions comprising: antigen presenting cells that have been exposed to cancer stem cells or at least an antigenic portion of the cancer stem cells, and radionucleotides.

DESCRIPTION OF THE DRAWINGS

FIG. 2 shows the mean tumor sizes of the 4 treatment groups (no treatment, radiation only, radiation plus negative vaccine, and radiation plus positive vaccine).

As seen in FIG. 3, there was a significant difference in the survival rate between ALDH$^{low}$ and ALDH$^{high}$ vaccine when radiation therapy was also employed.

FIG. 12 shows that the ALDH$^{high}$ vaccine treated mice had significantly smaller tumor size after 37 days compared to no treatment, TPDC, and ALDH$^{low}$ vaccine treated animals.

(FIG. 16A) p values comparing lung metastasis (n=11) among groups treated as indicated in the table. (FIG. 16B) Bar graph showing the percentage of lung metastasis. (FIG. 16C) Lung metastasis was verified by hematoxylin and eosin (H&E) staining Representative graphs show the histologic alternation of the lung tissues. Lung tissue harvested from a normal B6 mouse served as control. The red arrows point to the tumor lesions in the lung tissues. Data are representative of 3 independent experiments performed.

(FIG. 17A) p values comparing lung metastasis (n=11) among groups treated as indicated. RT plus ALDH$^{high}$-DC (CSC-DC) significantly inhibited the distant lung metastasis. (FIG. 17B) Bar graph showing the percentage of lung metastasis. (FIG. 17C) H&E staining of histologic specimens of lung tissues, which were harvest from mice subjected to PBS, RT alone, RT plus ALDH$^{low}$-DC vs. RT plus ALDH$^{high}$ CSC-DC vaccine. Representative graphs show the histologic alternation of the lung tissues. Lung tissue harvested from a normal B6 mouse served as control. The red arrows point to the tumor lesions in the lung tissues (magnification, 100×). Data are representative of 3 independent experiments performed.

(FIG. 18A) The expression of CCR10 after mice treated with PBS, H-DC, ALDH$^{low}$-DC or ALDH$^{high}$-DC (CSC-DC). The bar graph shows the results of 3 experiments with SE using the D5 cells harvested from 3 animals in each experiment group. (FIG. 18B) Flow cytometry graphs of CCR10, which were generated using mixed D5 cells harvested from multiple animals in each treatment group. Same procedures were used to detect the expression of CCR7 (C and D) on D5 tumors harvested from the host subjected to PBS, H-DC, ALDH$^{low}$-DC or ALDH$^{high}$-DC treatment respectively.

(FIGS. 19A and B): The expression of CCR10 on subcutaneous tumors harvested from mice treated with PBS, RT alone, RT plus ALDH$^{low}$-DC or RT plus ALDH$^{high}$-DC (CSC-DC). The bar graph shows the results of 3 experiments with SE using the D5 cells harvested from 3 animals in each experiment group.

The Flow cytometry graphs of CCR10 were generated using mixed D5 cells harvested from multiple animals in each treatment group. Same procedures were used to detect the expression of CCR7 (FIGS. 19C and D) on D5 tumors harvested from the host subjected to PBS, RT alone, RT plus ALDH$^{low}$-DC or RT plus ALDH$^{high}$-DC (CSC-DC) treatment respectively.

Figure 20:
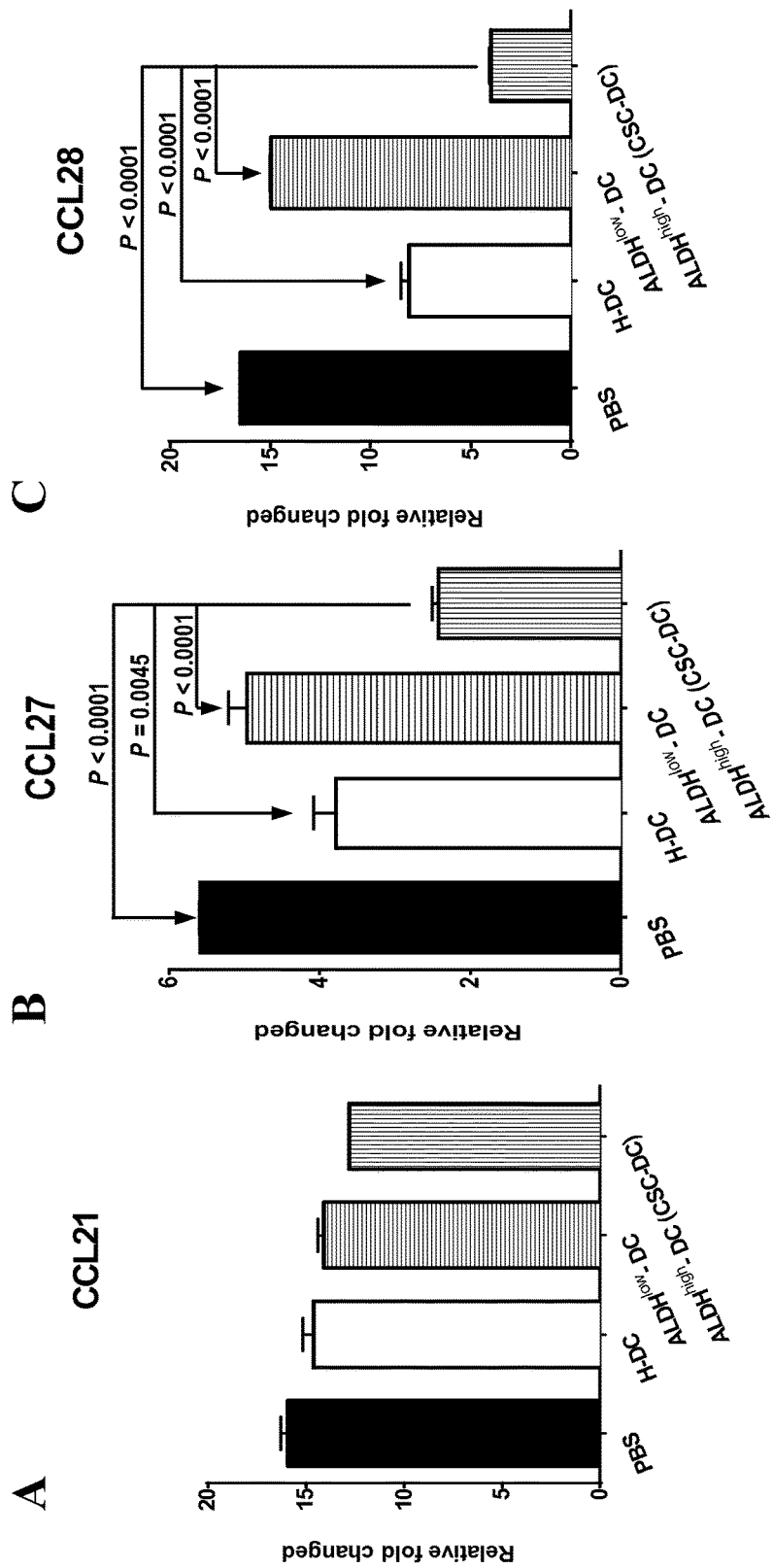
Figure 20:
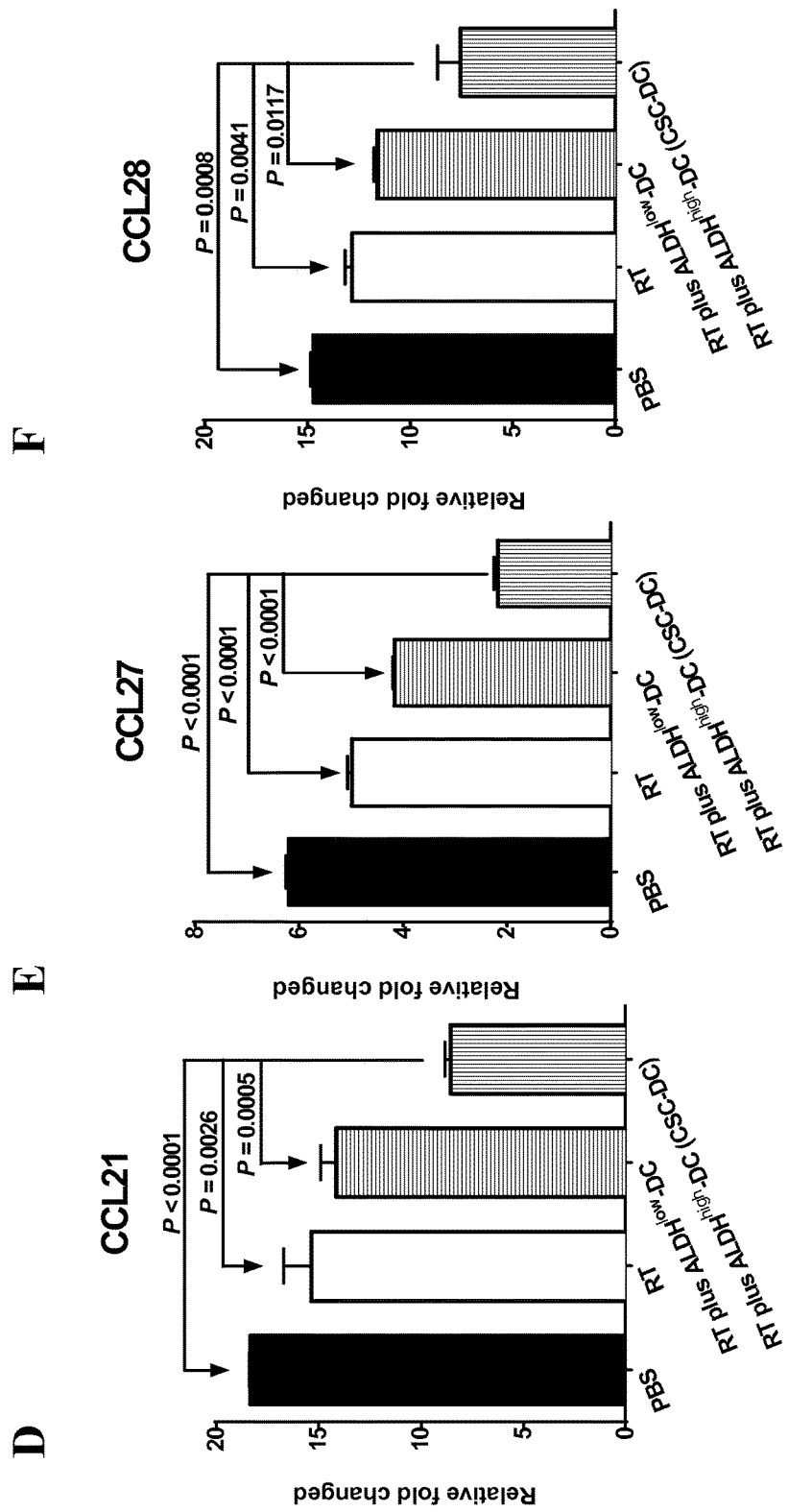

FIG. 20 shows ALDH$^{high}$-DC (CSC-DC) and RT plus CSC-DC vaccine significantly reduced chemokine mRNA levels in the lung tissues harvested from D5-bearing host in a micrometastatic disease setting (FIGS. 20A-C), and in the established D5 model (FIG. 20D-F). Analysis of the expression levels of the corresponding chemokines for CCR7 and CCR10 in the lung tissues collected from micrometastatic and established D5-bearing mice was done by real-time quantitative PCR. (FIGS. 20A, D) The mRNA expression of CCL21 (ligand of CCR7) in the lung tissues harvested from mice with micrometastatic disease (FIG. 20A) or the established disease (FIG. 20D) subjected to treatment as indicated respectively. The ligands for CCR10, CCL27 (FIGS. 20B, E) and CCL28 (FIGS. 20C, F) were evaluated using the same PCR procedures. Data were repeated in a second experiment.

Figure 21:
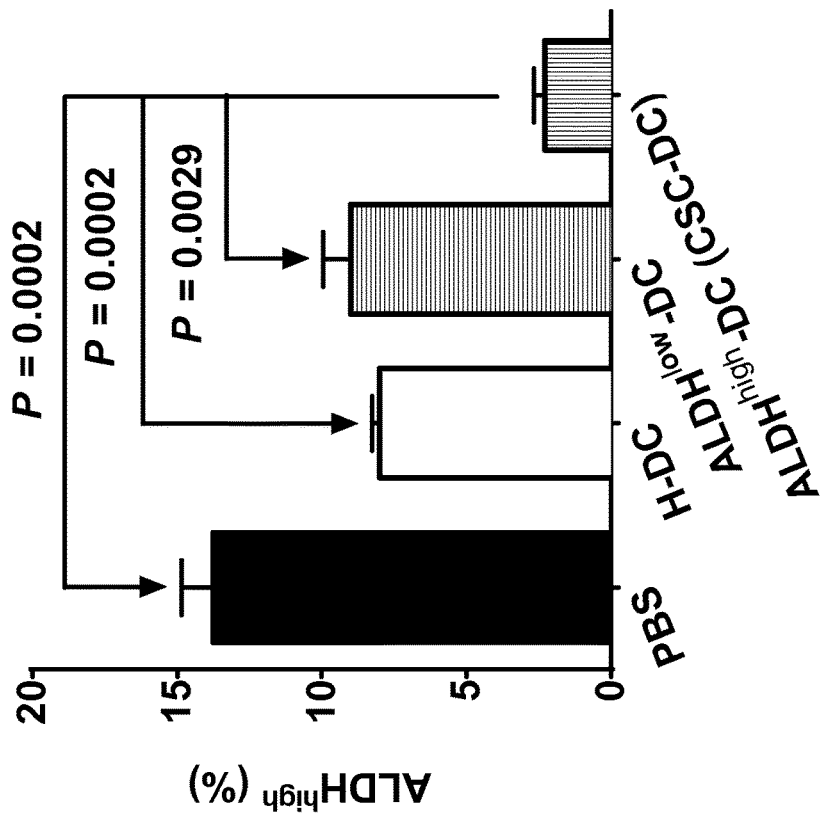
Figure 21:
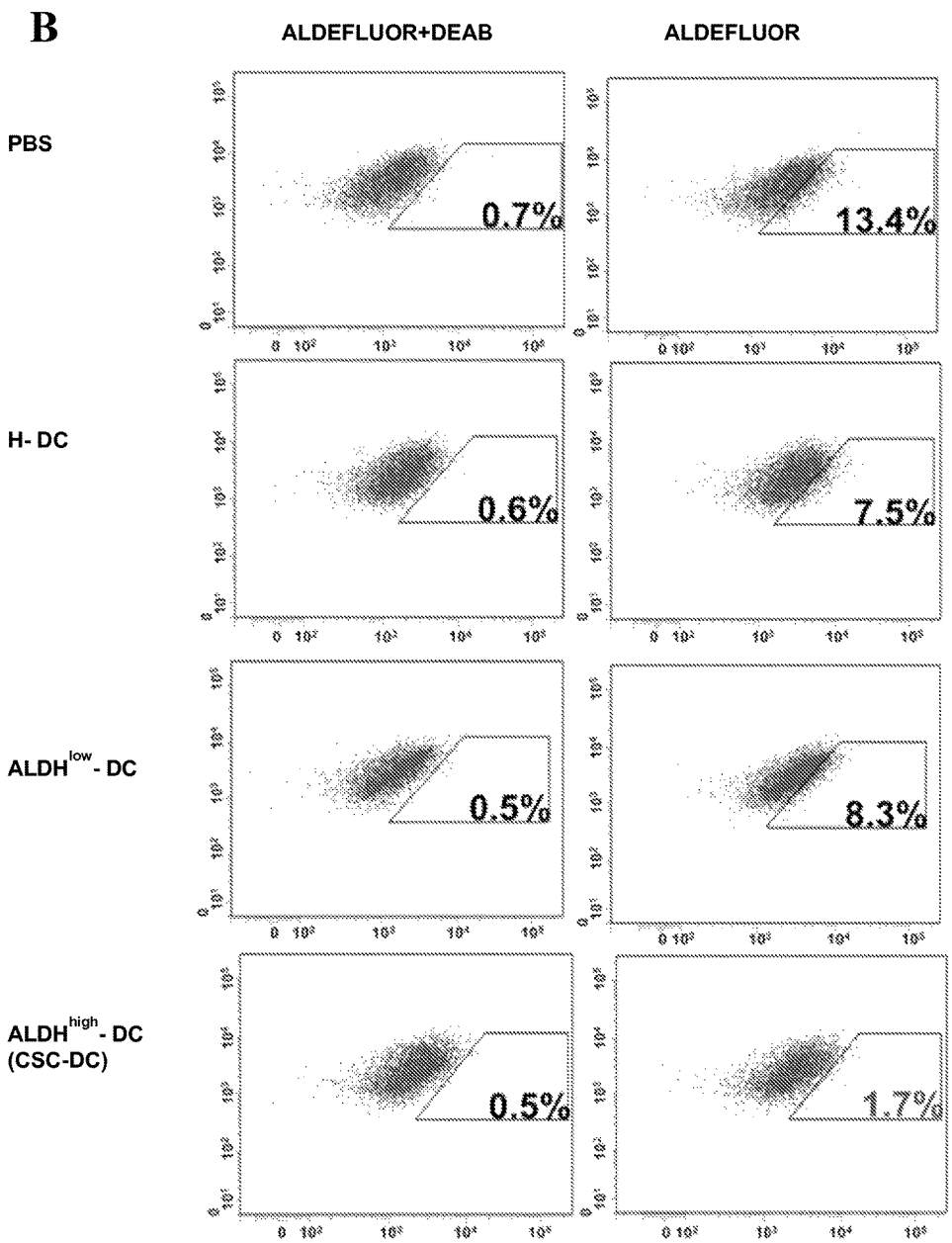
Figure 21:
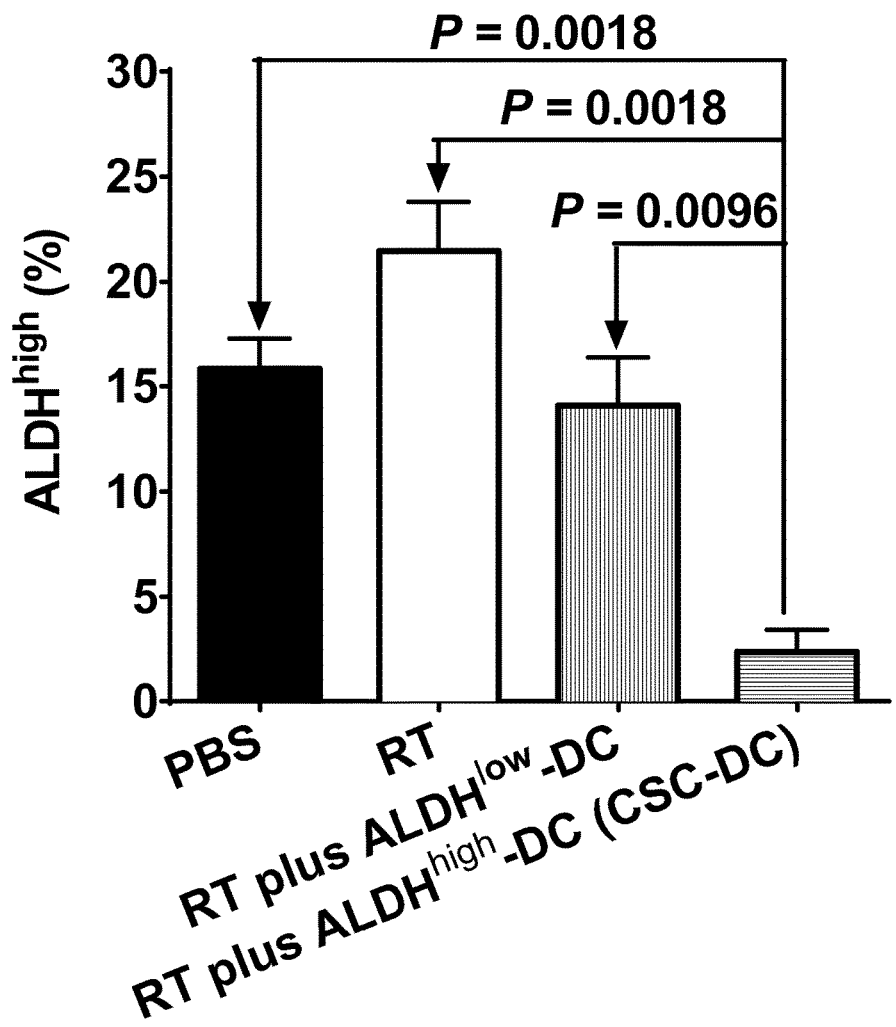
Figure 21:
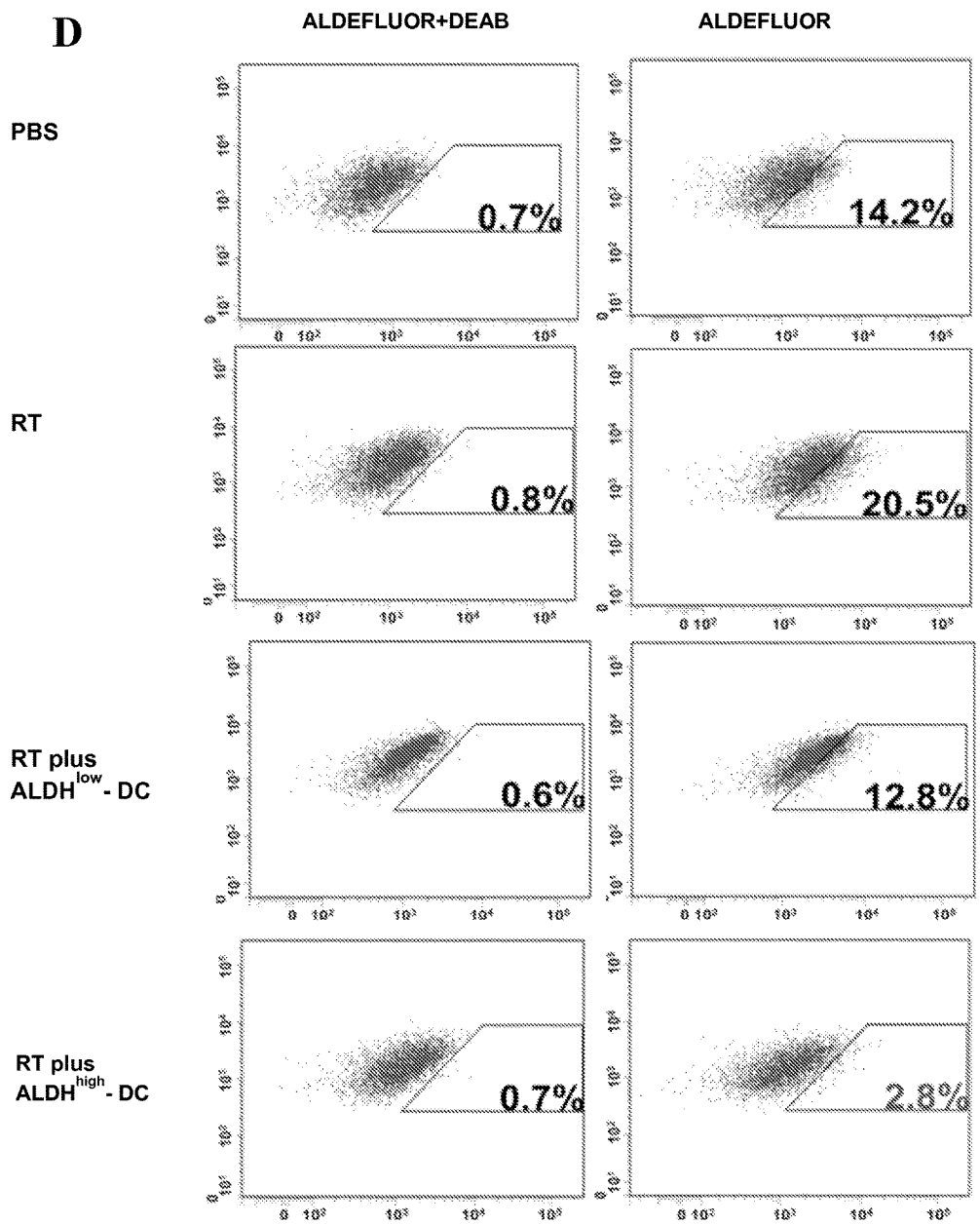

FIG. 21 shows CSC-DC or RT plus CSC-DC vaccine treatment significantly decreased the percentage of ALDH$^{high}$ cells in the primary s.c tumors freshly harvested from the micrometastatic (21A, 21B) or the established (C, D) D5 models. Tumor cells incubated with ALDEFLUOR in the presence of ALDH inhibitor DEAB were used as the control. Experiments were repeated at least 3 times by using s.c tumor cells from multiple individual mouse of each treatment group (21A, 21C). Mixed tumor cells from multiple mice of each group were used to generate representative flow cytometry graphs (21B, 21D).

Figure 22:
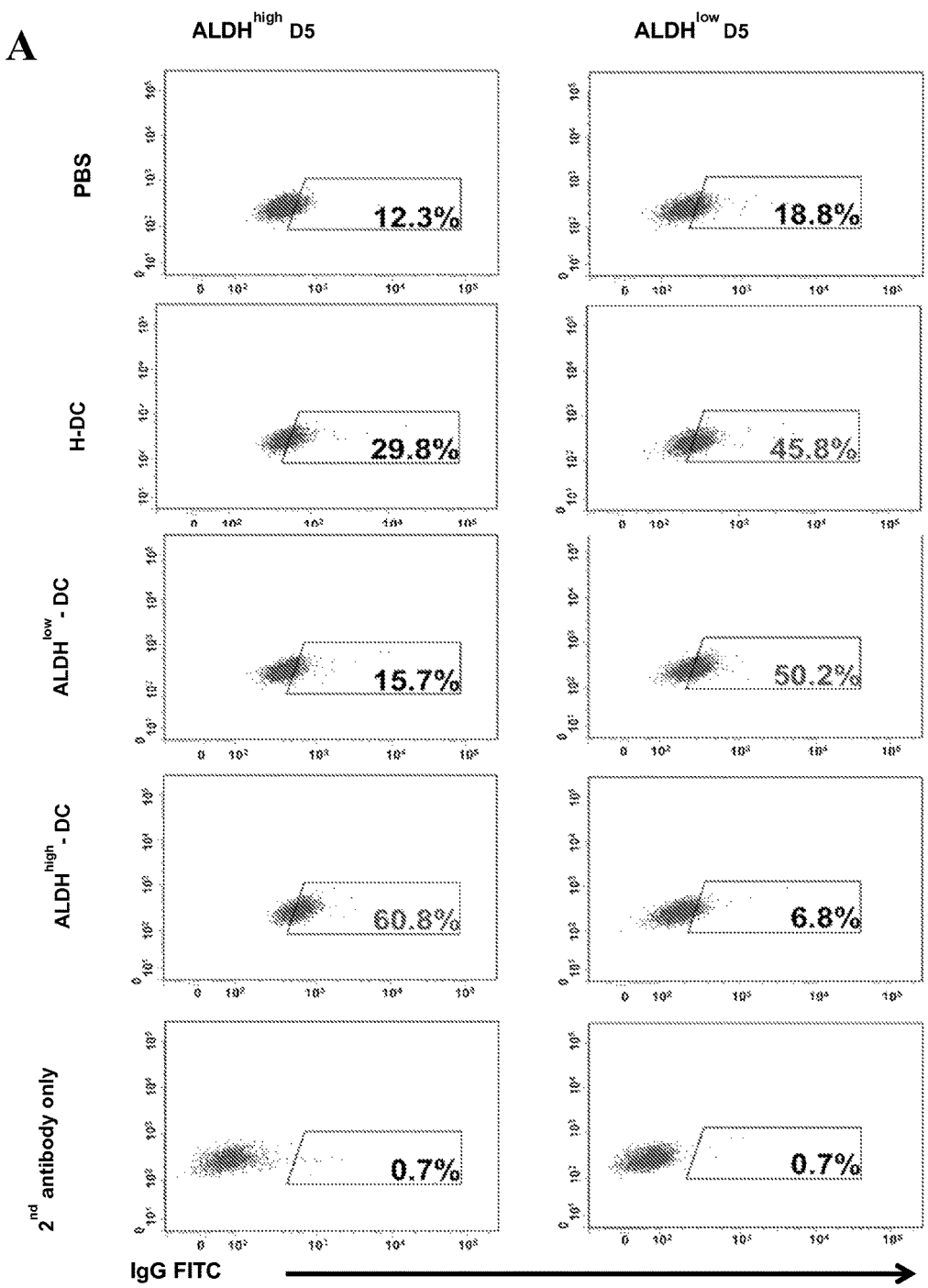

FIG. 22 shows antibody produced by D5 CSC vaccine-primed B cells bind to D5 CSCs specifically. In the micrometastatic D5 model, spleens were collected and splenocyte B cells were activated with LPS/anti-CD40. (FIG. 22A) Representative flow cytometry showing specific binding of CSC-DC vaccine-primed Ab to ALDH$^{high}$ CSCs, while H-DC or ALDH$^{low}$-DC vaccine-primed Abs preferentially bind to ALDH$^{low}$ cells. (FIG. 22B) Statistic analysis of the binging to ALDH$^{high}$ CSCs by immune supernatants primed by PBS, H-DC, ALDH$^{low}$-DC or ALDH$^{high}$-DC respectively. Binding experiments were repeated 3 times. (FIG. 22C) Statistic analysis of the binding to ALDH$^{low}$ D5 cells by immune supernatants primed by PBS, H-DC, ALDH$^{low}$-DC or ALDH$^{high}$-DC respectively. Binding experiments were repeated 3 times.

Figure 23:
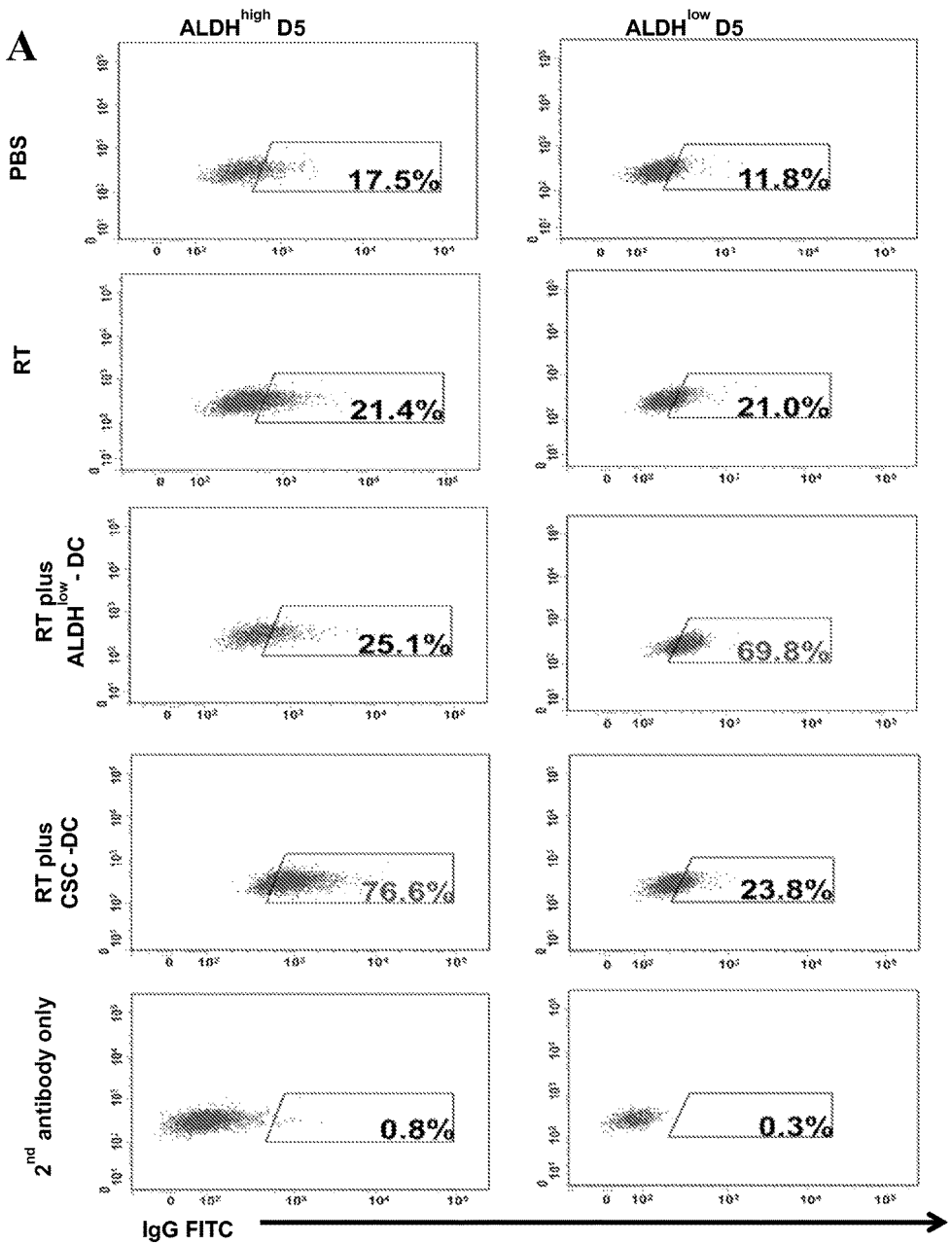

FIG. 23 shows CSC-based vaccination confers specific binging to CSCs by vaccine-primed antibodies in the setting of local tumor irradiation of established D5 model. Spleens were collected from D5-bearing hosts subjected to PBS, RT alone, RT plus ALDH$^{low}$-DC or RT plus ALDH$^{high}$-DC therapy. Splenocyte B cells were activated with LPS/anti-CD40. (FIG. 23A) Representative flow cytometry showing specific binding of CSC-DC vaccine-primed Ab to ALDH$^{high}$ CSCs, while ALDH$^{low}$-DC vaccine-primed Abs preferentially bind to ALDH$^{low}$ cells in the same setting of RT. (FIG. 23B) Statistic analysis of the binging to ALDH$^{high}$ D5 CSCs by immune supernatants primed by PBS, RT alone, RT plus ALDH$^{low}$-DC or RT plus ALDH$^{high}$-DC therapy respectively. Binding experiments were repeated 3 times. (FIG. 23C) Statistic analysis of the binging to ALDH$^{low}$ D5 non-CSCs by immune supernatants primed by PBS, RT alone, RT plus ALDH$^{low}$-DC or RT plus ALDH$^{high}$-DC therapy respectively. Binding experiments were repeated 3 times.

Figure 24:
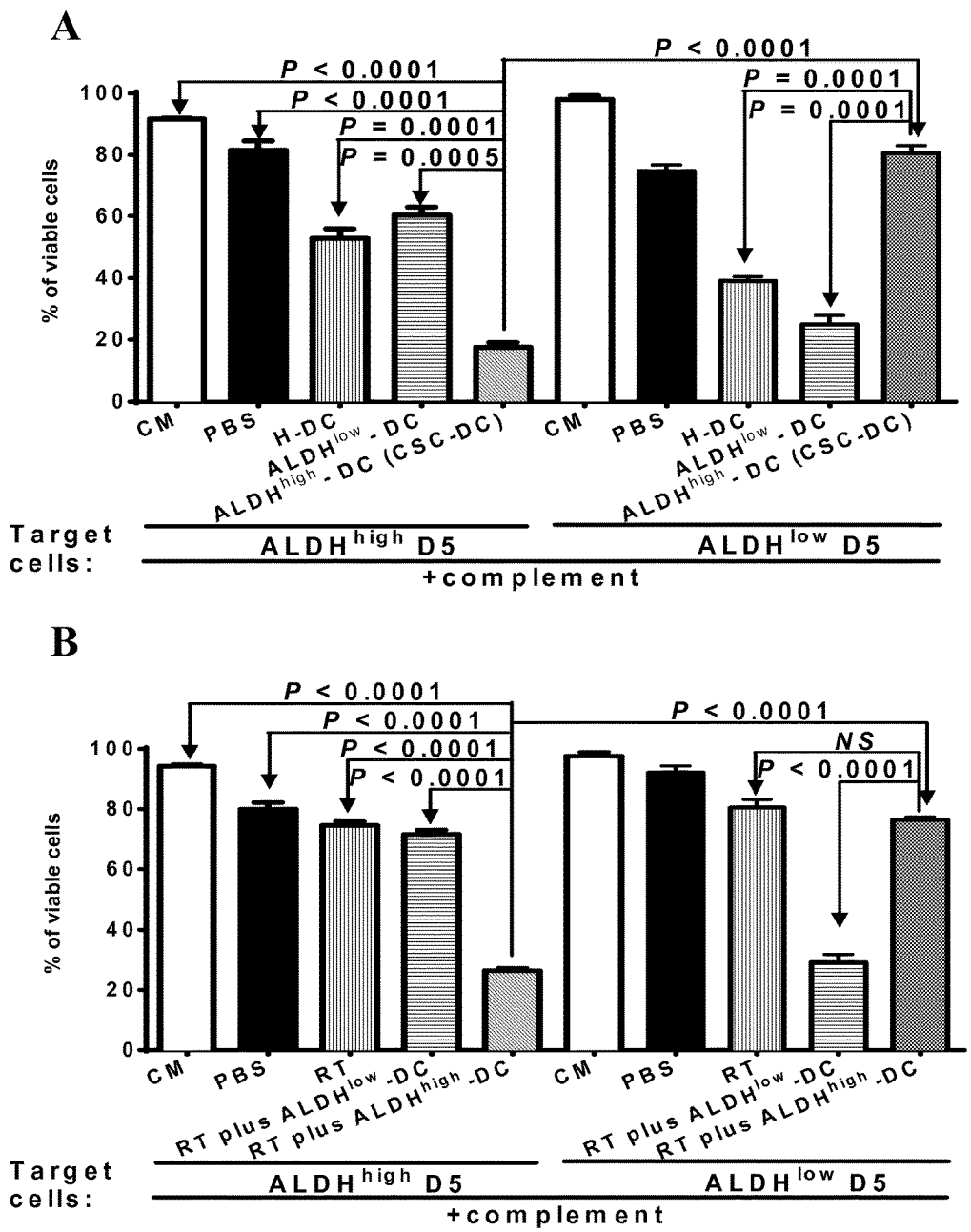

FIG. 24 shows CSC-DC vaccine-primed antibody selectively targets CSCs via complement-dependent cytotoxicity (CDC). Antibody and complement mediated cytotoxicity was measured by incubating viable ALDH$^{high}$ D5 CSCs vs. ALDH$^{low}$ D5 non-CSCs as targets with culture supernatants of immune B cells harvested from mice subjected to different treatments as indicated in the micrometastatic D5 melanoma model (FIG. 24A) or in the established D5 model (FIG. 24B). The data is expressed as the percentage of viable cells. Lower percentage of viable cells means more cell lysis.

DEFINITIONS

As used herein, the term "subject" refers to any animal (e.g., a mammal), including, but not limited to, humans, non-human primates, rodents, and the like (e.g., which is to be the recipient of a particular treatment, or from whom cancer stem cells are harvested). Typically, the terms "subject" and "patient" are used interchangeably, unless indicated otherwise herein.

As used herein, the term "subject is suspected of having cancer" refers to a subject that presents one or more signs or symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "effective amount" refers to the amount of a composition or treatment sufficient to effect beneficial or desired results. An effective amount can be administered in one or more administrations, applications or dosages and is not intended to be limited to a particular formulation or administration route.

As used herein, the term "administration" refers to the act of giving a cancer stem cell vaccine (e.g., pulsed antigen presenting cells) drug, prodrug, or other agent, or therapeutic treatment to a subject. Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

"Co-administration" refers to administration of more than one chemical agent or therapeutic treatment (e.g., radiation therapy) to a physiological system (e.g., a subject or in vivo, in vitro, or ex vivo cells, tissues, and organs). "Co-administration" of the respective chemical agents and therapeutic treatments (e.g., radiation therapy) may be concurrent, or in any temporal order or physical combination.

"Enriched," as in an enriched population of cells, can be defined based upon the increased number of cells having a particular marker in a fractionated set of cells as compared with the number of cells having the marker in the unfractionated set of cells. However, the term "enriched" can also be defined by tumorigenic function as the minimum number of cells that generate a cancer (e.g., a tumor) at a limited dilution frequency (e.g., in a mouse model). For example, if 500 cancer stem cells form tumors in 63% of test animals, but 5000 unfractionated tumor cells are required to form tumors in 63% of test animals, then the cancer stem cell population is 10-fold enriched for tumorigenic activity.

As used herein, the terms "drug" and "chemotherapeutic agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds. Examples of drugs are found in Table 1 below.

DETAILED DESCRIPTION OF THE INVENTION

The present invention relates to methods, systems, and compositions for treating and preventing cancer in a subject with the combination of radiation therapy and antigen presenting cells that have been exposed cancer stem cells or a portion thereof. In certain embodiments, the antigen presenting cells are dendritic cells that have been pulsed with ALDEFLUOR$^+$/ALDH$^{high}$ cancer stem cells.

The present invention is not limited by the type of cancer stem cells used to load the antigen presenting cells. Examples of cancers from which cancer stem cells can be isolated or enriched, include, but are not limited to, lymphomas (e.g., Hodgkin's disease and non-Hodgkin's disease), leukemias (e.g., acute leukemia, acute lymphocytic leukemia, acute myelocytic leukemia, myeloblastic, promyelocytic, myelomonocytic, monocytic, erythroleukemia, chronic leukemia, chronic myelocytic, (granulocytic) leukemia, and chronic lymphocytic leukemia), and sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma). The invention is also applicable to sarcomas and epithelial cancers, such as ovarian cancers and breast cancers, as well as to all solid tumors.

In certain embodiments, prior to treating a patient with radiation therapy and antigen presenting cells that have been exposed to cancer stem cells, a sample from a subject is tested to determine if, (and what type) of cancer stem cells the patient possesses. A subject's (e.g., a particular cancer patient's) cancer stem cells (e.g., once isolated and allowed to proliferate in vitro), can be analyzed and screened. For example, in some embodiments, analyzing a subject's cancer stem cells is used as a diagnostic for the subject. Thus, in some embodiments, the present invention provides methods for detection of expression of cancer stem cell biomarkers to identify if the patient has particular cancer stem cells or combinations thereof. In some embodiments, expression is measured directly (e.g., at the nucleic acid or protein level). In some embodiments, expression is detected in tissue samples (e.g., biopsy tissue). In other embodiments, expression is detected in bodily fluids (e.g., including but not limited to, plasma, serum, whole blood, mucus, and urine). In some preferred embodiments, cancer stem cell biomarkers are detected by measuring the levels of the cancer stem cell biomarker in cells and tissue (e.g., cancer cells and tissues). For example, in some embodiments, a cancer stem cell biomarker are monitored using antibodies or by detecting a cancer stem cell biomarker protein/nucleic acid (e.g., CD44, CD24, EpCam, CD49f, ALDH, mir-221, mir-110, and/or mir-93). In some embodiments, detection is performed on cells or tissue after the cells or tissues are removed from the subject. In other embodiments, detection is performed by visualizing the cancer stem cell biomarker in cells and tissues residing within the subject. In some embodiments, cancer stem cell biomarker are detected by measuring the expression of corresponding mRNA in a tissue sample (e.g., cancerous tissue). In some embodiments, RNA is detected by Northern blot analysis. Northern blot analysis involves the separation of RNA and hybridization of a complementary labeled probe.

In certain embodiments, an additional therapeutic agent is administered with the radiation therapy and the antigen presenting cells. Any therapeutic agent that can be co-administered with the agents of the present invention, or associated with the agents of the present invention is suitable for use in the methods of the present invention. Some embodiments of the present invention provide methods for administering least one additional therapeutic agent (e.g., including, but not limited to, chemotherapeutic antineoplastics, antimicrobials, antivirals, antifungals, and anti-inflammatory agents) and/or therapeutic technique (e.g., surgical intervention, radiotherapies).

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use with the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile,a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |

TABLE 1-continued

| | | |
|---|---|---|
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |

TABLE 1-continued

| | | |
|---|---|---|
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S- cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S$•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |

TABLE 1-continued

| | | |
|---|---|---|
| Megestrol acetate<br>17α(acetyloxy)-6-methylpregna-4,6-diene-<br>3,20-dione | Megace | Bristol-Myers Squibb |
| Melphalan, L-PAM<br>(4-[bis(2-chloroethyl) amino]-L-phenylalanine) | Alkeran | GlaxoSmithKline |
| Mercaptopurine, 6-MP<br>(1,7-dihydro-6 H-purine-6-thione monohydrate) | Purinethol | GlaxoSmithKline |
| Mesna<br>(sodium 2-mercaptoethane sulfonate) | Mesnex | Asta Medica |
| Methotrexate<br>(N-[4-[[(2,4-diamino-6-<br>pteridinyl)methyl]methylamino]benzoyl]-L-<br>glutamic acid) | Methotrexate | Lederle Laboratories |
| Methoxsalen<br>(9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane<br>(1,1-dichloro-2-(o-chlorophenyl)-2-(p-<br>chlorophenyl) ethane) | Lysodren | Bristol-Myers Squibb |
| Mitoxantrone<br>(1,4-dihydroxy-5,8-bis[[2-[(2-<br>hydroxyethyl)amino]ethyl]amino]-9,10-<br>anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin<br>(IL-11) | Neumega | Genetics Institute, Inc., Alexandria, VA |
| Oxaliplatin<br>(cis-[(1R,2R)-1,2-cyclohexanediamine-N,N']<br>[oxalato(2-)-O,O'] platinum) | Eloxatin | Sanofi Synthelabo, Inc., NY, NY |
| Paclitaxel<br>(5β,20-Epoxy-1,2a,4,7β,10β,13a-<br>hexahydroxytax-11-en-9-one 4,10-diacetate 2-<br>benzoate 13-ester with (2R,3 S)-N-benzoyl-3-<br>phenylisoserine) | TAXOL | Bristol-Myers Squibb |
| Pamidronate<br>(phosphonic acid (3-amino-1-hydroxypropylidene)<br>bis-, disodium salt, pentahydrate, (APD)) | Aredia | Novartis |
| Pegademase<br>((monomethoxypolyethylene glycol succinimidyl)<br>11-17-adenosine deaminase) | Adagen<br>(Pegademase<br>Bovine) | Enzon Pharmaceuticals, Inc., Bridgewater, NJ |
| Pegaspargase<br>(monomethoxypolyethylene glycol succinimidyl<br>L-asparaginase) | Oncaspar | Enzon |
| Pegfilgrastim<br>(covalent conjugate of recombinant methionyl<br>human G-CSF (Filgrastim) and<br>monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin<br>(antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine<br>(N-isopropyl-μ-(2-methylhydrazino)-p-toluamide<br>monohydrochloride) | Matulane | Sigma Tau Pharmaceuticals, Inc., Gaithersburg, MD |
| Quinacrine<br>(6-chloro-9-(1-methyl-4-diethyl-amine)<br>butylamino-2-methoxyacridine) | Atabrine | Abbott Labs |
| Rasburicase<br>(recombinant peptide) | Elitek | Sanofi-Synthelabo, Inc., |
| Rituximab<br>(recombinant anti-CD20 antibody) | Rituxan | Genentech, Inc., South San Francisco, CA |
| Sargramostim<br>(recombinant peptide) | Prokine | Immunex Corp |
| Streptozocin<br>(streptozocin 2-deoxy-2-<br>[[(methylnitrosoamino)carbonyl]amino]-a(and b)-<br>D-glucopyranose and 220 mg citric acid<br>anhydrous) | Zanosar | Pharmacia & Upjohn Company |
| Talc<br>($Mg_3Si_4O_{10}(OH)_2$) | Sclerosol | Bryan, Corp., Woburn, MA |

TABLE 1-continued

| | | |
|---|---|---|
| Tamoxifen ((Z)2-[4-(1,2-diphenyl-1-butenyl)phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radio immunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxy]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

EXPERIMENTAL

The following example is provided in order to demonstrate and further illustrate certain preferred embodiments and aspects of the present invention and are not to be construed as limiting the scope thereof.

Example 1

Combined Radiation and Cancer Stem Cell Vaccine Treatment

In this Example, the combined treatment of tumors with radiation therapy (RT) and cancer stem cell pulsed dendritic cells was tested.

Materials and Methods

Mice:

Female C57BL/6 (B6) mice were used at the 7 weeks of age or older. The University of Michigan Laboratory of Animal Medicine approved all the animal protocols.

Murine Tumors:

D5 is a poorly immunogenic melanoma of spontaneous origin syngeneic to B6 mice.

Tumor Models:

The first model involves the treatment of established tumors using CSC-DC vaccine as an additional strategy to radiation therapy (RT). Day 5 sc D5 tumors were treated with localized RT with repeat treatments on day 6. Vaccine therapy commenced on day 7. This combination therapy was repeated twice with one week apart. The second model involved the treatment of micrometastatic disease. Vaccination was initiated 24 hours after sub-cutaneous (s.c.) inoculation of D5 tumor cells in B6 mice, with repeated the vaccination one week later.

Vaccination:

ALDHFLUOR+ and ALDHFLUOR− cells were isolated from cultured D5 cells. Bone marrow-derived dendritic cells (DCs) were cultured in IL-4 and GM-CSF and were pulsed with the lysate of ALDHFLUOR+ or ALDHFLUOR− cells to generate tumor lysate-pulsed DCs. Mice were vaccinated with DC vaccines subcutaneously.

Flow Cytometry Analysis:

Cells from freshly harvested sc D5 tumors were stained using PE-conjugated CCR5, CCR7, CCR10, CXCR2 and FITC-conjugated CXCR4, respectively. Duplicate samples were stained using matching isotype control mAbs. Data were analyzed using an LSR machine.

CTL Cytotoxicity:

CTLs were generated from the splenocytes by anti-CD3/CD28 activation and IL-2 expansion. CTL-mediated CSC or non-CSC cytotoxicities were tested using the LDH release assay.

Antibody Production:

Spleens were harvested at the end of the experiments. Spleen B cells were activated using LPS and anti-CD40, and culture supernatants were collected and analyzed for IgG production using ELISA.

CSC Binding by Immune Supernatants:

ALDEFLUOR+ cells were incubated with the culture supernatants of spleen B cells with equal quantity of IgG. Then cells were incubated with FITC anti-mouse IgG. The binding was detected using flow cytometry.

Antibody and Complement-Mediated Cytotoxicity:

CSC lysis mediated by antibodies in culture supernatants from spleen B cells was assessed by incubation of $10^5$ ALDH$^{hi}$ CSC or ALDH$^{low}$ non-CSCs with supernatants followed by culture in the presence of rabbit complement. Viable cells were then counted after trypan blue to calculate CSC lysis: % of viable cells=viable cells counted after supernatants and complement incubation/$10^5$.

Statistical Analysis:

date was analyzed by unpaired t test. survival curves were compared using long-rank test. P values <0.05 were considered statistically significant.

Figure 1:
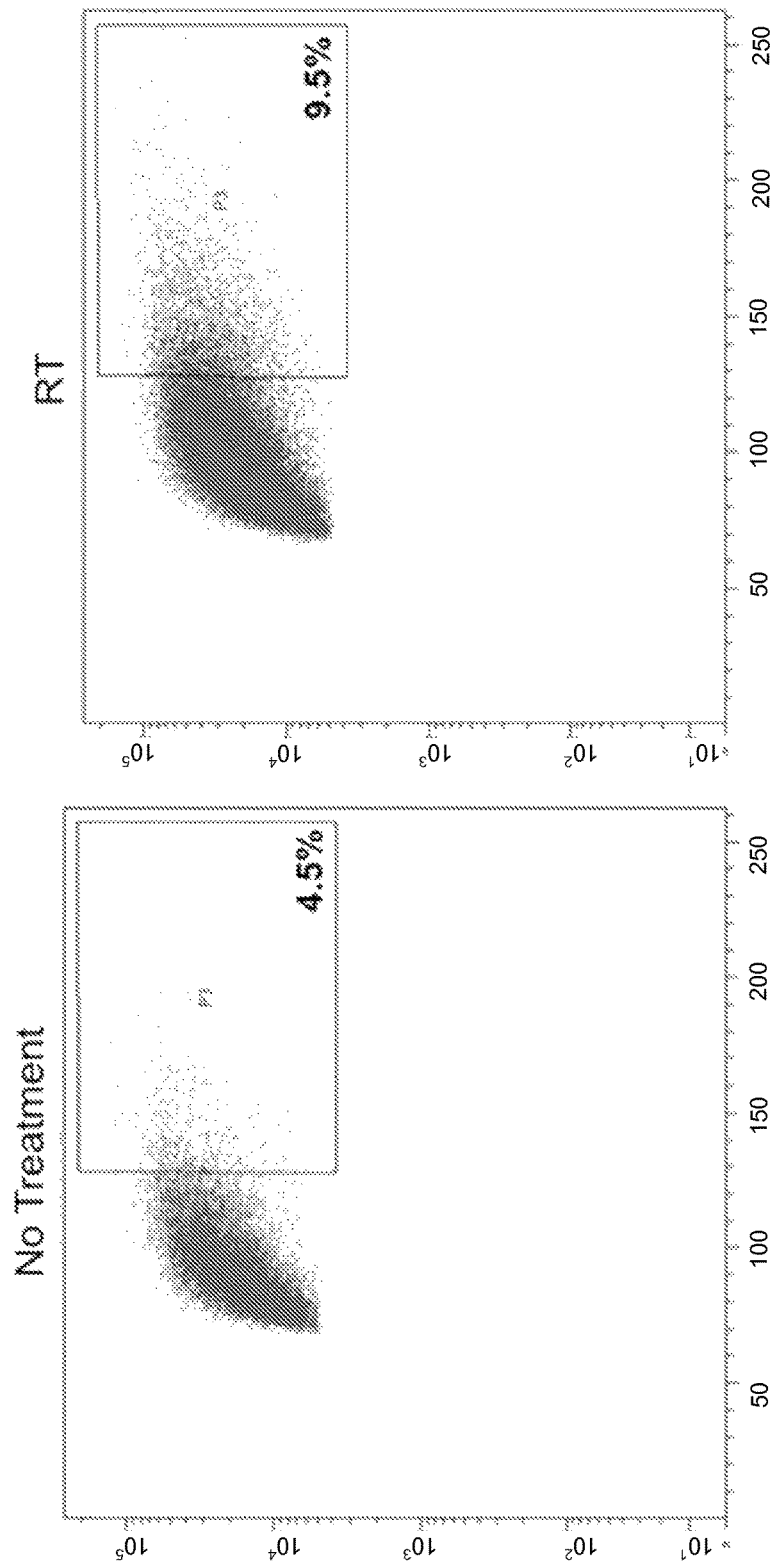
FIG. 1 provides results from Example 1 and shows that radiation therapy significantly enriched ALDH$^{high}$ CSCs in D5 tumors, going from 4.5% to 9.5% (which is greater than a 100% fold enrichment).
Figure 2:
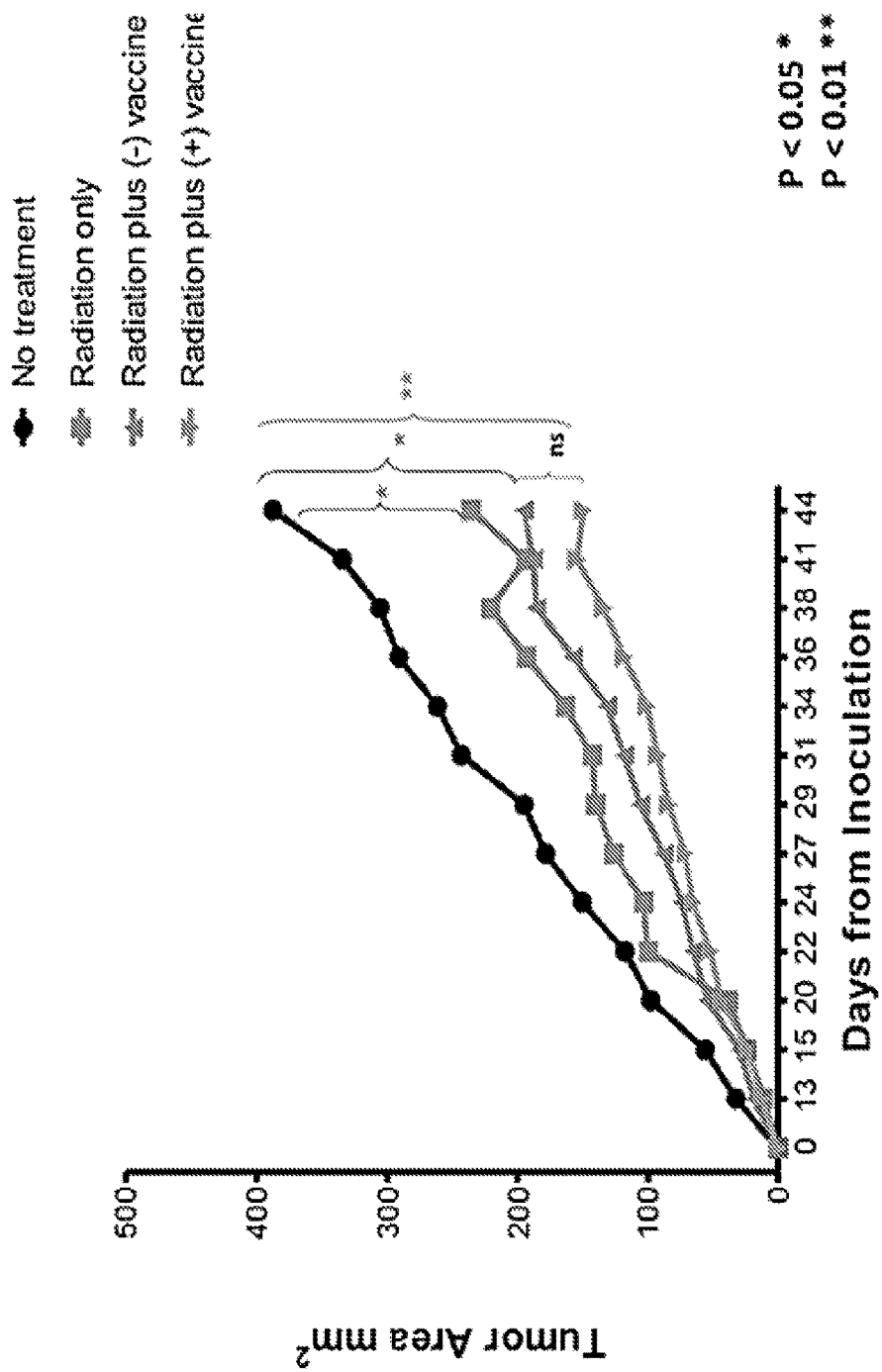
FIG. 2 provides results from Example 1 and shows subcutaneous tumor growth of D5 tumor cells in animals subjected to radiation therapy with or without cancer stem cell vaccine.
Figure 3:
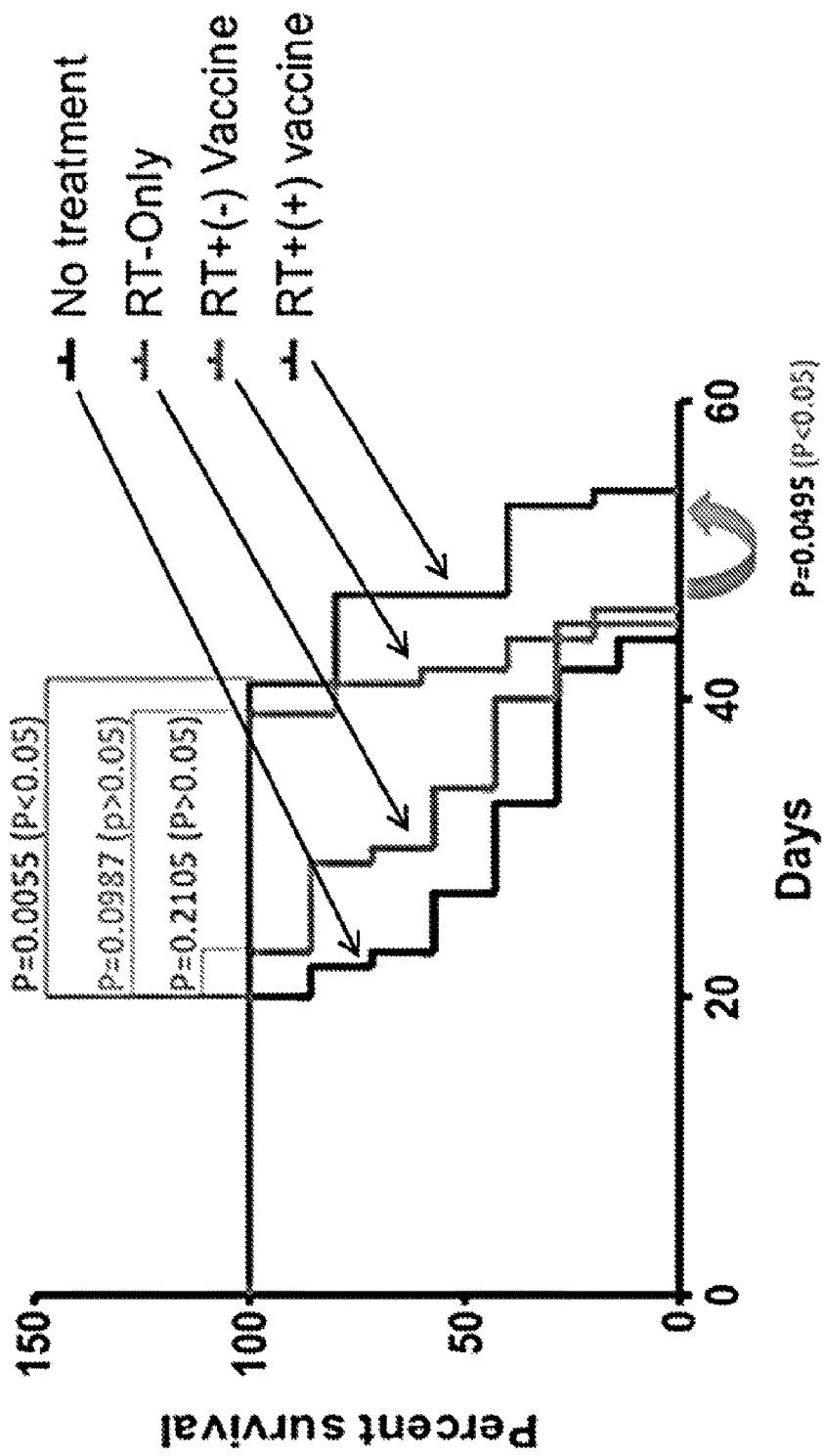
FIG. 3 provides results from Example 1 and shows the survival curves for the subcutaneous D5 tumor bearing hosts subjected to radiation therapy with or without CSC vaccine.
Figure 4:
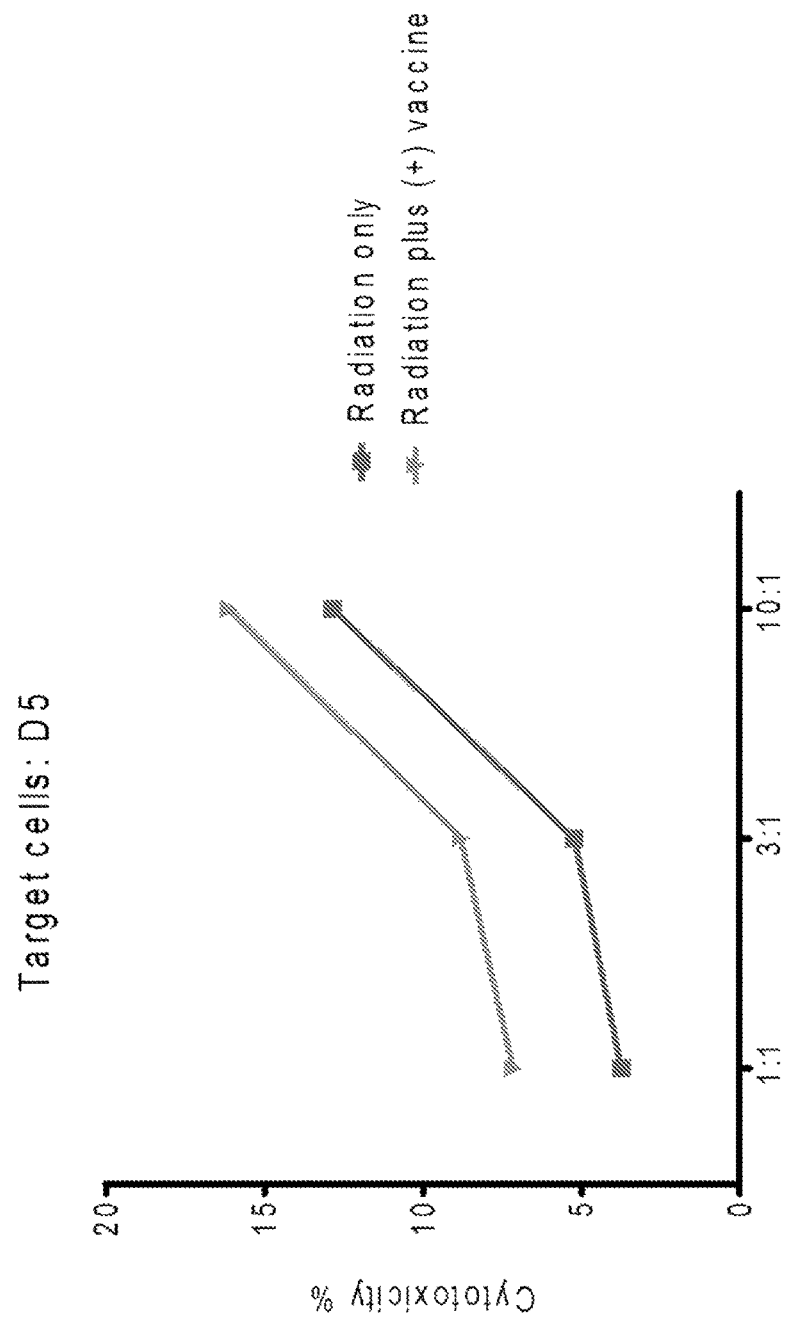
FIG. 4 provides results from Example 1 and shows cytotoxicity of unsorted D5 cells by purified and A/E spleen T cells harvested from animals subjected to radiation therapy v. radiation therapy+CSC vaccine.
Figure 5:
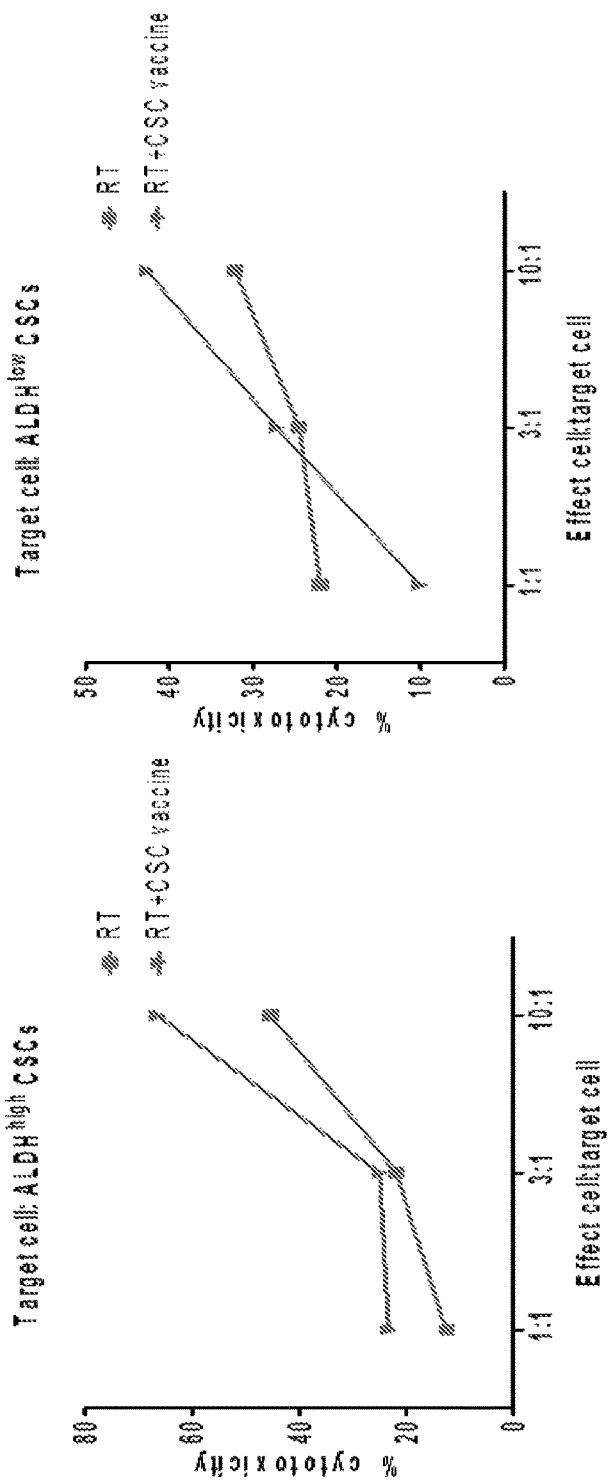
FIG. 5 provides results from Example 1 and shows the CTL of ALDH$^{high}$ vs. ALDH$^{low}$ D5 cells by purified and A/E spleen cells harvested from animals subjected to radiation therapy vs. radiation therapy+CSCS vaccine.
Figure 6:
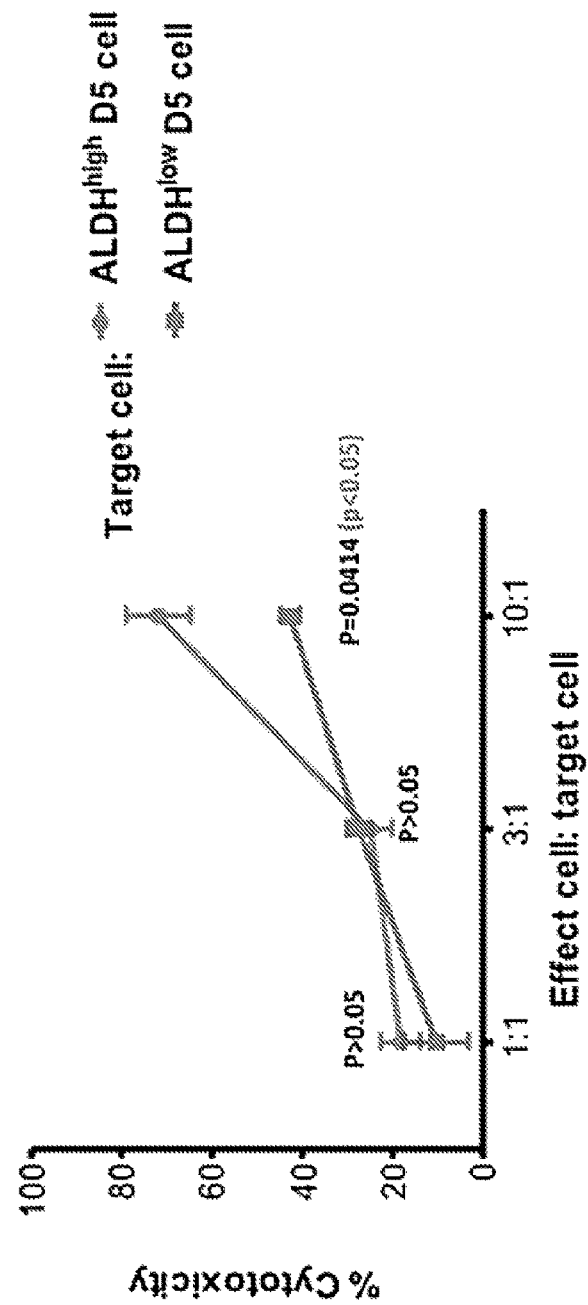
FIG. 6 provides results from Example 1 and shows CTL of ALD$^{high}$ vs. ALDH$^{low}$ D5 cells by purified and A/E spleen T cells harvested from radiation therapy+CSC vaccine. As shown in this figure, radiation therapy+CSC vaccine-primed CTLs killed more ALDH+CSCs than ALDH non-CSCs, especially when the effector to target ration was 10 to 1.
Figure 7:
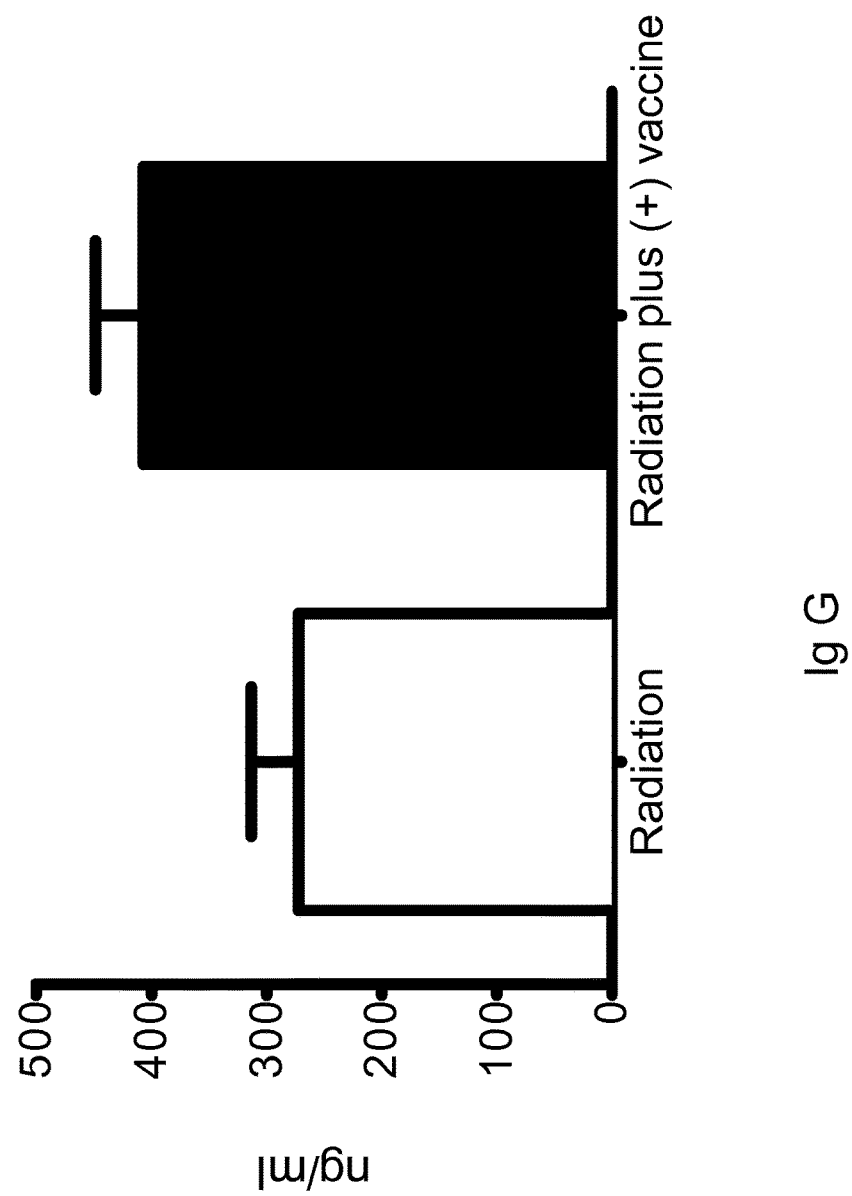
FIG. 7 provides results from Example 1 and shows IgG production by purified and LPS/anti-CD40 activated spleen B cells harvested from animals subjected to radiation therapy vs. radiation therapy+CSC vaccine.
Figure 8:
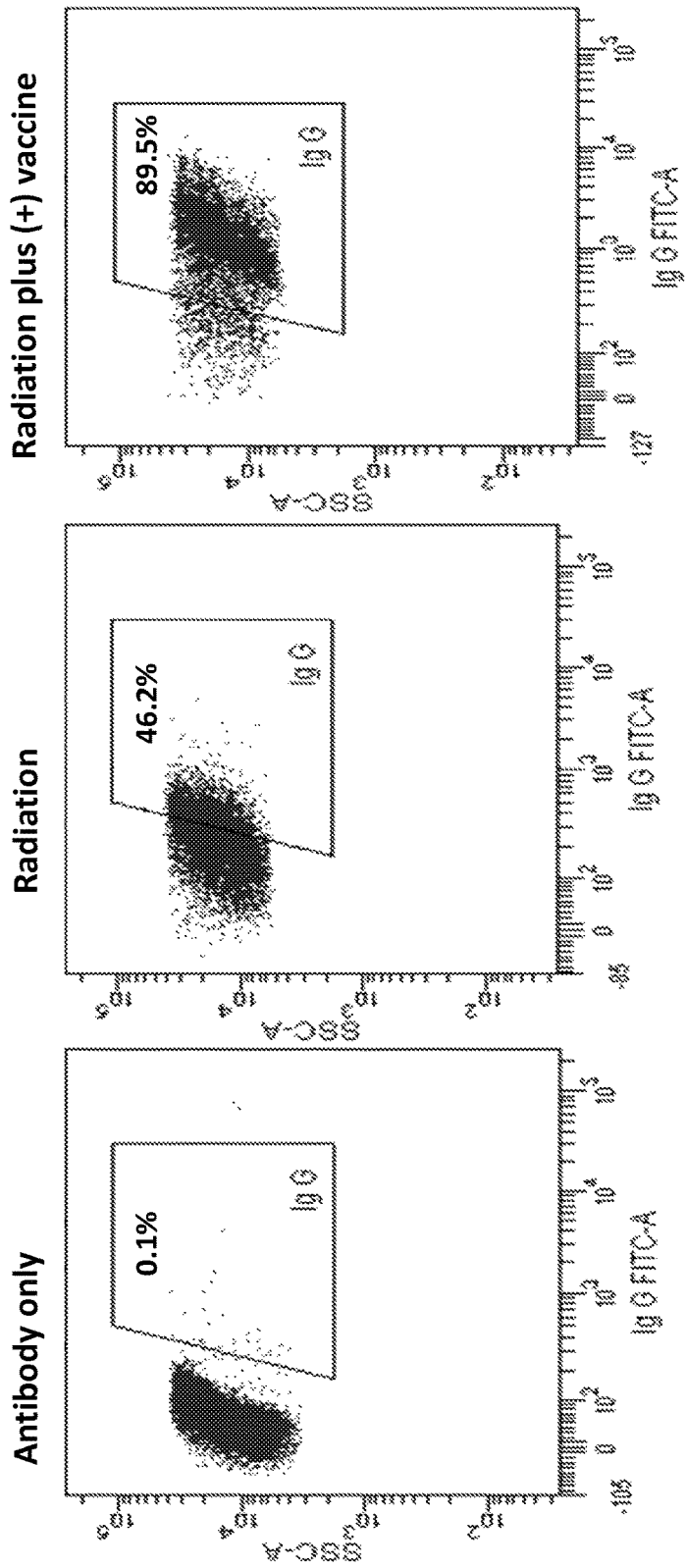
FIG. 8 provides results from Example 1 and shows culture supernatants of purified and LPS/anti-CD40 activated spleen B cells harvested from animals subjected to radiation therapy vs. radiation therapy+CSC-DC treatment bind to ALDH+D5 CSCs.
Figure 9:
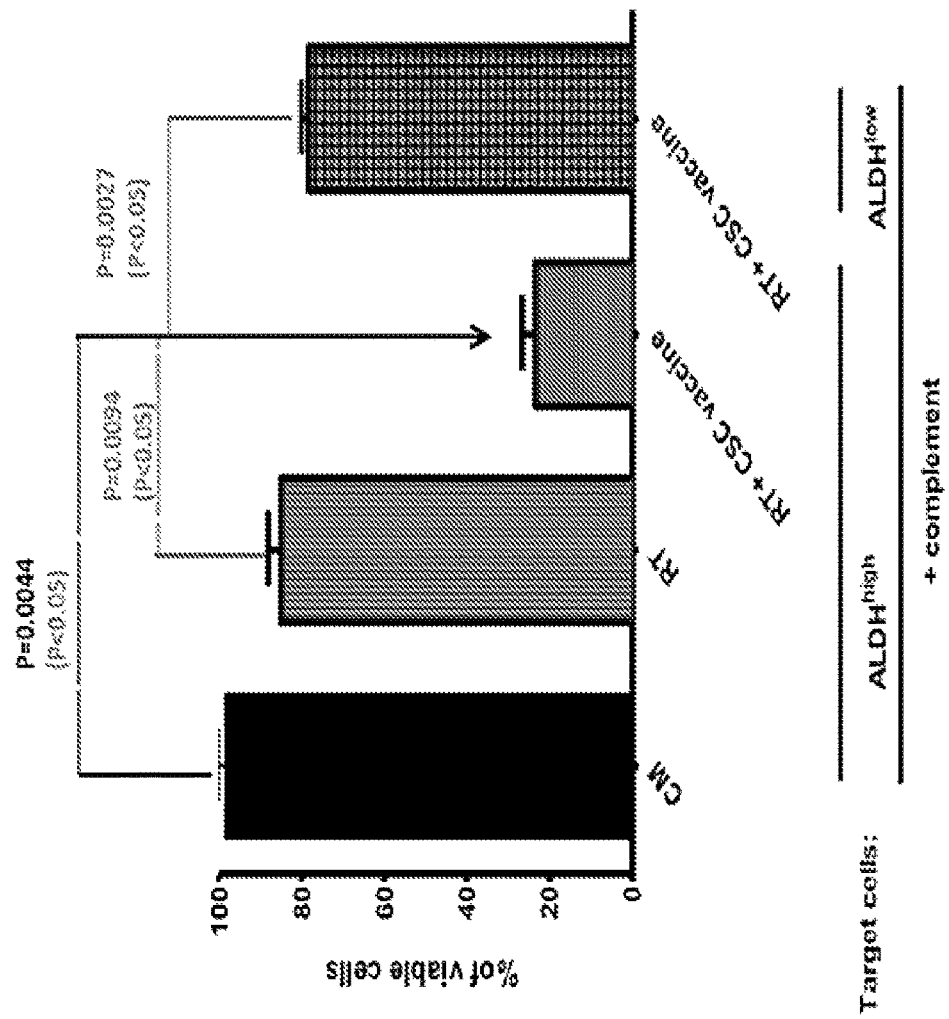
FIG. 9 provides results from Example 1 and shows results of targeting of CSCs by CSC-primed antibody and complement-dependent cytotoxicity (CDC). As shown in this figure, supernatant from radiation therapy+CSC vaccinated hosts mediated significantly more efficient D5 CSC lysis than the supernatant collected from radiation therapy-treated hosts (P=0.0094).

Results:

FIG. 1 shows that radiation therapy significantly enriched ALDH$^{high}$ CSCs in D5 tumors, going from 4.5% to 9.5% (which is greater than a 100% fold enrichment). FIG. 2 shows subcutaneous tumor growth of D5 tumor cells in animals subjected to radiation therapy with or without cancer stem cell vaccine. FIG. 2 shows the mean tumor sizes of the 4 treatment groups (no treatment, radiation only, radiation plus negative vaccine, and radiation plus positive vaccine). As can be seen in the figure, in this establish tumor model, there was no significant difference in subcutaneous tumor growth between ALDH$^{low}$ and ALDH$^{high}$ vaccine in the same setting as radiation therapy. FIG. 3 shows the survival curves for the subcutaneous D5 tumor bearing hosts subjected to radiation therapy with or without CSC vaccine. As seen in FIG. 3, there was a significant difference in the survival rate between ALDH$^{low}$ and ALDH$^{high}$ vaccine in the same setting of using radiation therapy. FIG. 4 shows cytotoxicity of unsorted D5 cells by purified and A/E spleen T cells harvested from animals subjected to radiation therapy v. radiation therapy+CSC vaccine. FIG. 5 shows the CTL of ALDH$^{high}$ vs. ALDH$^{low}$ D5 cells by purified and A/E spleen cells harvested from animals subjected to radiation therapy vs. radiation therapy+CSCS vaccine. FIG. 6 shows CTL of ALD$^{high}$ v. ALDH$^{low}$ D5 cells by purified and A/E spleen T cells harvested from radiation therapy+CSC vaccine. As shown in this figure, radiation therapy+CSC vaccine-primed CTLs killed more ALDH+CSCs than ALDH non-CSCs, especially when the effector to target ration was 10 to 1. FIG. 7 shows IgG production by purified and LPS/anti-CD40 activated spleen B cells harvested from animals subjected to radiation therapy vs. radiation therapy+CSC vaccine. In generating the data for FIG. 7, splenocytes were harvested from the animals subjected to radiation therapy with or without CSC vaccine. Enriched spleen B cells were activated with LPS/anti-CD40. The culture supernatants were then collected fro IgG detection using ELISA. Culture supernatant of B cells from radiation therapy+CSC vaccinated hosts contained higher levels of IgG. FIG. 8 shows culture supernatants of purified and LPS/anti-CD40 activated spleen B cells harvested from animals subjected to radiation therapy vs. radiation therapy+CSC-DC treatment bind to ALDH+D5 CSCs. In generating the data for FIG. 8, ALDEFLUOR+ cells were incubated with the culture supernatants of spleen B cells with equal quantity of IgG. Then cells were incubated with FITC anti-mouse IgG. Using flow cytometry, it was observed that supernatant from radiation therapy+CSC vaccinated hosts bound to D5 CSCs (89.5%) much more efficiently than the binding of the supernatant from RT-treated hosts (46.2%). FIG. 9 shows results of targeting of CSCs by CSC-primed antibody and complement-dependent cytotoxicity (CDC). As shown in this figure, supernatant from radiation therapy+CSC vaccinated hosts mediated significantly more efficient D5 CSC lysis than the supernatant collected from radiation therapy-treated hosts (P=0.0094). Such CDC mediated by CSC-primed antibody was CSC specific because supernatant from the same radiation therapy+CSC vaccinated hosts resulted in minimal lysis of ALDEFLUOR-D4 5 cells.

Figure 10:
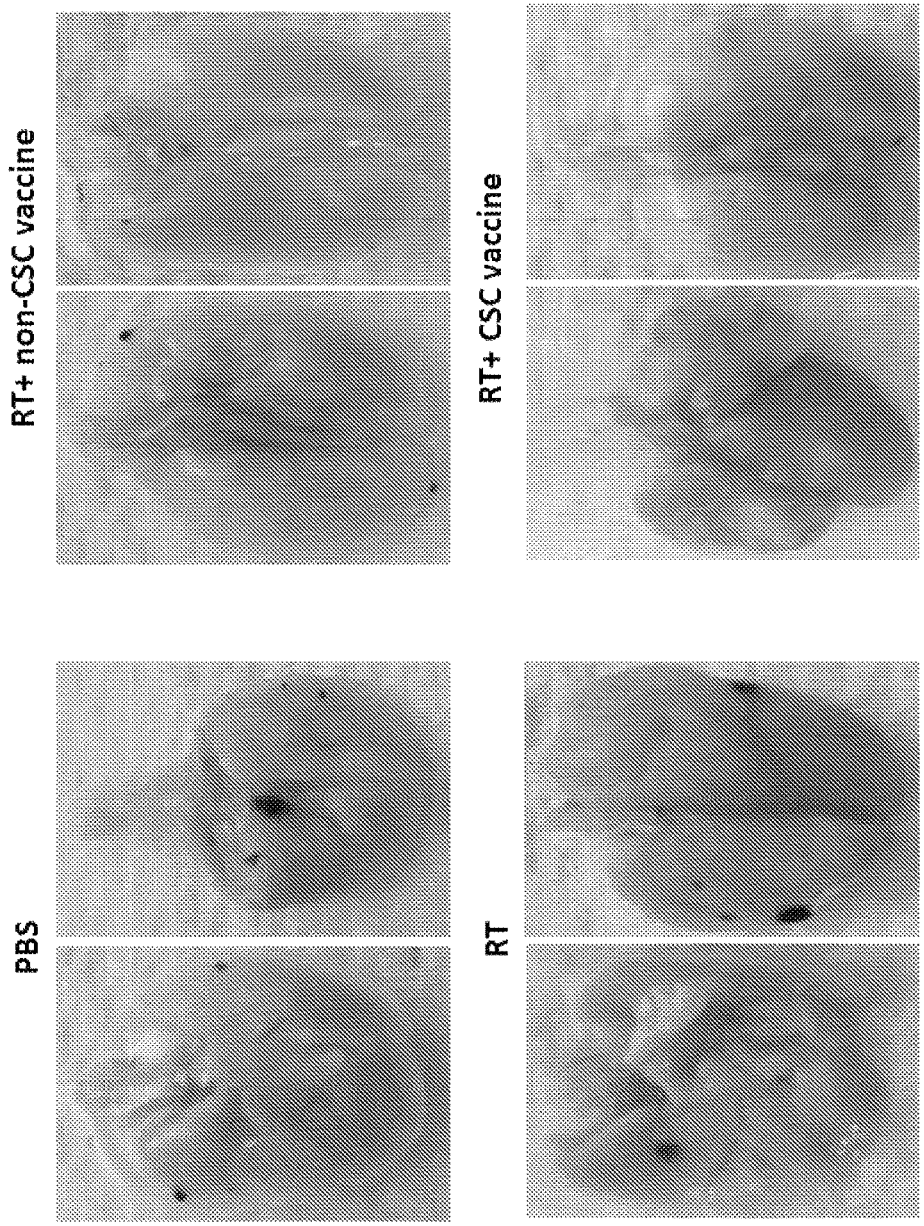
FIG. 10 provides results from Example 1 and shows ALDH$^{high}$ vaccine inhibited the metastasis of subcutaneous D5 tumor to the lung.
Figure 11:
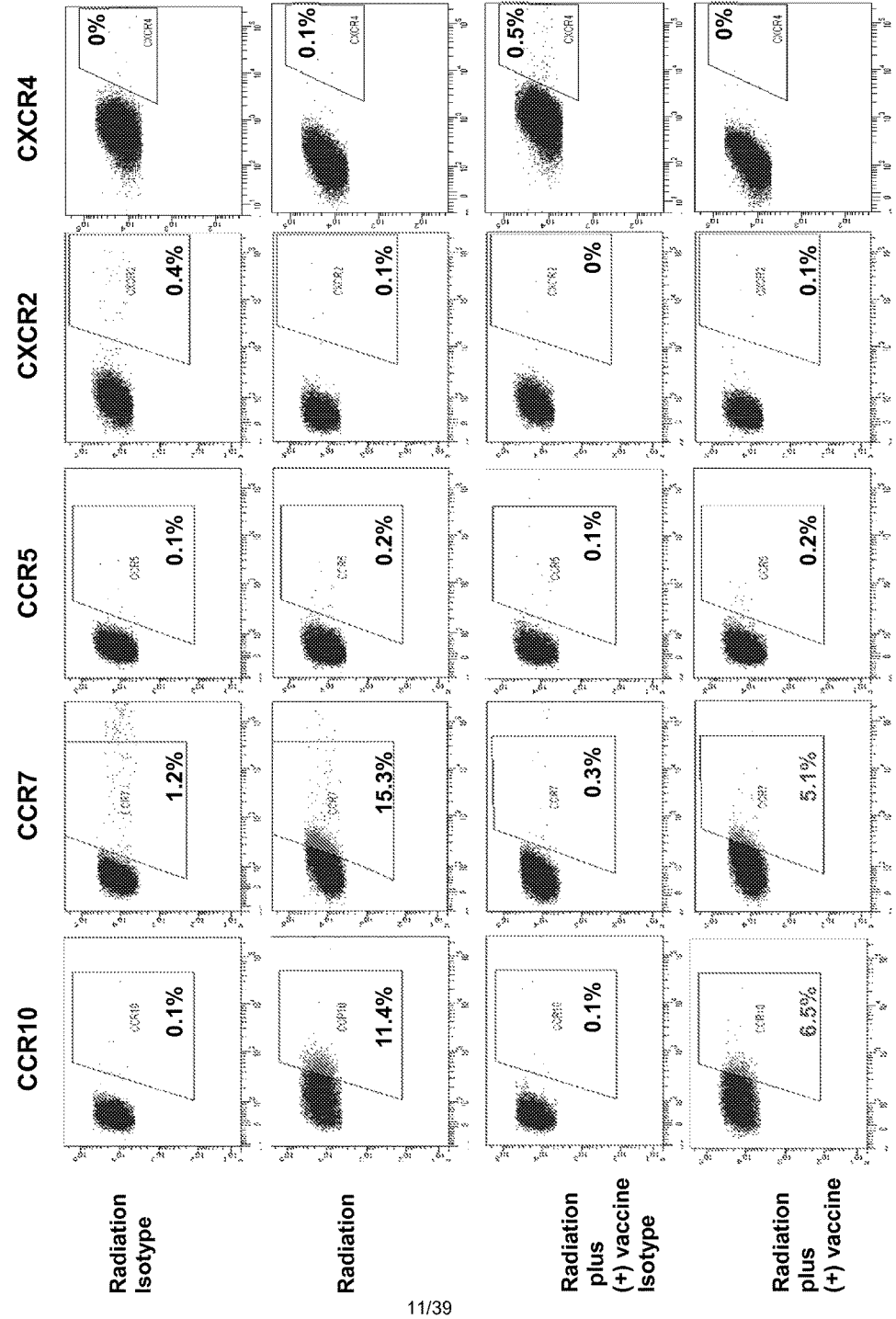
FIG. 11 provides results from Example 1 and shows chemokine receptor expression on D5 s.c. tumor from animals subjected to radiation therapy vs. radiation therapy and CSC vaccine.
Figure 12:
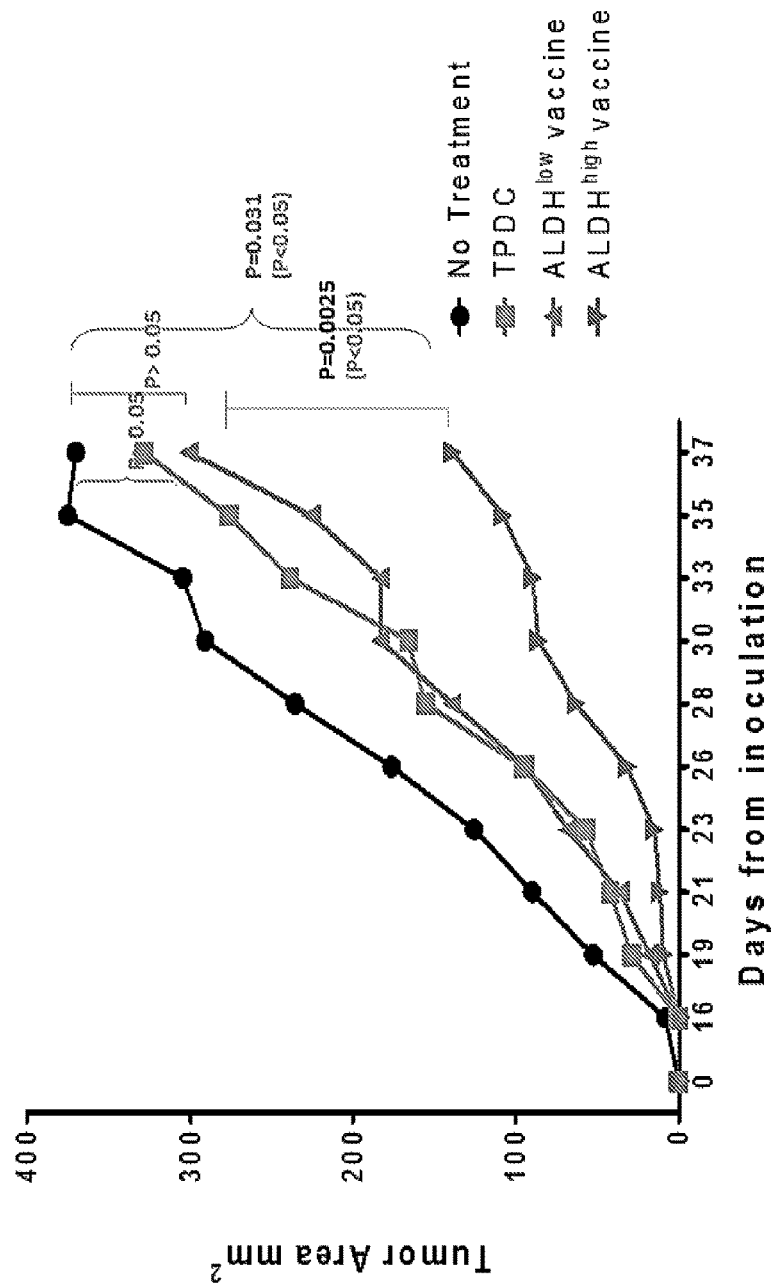
FIG. 12 provides results from Example 1 and shows CSC vaccine alone can significantly inhibit D5 tumor growth in a micrometastatic model.
Figure 13:
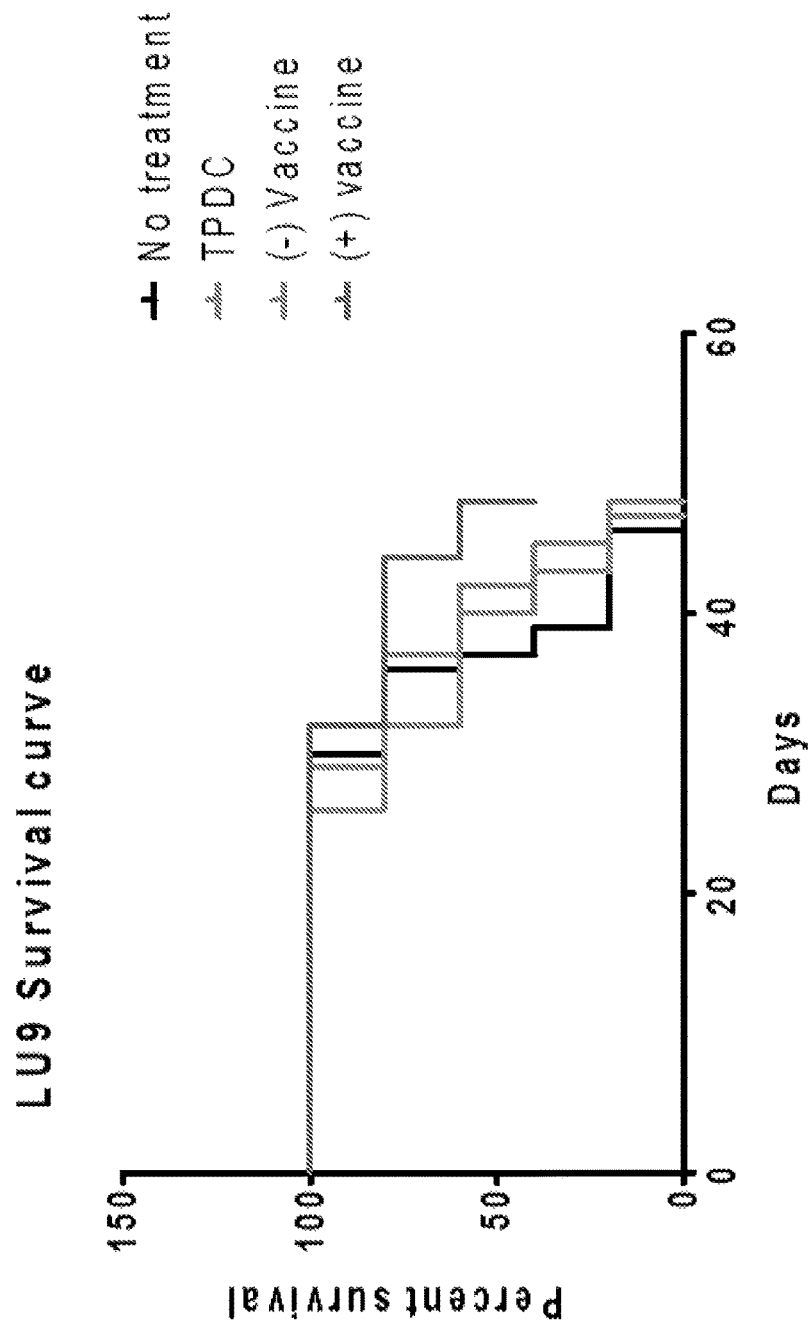
FIG. 13 provides results from Example 1 and shows a survival curve in the micrometastatic disease model which shows that a much higher percentage of vaccine treated mice survived after about 50 days compared to no treatment, TPDC, and vaccine—treated mice.

FIG. 10 shows ALDH$^{high}$ vaccine inhibited the metastasis of subcutaneous D5 tumor to the lung. FIG. 11 shows chemokine receptor expression on D5 s.c. tumor from animals subjected to radiation therapy vs. radiation therapy and CSC vaccine. As shown in this figure, radiation therapy+CSC vaccine significantly reduced the expression of CCR7 and CCR10 in s.c. D5 tumors compared to radiation therapy. FIG. 12 shows CSC vaccine alone can significantly inhibit D5 tumor growth in a micrometastatic model. FIG. 12 shows that the ALDH$^{high}$ vaccine treated mice had significantly smaller tumor size after 37 days compared to no treatment, TPDC (tumor lysate-pulsed dendritic cells), and ALDH$^{low}$ vaccine treated animals. FIG. 13 shows a survival curve in the micrometastatic disease model which shows that a much higher percentage of vaccine treated mice survived after about 50 days compared to no treatment, TPDC, and vaccine—treated mice.

The results of this Example show a number of important things. For example, it was shown that radiation therapy significantly enriched ALDH$^{high}$ CSCs in D5 (by >100%). Also for example, in the established D5 model, while there was no significant difference in s.c. tumor growth between ALDH$^{low}$ and ALDH$^{high}$ vaccine in the same setting of RT, there was significant (p<0.05) difference in the survival rate between these two groups. Other things that are shown include: 1) ALDH$^{high}$ vaccine inhibited the metastasis of sc D5 tumor to the lung; 2) RT+CSC vaccine significantly reduced the expression of CCR7 and CCR10 in s.c D5 tumors compared to RT; 3) CTLs generated from splenocytes harvested from RT+CSC vaccinated hosts killed ALDH$^{high}$ CSC more effectively than the killing of ALDH$^{low}$ non-CSCs; 4) culture supernatant of B cells from RT+CSC vaccinated hosts contained higher levels of IgG which bound to CSCs, resulting in CSC lysis in the presence of complement; and 5) in the micrometastatic D5 model, there is significant difference in sc tumor growth between ALDH$^{low}$ and ALDH$^{high}$ vaccine, so is survival.

Example 2

Combined Radiation and Cancer Stem Cell Vaccine Treatment

In this Example, the combined treatment of tumors with radiation therapy (RT) and cancer stem cell pulsed dendritic cells was tested.

Methods

Mice.

Female C57BL/6 (B6) and C3H/HeNCr MTV (C3H) mice were purchased from Jackson lab and Charles River Laboratories, respectively. All the mice were housed in specific pathogen-free condition at the University of Michigan Animal facilities. The mice used for experiments were at the age of 7-8 weeks. The University of Michigan Laboratory of Animal Medicine approved all animal protocols.

Culture of Tumor Cells.

D5 is a poorly immunogenic clone of the melanoma cell line B16 syngeneic to B6 mice, and was originally established by our laboratory. Squamous carcinoma cell line SCC7, a poorly immunogenic tumor, is syngeneic to C3H mice. The cell lines were grown in complete medium consisting of RMPI 1640 supplemented with 10% heat-inactivated fetal bovine serum, 0.05 mM 2-mercaptoethanol, 0.1 mM nonessential amino acids, 1 mM sodium pyruvate, 100 μg/mL streptomycin, 100 U/mL penicillin, 50 μg/mL gentamicin and 0.5 μg/mL fungizone.

ALDEFLUOR Assay.

The ALDEFLUOR Kit (StemCell Technologies, British Columbia, Canada) was used to isolate ALDEFLUOR$^{+}$/ALDH$^{high}$ CSCs and ALDEFLUOR$^{-}$/ALDH$^{low}$ non-CSCs from the D5 and SCC7 cells as previously described (31; herein incorporated by reference in its entirety).

Preparation of Dendritic Cell (DC) Vaccine.

To prepare tumor cell lysates, unsorted D5 or SCC7 tumor cells, sorted ALDEFLUOR$^{+}$/ALDH$^{high}$ or ALDEFLUOR/ALDH$^{low}$ cells were suspended at a concentration of 1 million cells in 1 ml complete culture medium. Cells were lysed by five rapid freeze-thaw cycles in 37° C. water bath and liquid nitrogen (49). After centrifugation, tumor cell lysates were collected and stored in liquid nitrogen for later use. Bone marrow-derived murine DCs were generated as described previously (49). Bone marrow cells from the mice were cultured in complete medium supplemented with 10 ng/mL IL-4 and 10 ng/mL GM-CSF at a concentration of 1×10$^6$ cells/ml. Fresh medium supplemented with GM-CSF and IL-4 was added on days 2 and 4. On day 5, DCs were harvested by gentle pipetting and enriched by Opti-Prep density gradient medium. Lysate of unsorted tumor cells, ALDH$^{low}$ or ALDH$^{high}$ cells was added to DCs at a 1:3 cell equivalent ratio. The DCs were then incubated at 37° C. for 24 h with 5% CO$_2$. After incubation, the unsorted tumor cell lysate-pulsed DCs (H-DC), ALDH$^{low}$ lysate-pulsed DCs (ALDH$^{low}$-DC) or ALDH$^{high}$ lysate-pulsed DCs (ALDH$^{high}$-DC, e.g. CSC-DC) will be used as vaccine as specified in the subsequent experiments. Each mouse was inoculated with 2 million DCs per vaccine.

Tumor Growth and Treatment Protocols.

In micrometastatic tumor model, B6 or C3H mice were inoculated subcutaneously with 2,500 D5 cells or 5,000 SCC7 cells respectively. The 1st vaccine was administered 24 hours after tumor inoculation for treatment, followed by a 2nd vaccine on day 8. Tumor-bearing C3H mice were administered with a 3rd vaccine on day 15. In the established tumor model, B6 or C3H mice were inoculated s.c. with 0.05 million D5 cells or 0.5 million SCC7 cells respectively on day 0. The mice were treated with localized radiation therapy (RT) on day 5 and day 6 followed by the 1st DC vaccine on day 7. The combined RT+vaccine treatment was repeated on day 12, 13, 14 and 19, 20, 21 respectively. Thus, the RT was delivered 6 times, which were on days 5, 6, 12, 13, 19 and 20 with a total dose of 51 Gy (8.5 Gy×6), while vaccines were administrated 3 times, 1 week apart, which were on days 7, 14 and 21. Each experimental group contained 5-8 mice. Tumor volumes were measured 3 times per week. The long and short diameters of tumor mass were measured and the tumor volume was calculated as: tumor volume=(width2*length)/2. Survival was monitored and recorded as the percentage of surviving mice after tumor inoculation.

Hematoxylin and Eosin (H&E) Staining for Histologic Analysis.

At the end of the experiments, the lungs were harvested and fixed with 10% formalin, paraffin embedded and stained with H&E to observe the histo-pathological alterations. The slides were observed under the microscope with 100× magnification.

Measurement of Chemokine Receptor Expression on Tumor Cells.

Freshly harvested primary subcutaneous tumors were disaggregated into single cell suspensions using enzymatic digestion as previously described (86). After counting, the tumor cells were incubated with PE conjugated antibodies against CCR7 and CCR10 or isotype controls for 30 minutes at 4° C. Then the cells were resuspended in 2% formalin. Flow cytometry analysis was carried out with a BD LSR cytometer.

Detection of Chemokine Expression in Lung Tissues.

The mRNA expression levels of chemokine CCL21, CCL27 or CCL28 in lung tissues were analyzed using real time quantitative PCR (qRT-PCR). The preparations of the total RNA and cDNA were previously described (87). The relative mRNA levels of various chemokines and GAPDH (as an internal control) were quantified by SYBR-GREEN master mix (Invitrogen Life Technology, Carlsbad, Calif.). The relative expression levels of the chemokines were then normalized to the geometric mean of the internal control gene (GAPDH) by using the comparative Ct method (2-ΔΔCT). The data was expressed as the relative fold changed.

Purification and Culture of B Cells.

To study CSC vaccine-induced anti-CSC humoral response, spleens were harvested from animals subjected to various treatments at the end of the experiments. Spleen B cells were purified using CD19 microbeads (Miltenyi Biotec, Bergisch Gladbach, Germany) and activated 5 days in complete culture medium supplemented with lipopolysaccharide (LPS), anti-CD40 (FGK45) and IL-2. The culture supernatants were collected and stored at −20° C. for future experiments.

CSC Binding by Immune Supernatant.

Sorted ALDH$^{low}$ or ALDH$^{high}$ D5 cells were incubated with the immune supernatants collected from the cultured B cells with equal quantity of IgG followed by incubation with the 2nd antibody FITC-conjugated anti-mouse IgG. The binding of supernatant antibody to ALDH$^{low}$ vs. ALDH$^{high}$ D5 cells was assessed using flow cytometry (31).

Antibody and Complement Mediated Cytotoxicity.

Antibody and complement-mediated cytotoxicity against CSCs was described previously (31). Briefly, $10^5$ viable ALDH$^{high}$ or ALDH$^{low}$ D5 cells were incubated with immune supernatants collected from the culture of purified and activated spleen B cells. Then the cells were incubated with rabbit complement for another 1 hour. The trypan blue staining was used to assess the cell lysis which was expressed as: % viable cells=the number of viable cells after immune supernatant and complement incubation/$10^5$. Each experiment was repeated at least 3 times.

Statistics.

Data were analyzed using GraphPad Prism 6 (GraphPad software). Survival analysis was determined by the log-rank test. Analysis for the presence of lung metastasis was performed using the Fisher exact test. Other data were evaluated by unpaired Student's t test (2 cohorts) or one-way analysis of variance (ANOVA) (>2 cohorts). A two-tailed P value <0.05 was considered as significant.

Results

1. CSC-DC Vaccine Confers Significant Therapeutic Efficacy in the Treatment of Micrometastatic Disease To evaluate the CSC-DC vaccine in a therapeutic model, it is generally accepted that tumor vaccines will have their greatest effect in the setting of micrometastatic disease. Two tumor models were used to test the therapeutic efficacy of the CSC-DC vaccine in this setting.

Using the murine D5 melanoma tumor model, normal syngeneic B6 mice were inoculated with 2,500 D5 cells s.c. followed by vaccination 24 hours later (day 1) with DCs pulsed with the lysate of ALDH$^{high}$ D5 CSCs (CSC-DC), ALDH$^{low}$ D5 cell lysate (ALDH$^{low}$-DC), heterogeneous unsorted D5 cell lysate (H-DC), or with PBS, respectively. The treatment was repeated on day 8. Tumor sizes were monitored 3 times a week. As showed in FIG. 1A, no significant differences in the tumor growth were observed among PBS-treated control, H-DC or ALDH$^{low}$-DC treated mice (P>0.05). However, CSC-DC vaccine treatment resulted in significant inhibition of tumor growth compared with any of these control groups (FIG. 1A, P<0.05 vs. all other groups). In addition, the CSC-DC treated mice survived significantly longer than mice subjected to all control treatments (FIG. 1B, P<0.01 CSC-DC vs. all other groups).

To verify these results, similar experiments were performed using a second tumor model, squamous cell carcinoma (SCC7), syngeneic to a different immunocompetent host (C3H mice). Normal C3H mice were inoculated with 5,000 SCC7 cells s.c. followed by vaccination 24 hours later (day 1) with DCs pulsed with the lysate of ALDH$^{high}$ SCC7 CSCs (CSC-DC), ALDH$^{low}$ SCC7 cell lysate (ALDH$^{low}$-DC), heterogeneous unsorted SCC7 cell lysate (H-DC), or with PBS, respectively. The treatment was repeated on day 8 and day 15. The tumor growth curves in FIG. 1C showed minimum therapeutic efficacy by ALDH$^{low}$-DC or H-DC. However, the tumor volumes of the CSC-DC vaccine-treated mice were significantly smaller than those of PBS-treated control (P=0.0048), H-DC vaccinated hosts (P=0.0378) or ALDH$^{low}$-DC vaccinated animals (P=0.0255). Furthermore, CSC-DC vaccine significantly prolonged the overall survival of the s.c SCC7-bearing mice (FIG. 1D, P<0.02 vs. all other groups).

Together, these data indicate that treatment of s.c tumor-bearing mice in a micrometastatic disease setting with CSC-DC vaccine results in significant antitumor immunity, which was evident by inhibited s.c. tumor growth and prolonged survival of the tumor-bearing hosts. This was observed in two histologically different tumor models in two genetically distinct syngeneic immunocompetent hosts tested in this example.

2. Therapeutic Efficacy of CSC-DC Vaccine in the Treatment of Established Disease The particular micrometastatic tumor model used in the above experiments has relevance in the design of future clinical trials because resection of primary tumor is associated with high rate of local relapse and death from recurrent disease (51, 52). It is now well-accepted that local disease relapse is due to the presence of residual CSCs after the primary tumor removal (53). Hence, DC vaccine approaches that target CSCs at a micrometasatic level may prevent the cancer from relapsing in the adjuvant setting. However, in patients with locally advanced cancers, radiation therapy (RT) and/or chemotherapy may be the only option which can be offered. Therefore, the therapeutic efficacy of CSC-DC vaccine in the treatment of established disease was examined.

Figure 14:
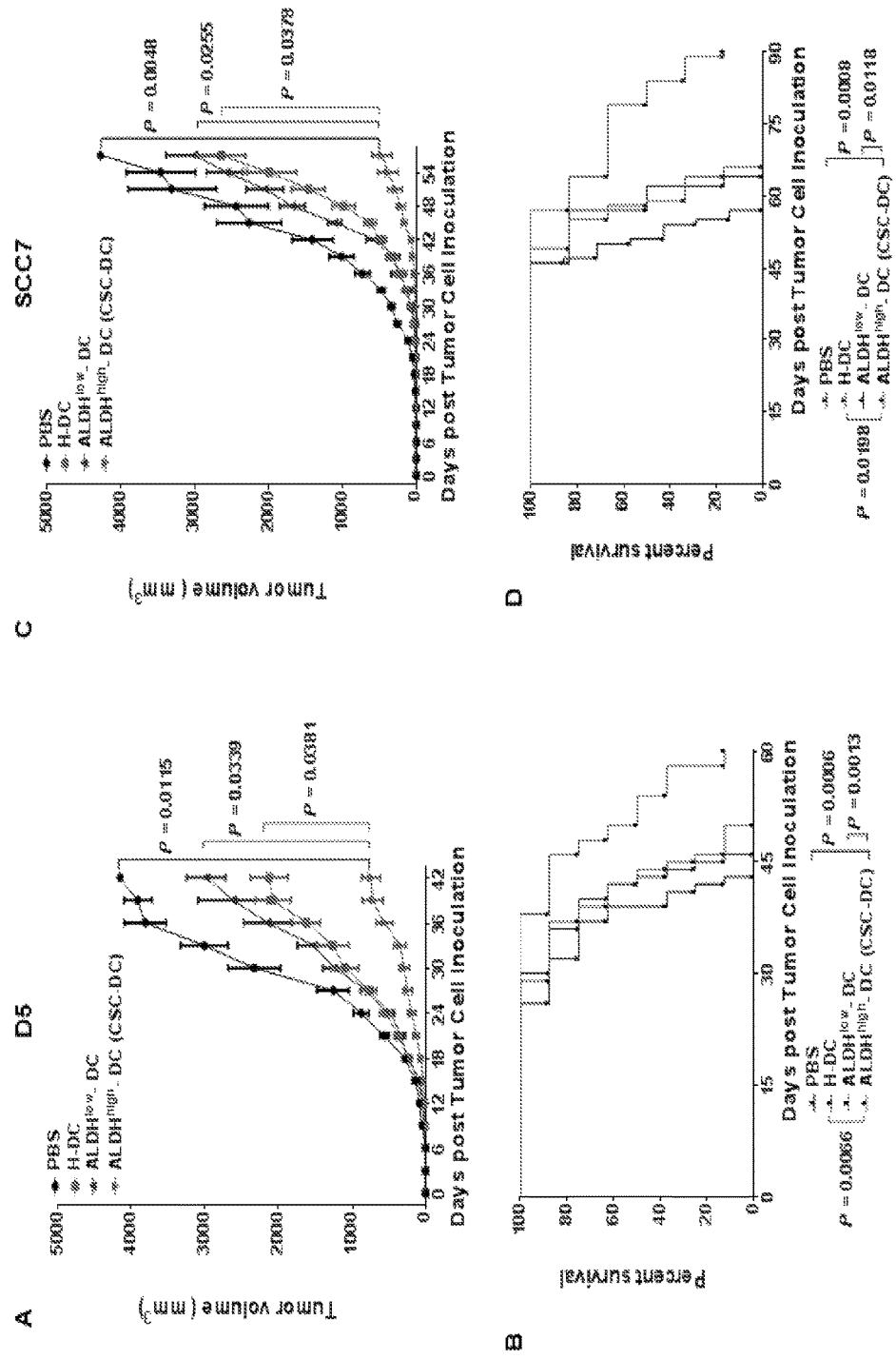
FIG. 14 shows that CSC-DC vaccine induced a significant antitumor effect in micrometastatic D5 melanoma and SCC7 squamous cell carcinoma models. (A, C) CSC-DC vaccination significantly inhibited subcutaneous tumor growth. 24 hours after s.c inoculation of D5 (FIG. 14A) or SCC7 (FIG. 14C) cells, animals were treated with different vaccines as indicated, and the treatment was repeated one week later. Tumor volumes (mean±SEM) are shown. (B, D) CSC-DC vaccine significantly prolonged the survival of s.c D5-bearing mice (FIG. 14B) and SCC7-bearing mice (FIG. 14D). In 14D, the median survival for the CSC-DC vaccine-treated mice was 71 days, which demonstrated a 25-day survival advantage over untreated (PBS) group. Whereas, the H-DC or ALDH$^{low}$-DC vaccines exerted only a 2-3 day survival advantage over the PBS control. Data are representative of 3 independent experiments performed for D5 (14A, 14B), and data was repeated in a second experiment for SCC7 (14C, 14D).
Figure 15:
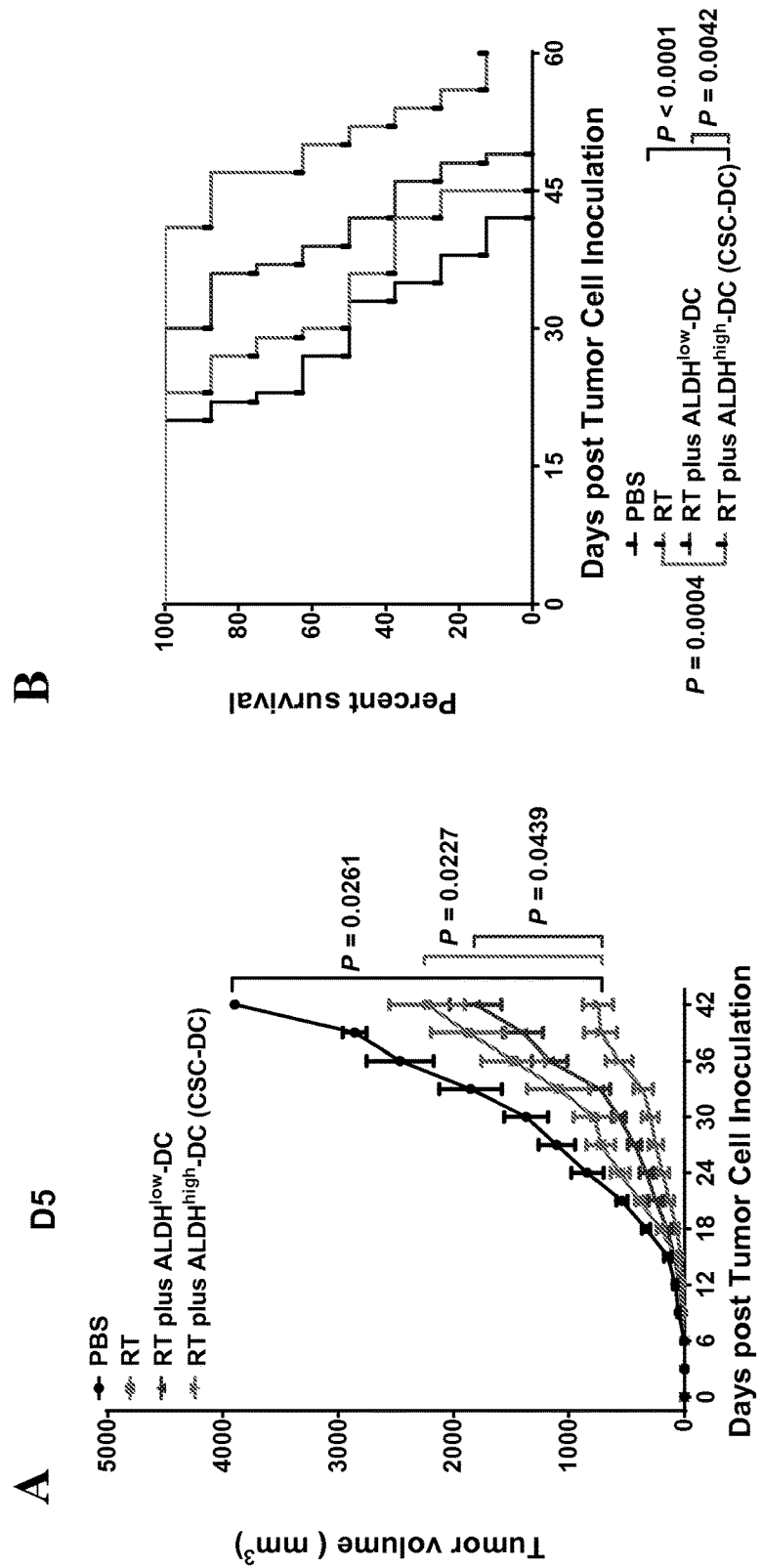
FIG. 15 shows that the CSC-DC vaccine significantly augments the therapeutic efficacy of local tumor radiation therapy (RT) in the established D5 and SCC7 models. (A, C) Mice bearing 5-day established D5 sc. tumor (FIG. 15A) or SCC7 sc. tumor (FIG. 15C) were subjected to treatment with PBS, RT alone, RT plus ALDH$^{low}$-DC or RT plus ALDH$^{high}$-DC (CSC-DC) vaccine as indicated. Treatment was repeated on day 12 and 19 respectively. Tumor volumes (mean±SEM) are shown. (B, D) Survival curves of D5-bearing mice (FIG. 15B) and SCC7-bearing mice (FIG. 15D) subjected to PBS, RT alone, RT plus ALDH$^{low}$-DC or RT plus ALDH$^{high}$-DC (CSC-DC) vaccine respectively. Data are representative of 3 independent experiments performed for D5 (15A, 15B), and data was repeated in a second experiment for SCC7 (15C, 15D).
Figure 15:
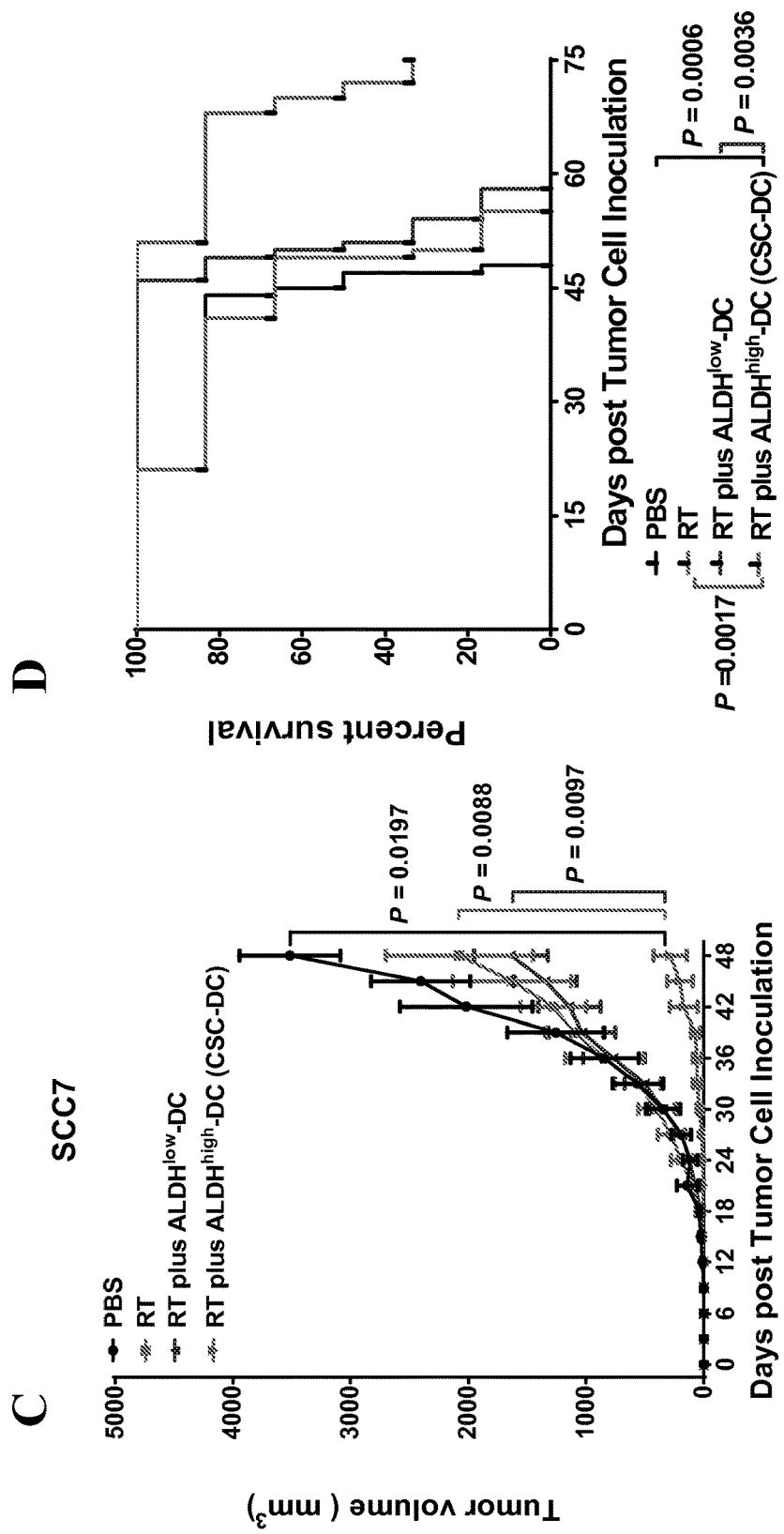

It was previously observed that localized RT could reduce the tumor volume of established D5 subcutaneous tumors. It was found that the ALDH$^{high}$ CSCs population was enriched in the residual tumors after RT treatments, going from 1.5% to 18.7%. These data indicated that CSCs are resistant to localized RT. It was hypothesized that CSC-based vaccine as an additional therapy can augment the therapeutic efficacy of RT in an established tumor model. To test this hypothesis, 50,000 D5 tumor cells were inoculated s.c. into B6 mice to establish s.c. tumors. On day 5, 6, 7, tumor-bearing mice were treated with the $1^{st}$ RT, $2^{nd}$ RT and $1^{st}$ DC vaccination, respectively. The treatment was repeated on day 12, 13, 14 with the $3^{rd}$ RT, $4^{th}$ RT and $2^{nd}$ DC vaccination, respectively, and repeated again on day 19, 20, 21 with the $5^{th}$ RT, $6^{th}$ RT and $3^{rd}$ DC vaccination, respectively. Each vaccination included ALDH$^{high}$-DC (CSC-DC) vs. ALDH$^{low}$-DC. These DCs were prepared as in FIG. 14A, B. As revealed in FIG. 15A, the combination of RT and CSC-DC vaccine significantly decreased tumor burden compared with PBS treatment (P=0.0261); RT only (P=0.0227) or RT plus ALDH$^{low}$-DC vaccination (P=0.0439). The survival of RT plus CSC-DC vaccinated hosts was significant longer than non-treated (PBS) mice (P<0.001), RT alone treated mice (P=0.0004) or RT plus ALDH$^{low}$-DC vaccinated mice (P=0.0042) (FIG. 15B).

Similar experiments were conducted on the established SCC7 tumors in the C3H hosts. Day 5 SCC7 s.c. tumors were treated with localized RT followed by CSC-DC vaccine in an identical schedule to that used for the treatment of established D5 tumors in the B6 mice. Therapeutic efficacy was compared between the groups which were both subjected to radiotherapy and received equal numbers of DCs pulsed with the lysate of ALDH$^{high}$ SCC7 CSCs (CSC-DC) vs. ALDH$^{low}$ SCC7 cells (ALDH$^{low}$-DC) prepared as in FIG. 14C, D. As shown in FIG. 15C, growth of subcutaneous tumors in the mice subjected to RT plus ALDH$^{high}$-DC (CSC-DC) vaccine was significantly inhibited compared with those subjected to other treatments (P<0.02 vs. all other groups). Overall survival showed that RT only and RT plus ALDH$^{low}$-DC both failed to prolong the survival of the mice substantially. However, RT plus ALDH$^{high}$-DC vaccine significantly improved survival (FIG. 15D, P<0.005 vs. all other groups). Of note, mice treated with RT plus ALDH$^{high}$-DC vaccine had a 20.5-day survival advantage over the RT plus ALDH$^{low}$-DC vaccinated mice (P=0.0036). These results demonstrated that while RT alone and RT plus ALDH$^{low}$-DC vaccine failed to mediate tumor regression, RT with subsequent ALDH$^{high}$ CSC-DC vaccination significantly augmented the therapeutic efficacy as evident by significantly inhibited subcutaneous tumor growth as well as improved overall survival. Collectively, the in vivo antitumor immunity of CSC-DC vaccine against established tumors in the setting of local tumor irradiation was observed in both melanoma D5 and squamous cell carcinoma SCC7 tumor models.

3. CSC-DC Vaccination Prevents Pulmonary Metastasis by Significantly Down-Regulating the Expression of CCR7 and CCR10 on Tumor Cells and Reducing the Production of CCL27, CCL28 in Lung Tissues The in vivo studies demonstrated significant therapeutic efficacy of CSC-DC vaccines in the treatment of micrometastatic disease as well as established disease following localized radiation therapy. Such CSC-DC vaccine-conferred antitumor immunity was observed in both melanomas D5 and squamous cell carcinoma SCC7 models, and was documented as significantly inhibited local tumor growth and prolonged overall survival. Distant metastases of primary tumors to multiple organs contribute largely to the tumor progression, and are the main causes for the death of tumor-bearing hosts (54, 55). Leung reported that distant metastasis confers a 5-year survival of only 5-10% and a median survival of 6-10 months of melanoma patients (56). This poor prognosis in part reflects metastatic melanoma's unique tumor biology, which distinguishes it from other advanced visceral solid-organ neoplasms. Advanced melanoma spreads in an unpredictable fashion with widespread metastasis to any organ site but often to skin, lung, brain, liver, or small bowel (56). The advanced metastatic melanoma is almost uniformly fatal (57, 58). Similarly, a usual feature of head and neck squamous cell carcinoma is distant metastases, the incidence of which at presentation varies from 4.2% to 23.8%, while at autopsy incidences up to 57% have been reported (59). Distant metastases as well as local and regional recurrences is the leading cause of treatment failure and death of patients with head and neck squamous cell carcinoma (60). Thus, early detection of distant metastases has significant therapeutic and prognostic implications, and is critical for prognostication and for the choice of treatment in patients with melanoma as well as head and neck squamous cell cancer.

Figure 16:
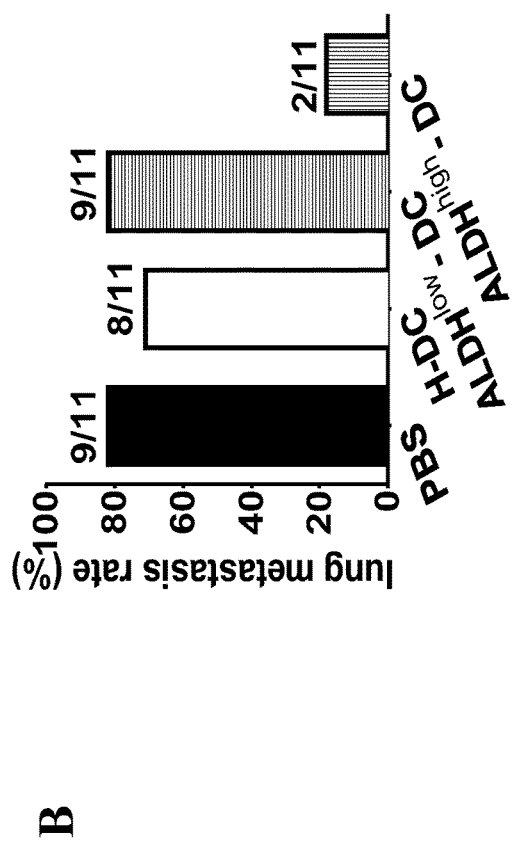
FIG. 16 shows that CSC-DC vaccination prevented the lung metastasis in the micrometastatic D5 model.
Figure 16:
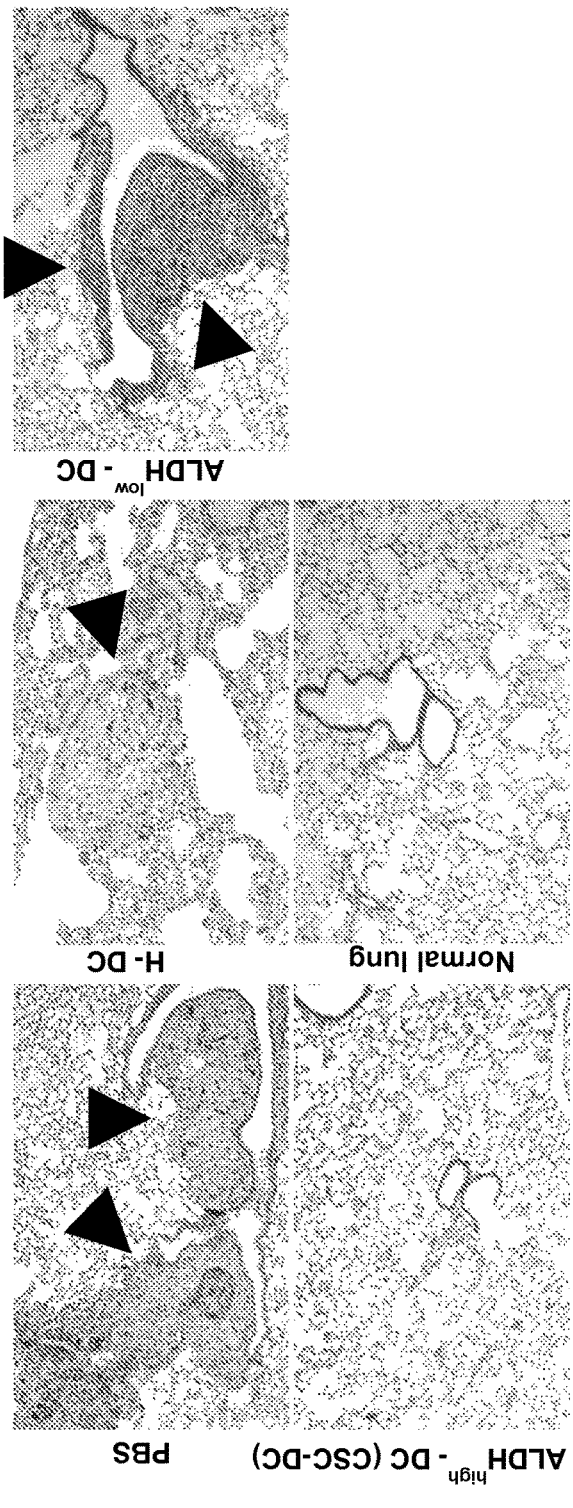

While the present invention is not limited to any particular mechanism, and an understanding of the mechanism is not necessary to practice the present invention, it may be that one of the mechanisms underlying ALDH$^{high}$ CSC-DC vaccine-conferred therapeutic efficacy vs. ALDH$^{low}$ DC or H-DC may involve CSC-DC-induced effect on the inhibition of tumor metastasis. To test this hypothesis, lungs were harvested at the end of the experiments and examined the D5 metastatic lung tumor burden. In the micrometastatic D5 model, ALDH$^{high}$-DC vaccine significantly inhibited tumor metastasis to the lung compared with PBS, H-DC and ALDH$^{low}$-DC vaccine treatments (P<0.05, FIG. 16A). There were only 2 out of 11 total mice developed lung metastasis after ALDH$^{high}$-DC vaccination, while 9 mice treated with PBS or ALDH$^{low}$-DC; 8 mice treated with H-DC developed lung metastasis (FIG. 16B). H&E staining was performed to verify the lung metastasis. The representative lung metastasis graphs are shown in FIG. 16C. The image of lung tissue harvested from normal B6 mice served as a control. Mice subjected to PBS treatment, H-DC or ALDH$^{low}$-DC vaccine all showed large tumor lesions. In contrast, there were no tumor lesions detected in the lungs harvested from ALDH$^{high}$ CSC-DC vaccinated hosts (FIG. 16C).

Figure 17:
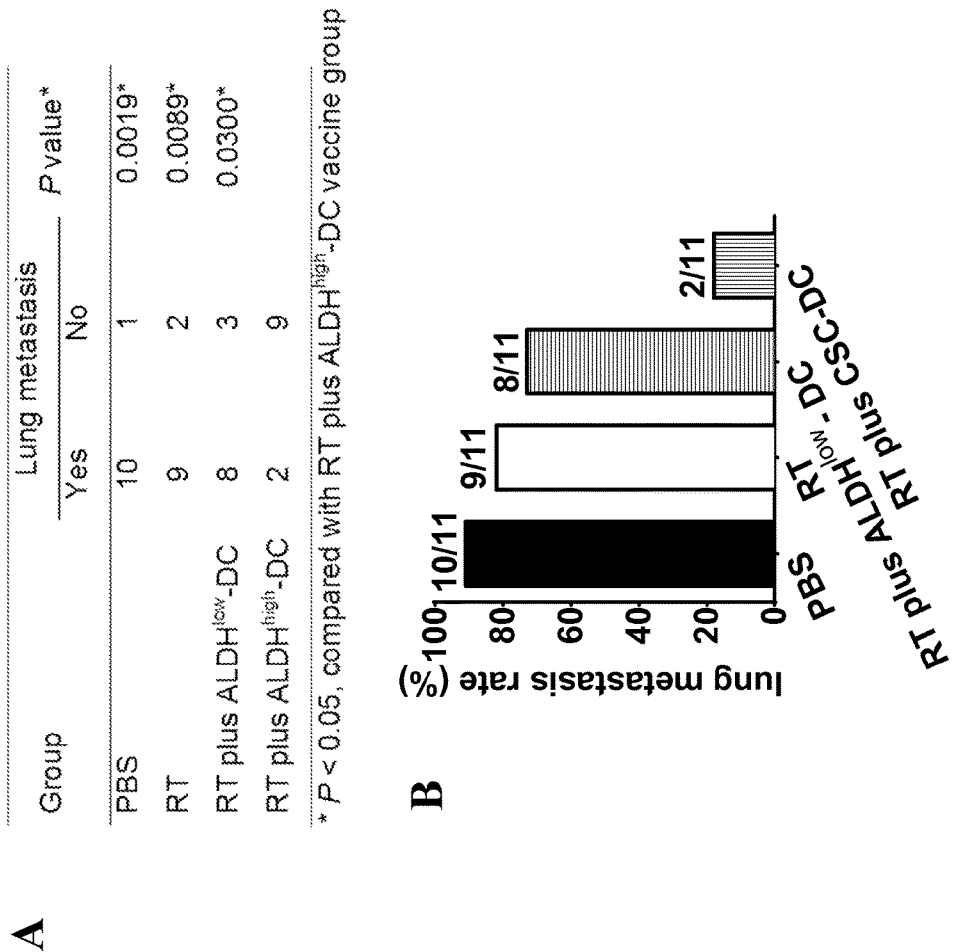
FIG. 17 shows local tumor radiation therapy (RT) followed by CSC-DC vaccination significantly inhibited the lung metastasis in the established D5 model.
Figure 17:
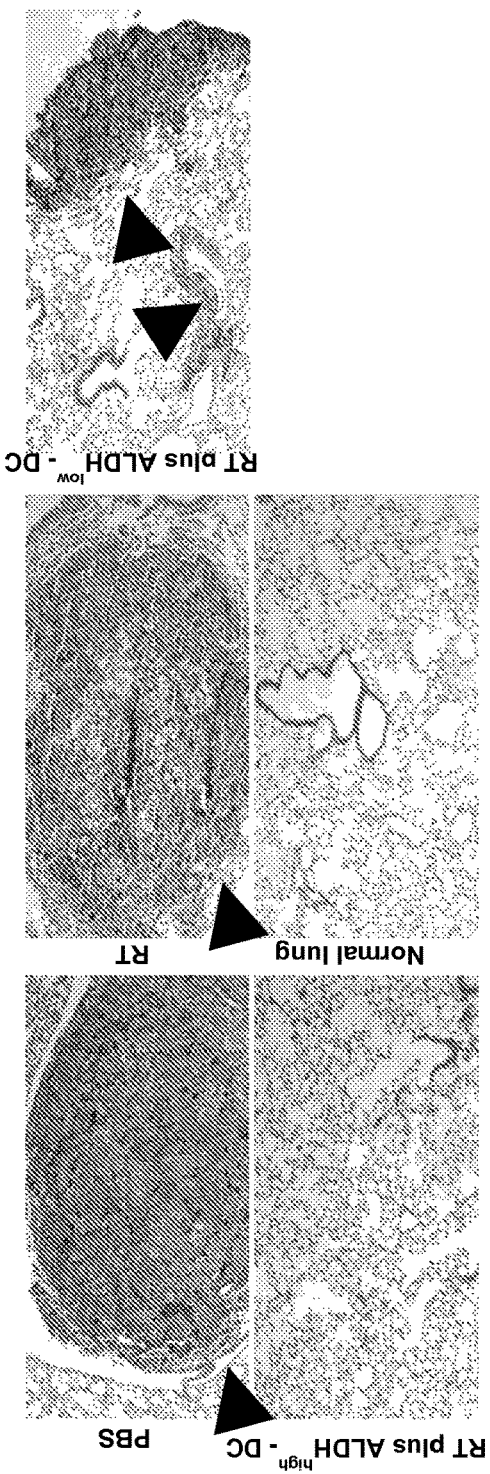

Lungs were also harvested at the end of the experiments in the treatment of established disease, and the burden of D5 tumor metastasis to the lung was assessed. RT plus ALDH$^{high}$ CSC-DC vaccine significantly inhibited the lung metastasis compared with PBS, RT alone or RT plus ALDH$^{low}$-DC treatment (P<0.05, FIG. 17A). Ten out of total 11 mice in PBS treated group, 9 mice in RT alone treated group and 8 mice in RT plus ALDH$^{low}$-DC vaccinated group developed lung metastasis (FIG. 17B). However, only 2 out of 11 mice in the RT plus CSC-DC vaccinated group developed lung metastasis (FIG. 17B). The representative histopathological graphs of the lung metastasis were shown in FIG. 17C. Massive tumor lesions were observed in the lungs harvested from PBS or RT alone treated hosts. Mice subjected to RT plus ALDH$^{low}$-DC treatment also showed multiple tumor lesions in the lungs. However, no tumor lesion was found in the RT plus ALDH$^{high}$ CSC-DC vaccinated group.

These results indicated that CSC-DC vaccination significantly inhibited the induction of lung metastases in both the micrometastatic and established disease settings. This was associated with significantly prolonged survival after the administration of CSC-DC vaccine (FIGS. 14B and 15B).

Figure 18:
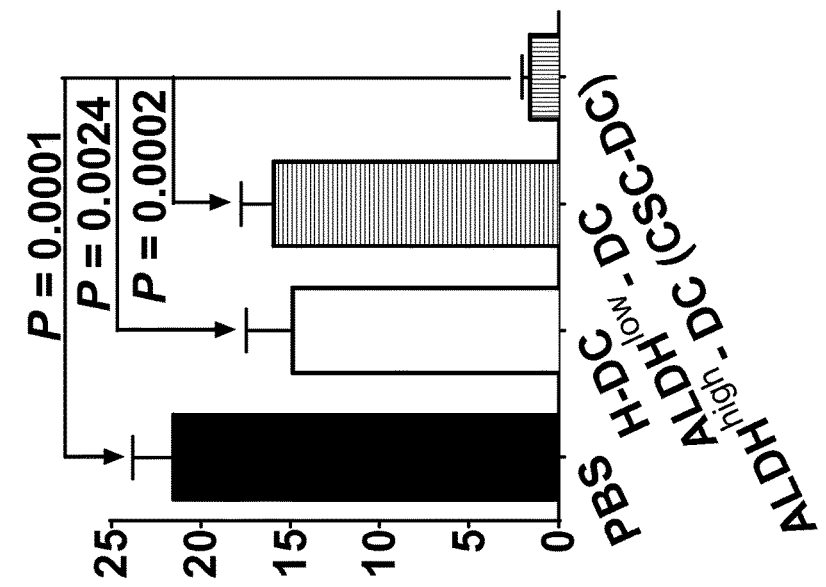
FIG. 18 shows CSC-DC vaccination significantly decreased the expression of CCR10 and CCR7 on D5 cells in the micrometastatic setting. The expression levels of the chemokine receptors in the freshly harvested s.c tumors were detected using flow cytometry.
Figure 18:
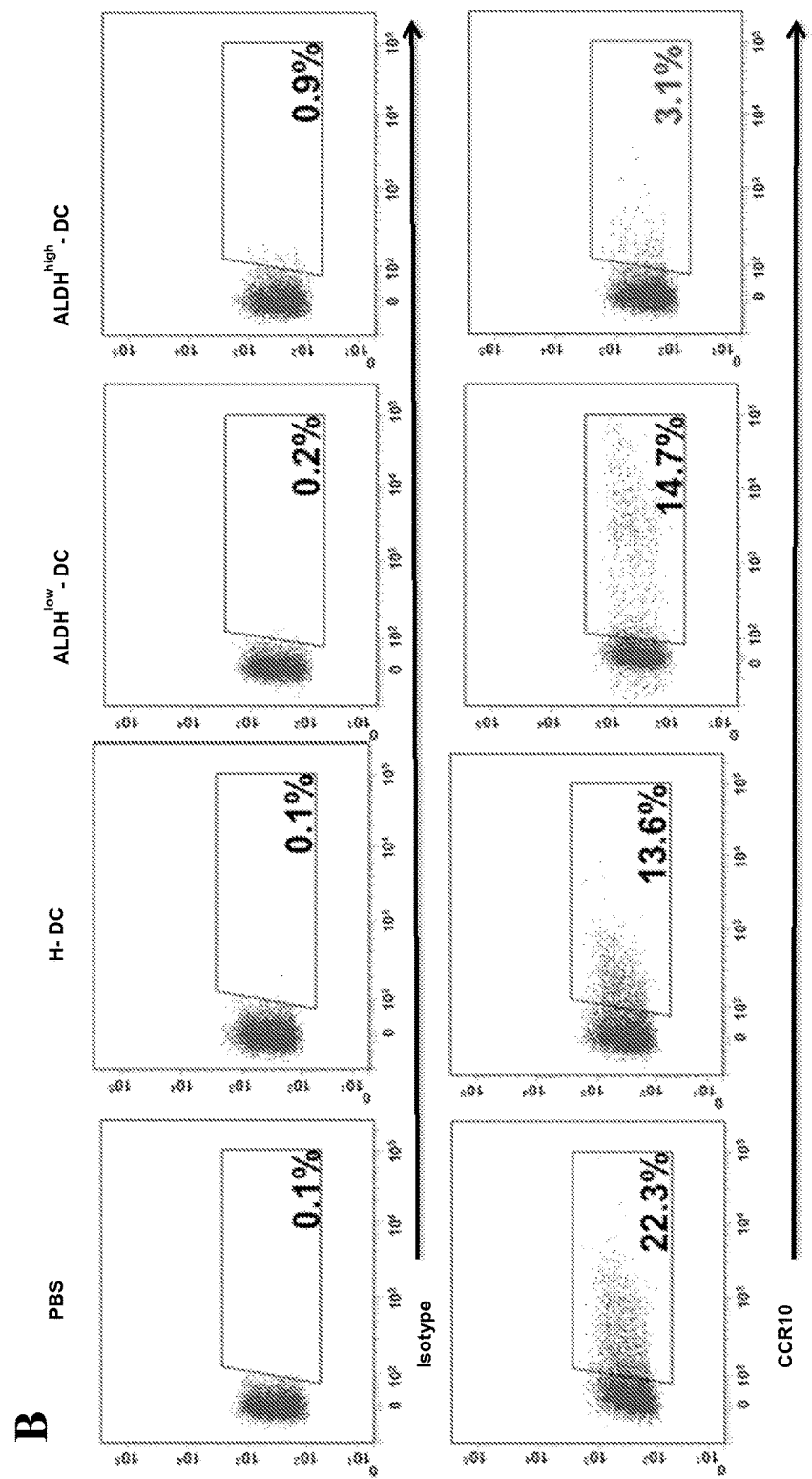
Figure 18:
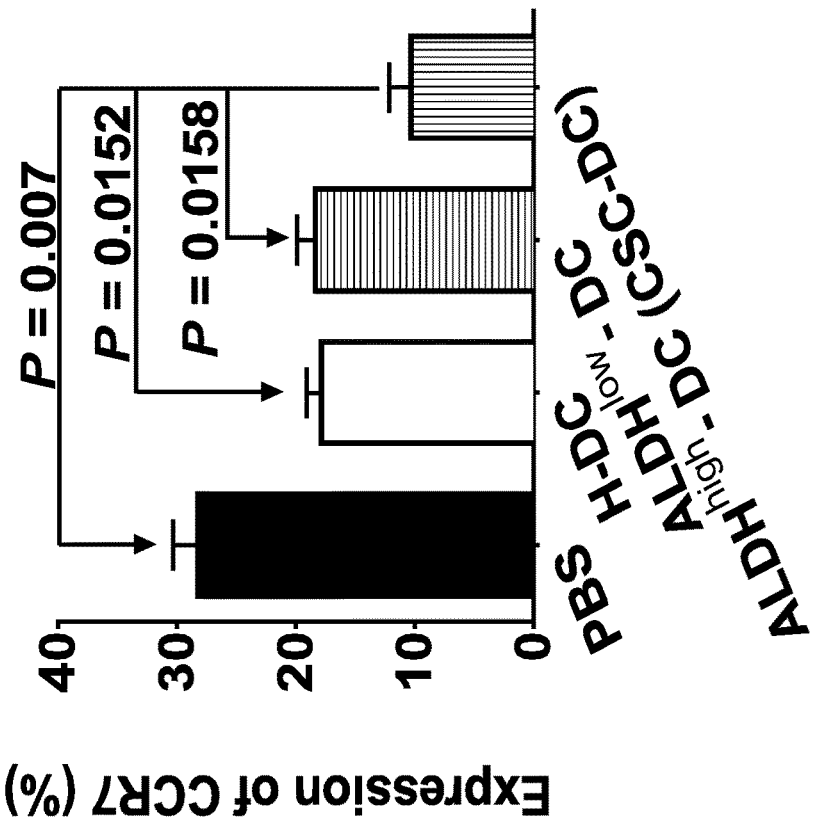
Figure 18:
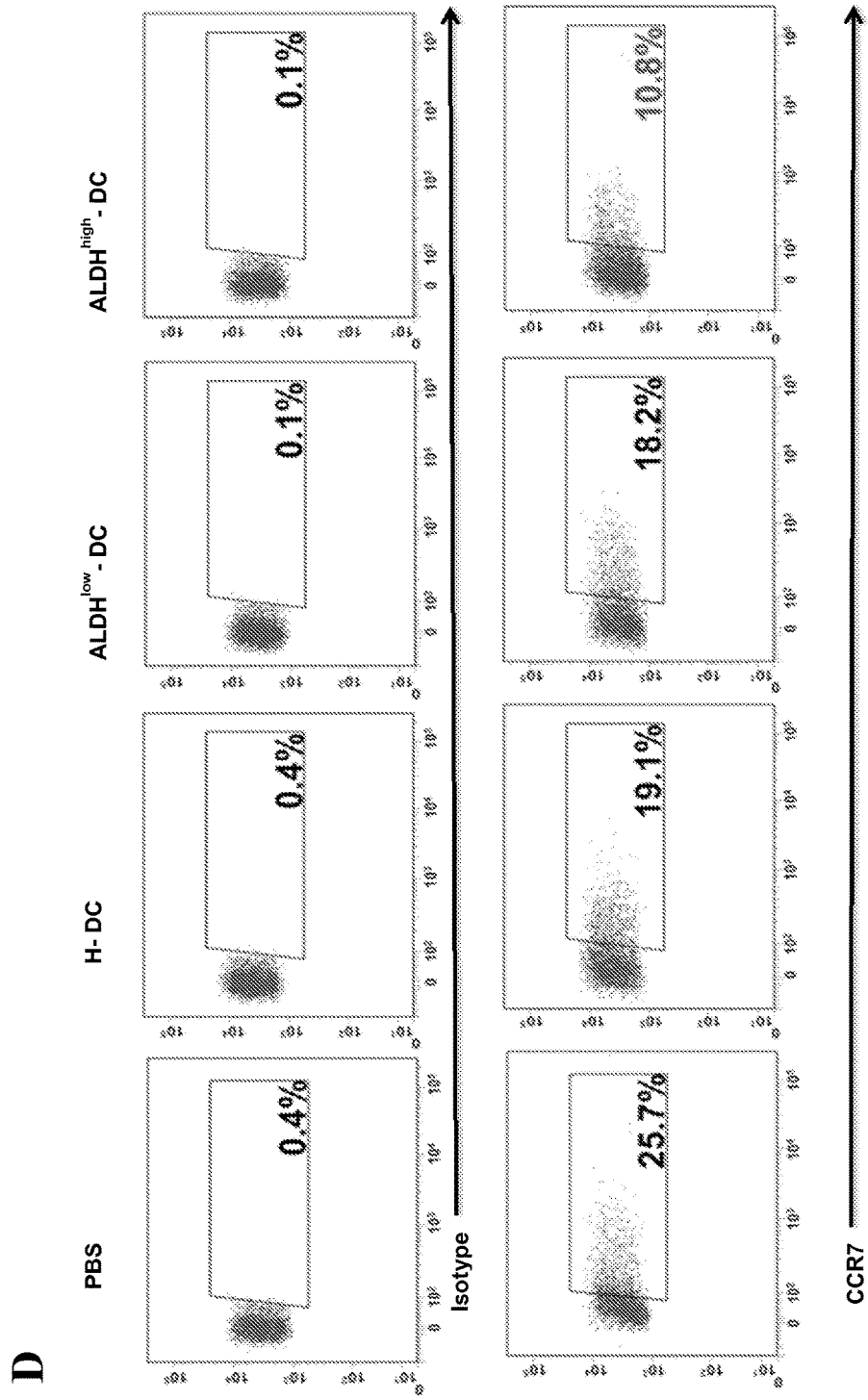

Tumor metastasis involves chemoattraction (61-63). To understand how CSC-DC vaccinations resulted in the inhibition of tumor metastasis, the expression of several chemokine receptors and their corresponding ligands were examined. To this end, subcutaneous D5 tumors growing in the micrometastatic disease model were harvested and digested into single tumor cell suspensions which were then detected for chemokine receptor expression by flow cytometry. In FIG. 18A, significantly decreased expression of CCR10 after CSC-DC vaccination was observed. With CSC-DC vaccination, the expression of CCR10 on D5 tumor cells was significantly decreased to about 3% compared with the PBS treatment (>22%), or with H-DC and ALDH$^{low}$-DC vaccination (both around 15%) (FIG. 18B). It was also observed that CSC-DC vaccination significantly reduced the expression of another chemokine receptor CCR7 (FIG. 18C, P<0.02 vs. all other groups). While H-DC and ALDH$^{low}$-DC treatments showed marginal effects on inhibiting the expression of CCR7 compared with the PBS treatment control, CSC-DC vaccination significantly decreased the CCR7 expression from >25% to approximately 10% (FIG. 18D).

Figure 19:
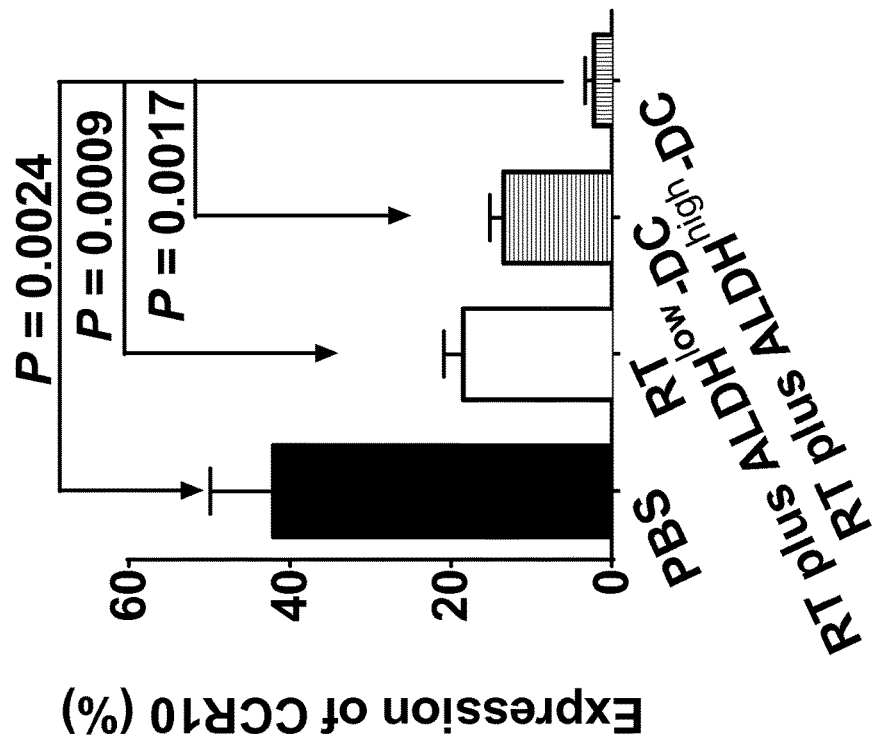
FIG. 19 shows RT plus CSC-DC vaccination significantly decreased the expression of CCR10 and CCR7 on D5 cells in the established tumor setting. The expression of the chemokine receptors in the freshly harvested s.c tumors were detected using flow cytometry.
Figure 19:
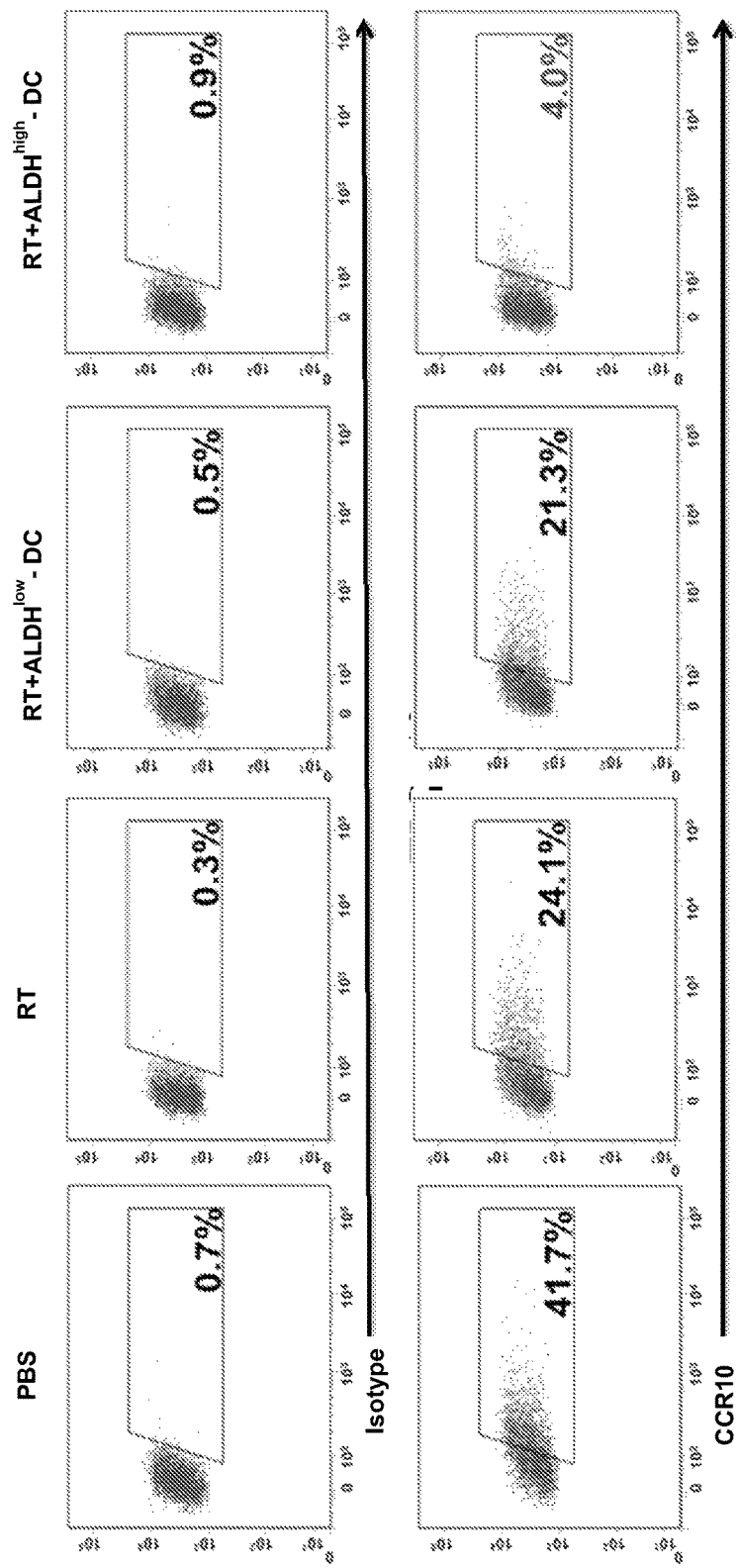
Figure 19:
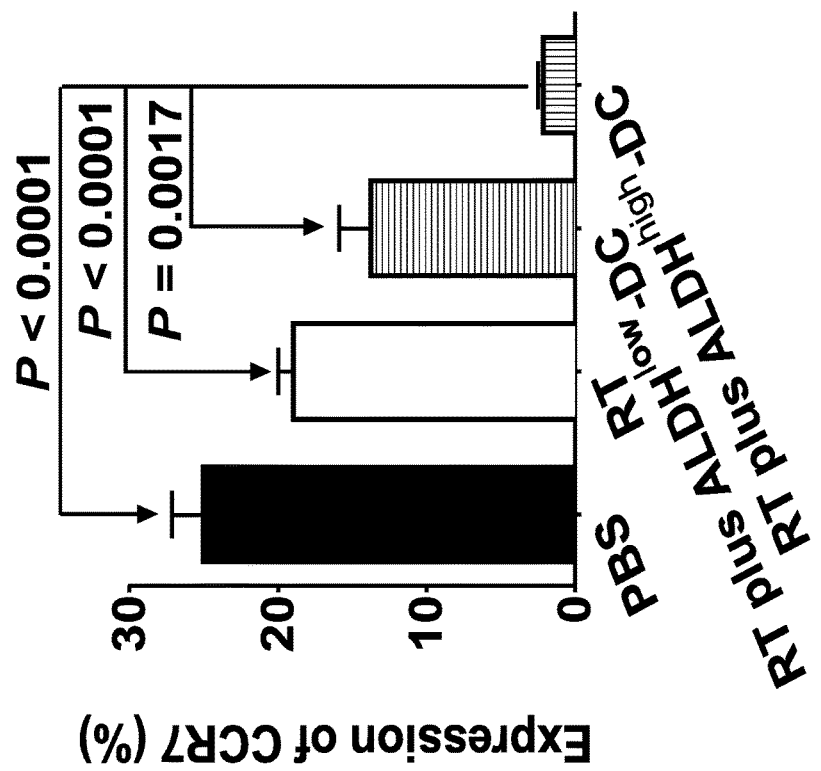
Figure 19:
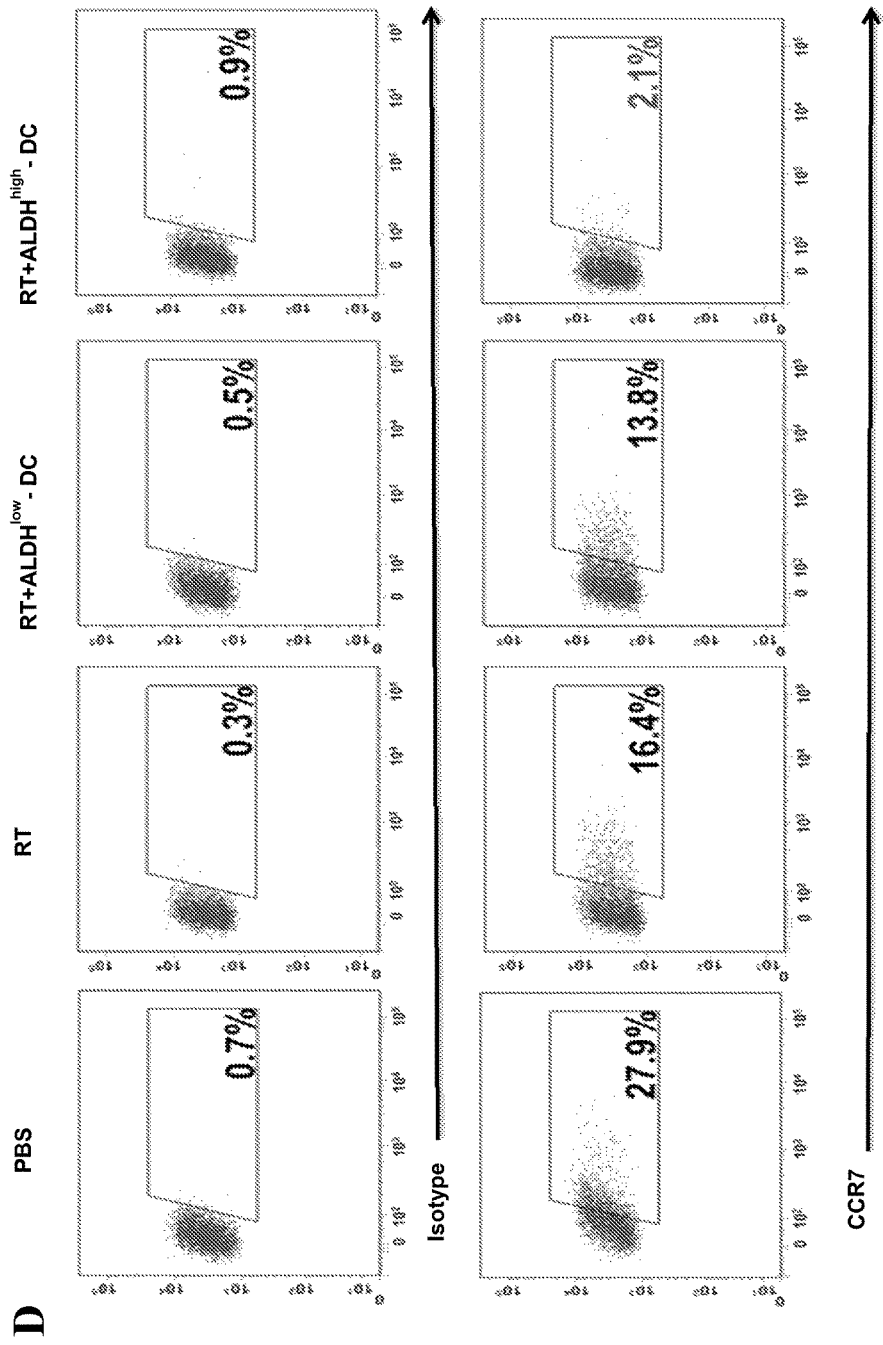

In the established D5 melanoma model, it was observed that RT plus CSC-DC vaccination significantly reduced the expression of CCR10 (P<0.01 vs. all other groups, FIG. 19A). As shown in FIG. 19B, RT alone treatment (24.1%) or RT plus ALDH$^{low}$-DC vaccine (21.3%) moderately decreased the expression of CCR10 on D5 tumor cells compared with the PBS control (41.7%). However, RT plus ALDH$^{high}$ CSC-DC vaccine significantly reduced the expression of CCR10 on D5 tumor cells to 4%. It was also observed significantly decreased expression of CCR7 after RT plus CSC-DC vaccination (P<0.01 vs. all other groups, FIG. 19C). After PBS, RT alone or RT plus ALDH$^{low}$-DC vaccination, the expression of CCR7 were 27.9%, 16.4% and 13.8% respectively. RT plus CSC-DC vaccination significantly reduced the expression of CCR7 on D5 tumor cells to 2.1% (FIG. 19D).

At the same time, qRT-PCR was carried out to detect the expressions of corresponding chemokines in the lung tissues. In the micrometastatic disease model (FIG. 20A-C), there was no significant difference in the expression of CCL21 (the ligand for CCR7) (FIG. 20A) between CSC-DC vaccinated group and all other groups. However, the expression of CCR10 corresponding chemokine CCL27 (FIG. 20B) and CCL28 (FIG. 20C) were both significantly decreased after ALDH$^{high}$ CSC-DC vaccine treatment (P<0.01 vs. all other groups). In the established D5 melanoma model (FIG. 20D-F), RT plus CSC-DC vaccine significantly (P<0.02 vs. all other groups) down-regulated the expressions of CCL21 (FIG. 20D), CCL27 (FIG. 20E) and CCL28 (FIG. 20F) in the lung tissues harvested from the tumor-bearing mice.

These data suggest that CSC-DC vaccination inhibits pulmonary metastasis of the local tumor by significantly down-regulating the expression of CCR7 and CCR10 on local tumor cells and by reducing the production of their ligands, e.g. CCL27 and CCL28 in the lung tissues.

4. CSC-DC Vaccine Treatment Reduces the Percentage of ALDH$^{high}$ Cells in the Primary Tumors To provide direct evidence that CSC-DC vaccine can induce anti-CSC immunity targeting CSCs, the ALDH$^{high}$ cell enriched population was examined in the s.c tumors freshly harvested from mice subjected to the CSC-DC treatment, either by itself in the treatment of micrometastatic D5 model or in combination with RT in the treatment of established D5 model. The identification of the ALDH$^{high}$ population was performed by flow cytometry as previously described (31). Tumor cells incubated with ALDEFLUOR plus the ALDH inhibitor DEAB were used as control to set the gate. ALDEFLUOR assays were done using multiple mice from each group, and the results were displayed with SE (FIG. 21A). In addition, the tumor cells from multiple mice of each experimental group were mixed, and generated representative flow cytometric graphs to demonstrate the identification of the ALDH$^{high}$ populations in each group (FIG. 21B). As shown in FIG. 21A in the micrometastatic D5 model, CSC-DC vaccination significantly reduced the percentage of ALDH$^{high}$ populations compared with PBS, H-DC, or ALDH$^{low}$-DC treatment (P=0.0002, P=0.0002 and P=0.0029, respectively). Primary s.c. tumor harvested from CSC-DC treated mice were found to contain only 1.7% ALDH$^{high}$ cells, which was significantly less than that present in the primary s.c. tumors of PBS-treated mice (13.4%), H-DC-vaccinated mice (7.5%) or ALDH$^{low}$-DC vaccinated hosts (8.3%) respectively (FIG. 21B).

In the established D5 model, radiation therapy (RT) increased the percentage of ALDH$^{high}$ cells in the treated residual primary tumors (FIG. 21C, D). Nevertheless, RT plus CSC-DC vaccination significantly reduced the percentage of ALDH$^{high}$ populations compared with PBS, RT alone, or RT plus ALDH$^{low}$-DC vaccination (P=0.0018, P=0.0018 and P=0.0096, respectively) (FIG. 21C). Specifically, primary s.c. tumors harvested from RT plus CSC-DC vaccinated mice were found to contain significantly less (<3%) of the ALDH$^{high}$ cells, compared with that present in the primary s.c. tumors of PBS-treated mice (14.2%), RT alone treated mice (20.5%) or RT plus ALDH$^{low}$-DC vaccinated hosts (12.8%) respectively (FIG. 21D).

5. CSC-DC Vaccine Treatment Modulates Host Humoral Responses which Specifically Targets CSCs As demonstrated above, CSC-DC vaccine used either alone or in combination with RT to respectively treat micrometastatic and established tumors has elicited effective antitumor immunity against local tumor growth, distant metastasis, and significantly prolonged the overall survival of the treated host. In parallel, it was found that CSC-DC vaccine significantly reduced the percentage of ALDH$^{high}$ cells in the primary s.c tumors. These results strongly suggest CSC-DC vaccine-induced CSC targeting.

CSC-DC vaccine-induced host humoral immune responses were evaluated against CSCs. Spleens were collected at the end of the treatment experiments. Purified splenic B cells were activated in vitro with LPS and anti-CD40, and the supernatants were collected. To test the specificity of CSC-DC vaccine-primed antibody production, the binding of the immune supernatants to the ALDH$^{high}$ D5 CSCs vs. ALDH$^{low}$ non-CSCs was tested. As shown in FIG. 22A, immune supernatants from mice which received CSC-DC treatment bound to ALDH$^{high}$ D5 CSCs (60.8%) much more effectively than the binding of immune supernatants collected from PBS-treated mice (12.3%); H-DC vaccinated mice (29.8%) or ALDH$^{low}$-DC treated hosts (15.7%). In contrast, the immune supernatants harvested from H-DC or ALDH$^{low}$-DC vaccinated mice bound to the ALDH$^{low}$ non-CSCs (45.8% and 50.2% respectively) significantly more than the binding of immune supernatants harvested from the CSC-DC vaccinated mice (6.8%) or from PBS-treated control (18.8%). FIG. 22B shows the results of multiple binding assays, indicating that the immune supernatants produced by CSC-DC vaccine-primed B cells bound to the ALDH$^{high}$ D5 CSCs much more effectively than supernatants collected from all the control groups (P<0.01 vs. all other groups). In contrast, the ALDH$^{low}$-DC vaccine-primed immune supernatants bound to the ALDH$^{low}$ non-CSCs similar to the binding by H-DC vaccine-primed immune supernatants, but significantly more than the bindings by PBS or CSC-DC vaccine-primed immune supernatants (FIG. 22C).

In the established D5 model (FIG. 23A), the binding to ALDH$^{high}$ D5 CSCs was significantly higher by RT plus ALDH$^{high}$ CSC-DC vaccine-primed immune supernatant (76.6%) compared with the supernatants collected from PBS-treated group (17.5%), RT alone treated hosts (21.4%) or RT plus ALDH$^{low}$-DC vaccinated mice (25.1%). In contrast, for the binding to ALDH$^{low}$ D5 cells, the immune supernatants from RT plus ALDH$^{low}$-DC vaccine treated mice (69.8%) were much more effective than the supernatants harvested from RT-treated mice (21%) or the RT plus ALDH$^{high}$-DC vaccine-primed immune supernatant (23.8%). Repeated experiments showed that RT+ALDH$^{high}$ D5 CSC-DC vaccine-primed immune supernatants bound to the ALDH$^{high}$ D5 CSCs significantly more than ALDH$^{low}$-DC vaccine-primed immune supernatant in the same setting of local tumor irradiation (P=0.0008, FIG. 23B). In contrast, the ALDH$^{low}$-DC vaccine-primed immune supernatant bound to the ALDH$^{low}$ D5 cells much more than the CSC-DC vaccine-primed immune supernatant (P=0.0004, FIG. 23C).

To evaluate the immunologic consequence of the binding of CSC-DC vaccine-primed antibody to CSCs, antibody and complement-dependent cytotoxicity (CDC) assays were performed. FIG. 24A shows the results from the micrometastatic D5 model. ALDH$^{high}$ CSC-DC vaccine-primed immune supernatant killed ALDH$^{high}$ D5 CSCs significantly more than the immune supernatants collected from other groups (P<0.001 vs. all other groups). In contrast, the immune supernatant harvested from H-DC or ALDH$^{low}$ non-CSC vaccinate-treated host resulted in significant ALDH$^{low}$ D5 cell lysis, while the immune supernatant from the ALDH$^{high}$ CSC-DC vaccinated hosts showed minimal lysis of the ALDH$^{low}$ targets (FIG. 24A). Similar results were obtained from the established D5 model (FIG. 24B). While the immune supernatants generated from the mice subjected to RT plus ALDH$^{high}$ CSC-DC vaccine mediated significantly more efficient ALDH$^{high}$ D5 CSC lysis (P<0.0001 vs. all other groups), RT alone or RT plus ALDH$^{low}$-DC vaccine-primed immune supernatants showed little lysis of ALDH$^{high}$ D5 CSCs. In contrast, RT plus ALDH$^{high}$ CSC-DC vaccinated immune supernatant killed significantly less ALDH$^{low}$ D5 cells than RT plus ALDH$^{low}$-DC vaccine-primed immune supernatant (FIG. 24B, P<0.0001). Together these data indicate that ALDH$^{high}$ D5 CSC-DC vaccine, used either by itself or in combination with RT to treat the micrometastatic and established cancer respectively, could confer significant host anti-CSC immunity.

Traditional DC vaccines target tumors that express differentiated tumor antigens. However, due to the heterogeneous characters of the tumor mass, CSCs that do not express these differentiated tumor antigens may escape the immunological targeting. Although tumor burden often decreases after conventional therapy, tumors recur. This is largely due to the residual CSCs resistant to these therapies. The first treatment model discussed above was designed to treat the micrometastatic disease to examine the benefit of using CSC-DC vaccine in preventing local tumor growth, lung metastasis, and prolonging the animal survival. While the traditional H-DC vaccination and the control ALDH$^{low}$-DC slightly inhibited the local tumor growth and moderately prolonged survival, the ALDH$^{high}$ CSC-DC vaccine revealed significantly more effective antitumor immunity by inhibiting the local tumor growth and prolonging the survival of the tumor-bearing mice. This was true in both the D5 and SCC7 tumor models tested.

Several studies have demonstrated that CSCs are relatively resistant to chemotherapy (8, 1-17, 64) and radiation (65-67) in contrast to non-CSC tumor cells. One may find minimal difference between the therapeutic efficacies of CSC-DC vs. other treatment judged by tumor size in established disease because the composition of the tumor cells within established subcutaneous tumor nodule harbor only a small fraction of CSCs. Hence, the therapeutic efficacy of CSC-DC was evaluated in the setting of local tumor irradiation. The initial therapy of established tumors with local radiation may result in destruction of non-CSC tumor cells with an increase in the percentage of CSCs. It is in this setting that subsequent CSC-DC vaccination may be therapeutic by selectively targeting the CSCs in the residual tumors. Hence, ALDH$^{high}$ CSC lysate-pulsed DC vaccine was used as an additional strategy to radiation therapy of established tumors in this example. It was found that RT plus melanoma D5 ALDH$^{high}$-DC (CSC-DC) significantly inhibited local tumor growth, lung metastasis and prolonged animal survival. These observations were confirmed in a 2$^{nd}$ model, the squamous cell cancer SCC7. Word was then focused on the D5 model to investigate the potential mechanisms which may be involved in the induction of anti-CSC immunity by CSC-DC vaccine used either by itself or in combination with RT to treat the micrometastatic and established D5 respectively.

In this example, the therapeutic efficacy of CSC-DC vaccine was associated with significantly inhibited spontaneous metastasis to the lung. Cancer metastasis is a complex process and involves many factors, among which chemoattraction is considered to play a critical role in determining the organ selectivity. Many studies report that the preferred sites of tumor cell metastasis were determined by the expression levels of chemokine in the target organs, as well as the expression of corresponding chemokine receptors on the malignant tumor cells. For example, B16 cells that overexpress CCR10 were resistant to host immune responses and led to tumor progression (75). Wiley et al. suggested that CCR7-expression B16 cells had increased metastasis to draining lymph nodes (77). In this example, the subcutaneous primary D5 tumor cells harvested from non-treated mice expressed high levels of CCR7 and CCR10 (20-40%). CSC vaccination significantly reduced the expression of these two receptors to 2-10% in the micrometastatic as well as in the established D5 models. On the other hand, the mRNA levels of CCL27 and CCL28 (ligands for CCR10) decreased significantly in the lung tissues harvested from the animals subjected to CSC-DC vaccine both in the mirometastatic and in established D5 models. In addition, CSC-DC vaccine also decreased the expression of CCL21 (ligands of CCR7) in the setting of RT in the established D5 model. While not necessary to understand or practice the present invention, it may be that the expression of chemokine or chemokine receptors may lead to immune tolerance or immune escape, which in turn result in tumor progression (76, 78, 79). Our data suggest that decreased interaction between CCR10/CCL27 and CCL28 and CCR7/CCL21 plays an important role in CSC-DC vaccination-induced prevention of tumor metastasis.

Zhao et al recently found that CCR7/NF-kappaB autocrine signaling loop in CCR7-positive head and neck squamous cell carcinoma involves PKCα (80). Takekoshi et al. recently compared CCR7-expressing B16 melanoma cells (pLNCX2-B16) and CCR7-overexpressing B16 cells (CCR7-B16), and found that LN metastasis was dramatically enhanced in CCR7-B16 tumors (81). Microarray analysis of leukocyte-depleted pLNCX2-B16 and CCR7-B16 tumor cell suspensions showed that several genes linked to interferon IFNγ signaling pathways, e.g. STAT1, CXCR 9-11, CCL5 and CXCL10, MHC I and MHC II, were downregulated in the CCR7-B16 tumor microenvironment, suggesting activation through CCR7 can downregulate pathways critical for host anti-tumor immunity (81). Wicha and colleagues reported that blockade of the IL-8 receptor CXCR1 using either a CXCR1-specific blocking antibody or repertaxin, a small-molecule CXCR1 inhibitor, selectively depleted the CSC population, and the effects of CXCR1 blockade on CSC viability via FASL/FAS signaling were mediated by the FAK/AKT/FOXO3A pathway (28). In general, chemokine receptors can activate downstream effectors, such as mitogen-activated protein kinases, by complex mechanisms of ligand-dependent activation of cryptic growth factors; guanosine triphosphate-binding, protein-coupled activation of survival kinases; or transactivation of other receptors such as ErbB family members (82). The molecular and biochemical signaling pathways in cancer stem cell-DC vaccine-induced down-regulation of CCR10/CCL27 and CCL28 and CCR7/CCL21 interactions in this study remain to be identified. Blockade of these chemokine/chemokine receptor interactions (e.g., with anti-CCL27, anti-CCR10, anti-CCL28, anti-CCR7 and/or anti-CCL21 monoclonal antibodies) may result in retarded primary s.c tumor metastasis to the lung and therefore improve survival.

CSCs are found to be responsible for tumor metastasis and progression (54, 83-85). To examine whether CSCs are actually targeted by CSC-induced immunity, it was measured whether CSCs survive the therapeutic maneuver. Specifically, the number of residual CSCs was checked to see if the percentage of CSCs changes after CSC-DC immunotherapy. It was found in the micrometastatic D5 model that ALDH$^{high}$ CSC populations (<2%) in the residual primary s.c tumor of the mice subjected to CSC-DC vaccine was remarkably decreased compared with the PBS-treated control (~15%), and was significantly lower than those of the animals subjected to H-DC or ALDH$^{low}$-DC treatment (7-9%). In the established D5 model, while it was found that RT treatment increased the CSCs in the primary s.c. tumor compared with non-treated control, the percentage of ALDH$^{high}$ CSCs decreased significantly after RT plus CSC-DC vaccination from control (~15%) to <3%, which was significantly less than those after treatment with RT alone (~20%) or with RT plus ALDH$^{low}$ DC vaccination (~12%). These results indicate that CSC-DC vaccine could induce direct targeting of CSCs, either by itself or in the setting of local tumor irradiation.

In certain embodiments, CSC-DC vaccine in combination with conventional therapies may provide a more effective treatment approach for cancer patients. For example, the administration of CSC vaccines after surgical excision of tumor where local relapse and death is high, or administration of CSC vaccine following neoadjuvant chemoradiation or radiotherapy and surgery may reduce local tumor relapse and distant metastasis.

REFERENCES (LIST 1)

1. Chang et al., J Clin Oncol 2003; 21:884-90.
2. Chang et al., Hum Gene Ther 2000; 11:839-50.
3. Prieto et al., J Immunother 2010; 33:547-56.
4. Redman et al., J Immunother 2008; 31:591-8.
5. Chang A E, Clin Cancer Res 2002; 8:1021-32.
6. Dannull et al., J Clin Invest 2005; 115:3623-33.
7. Al Hajj et al. Proc Natl Acad Sci USA 2003; 100:3983-8.
8. Collin et al., Cancer Res 2005; 65:10946-51.
9. Hemmati et al., Proc Natl Acad Sci USA 2003; 100: 15178-83.
10. Singh et al., Cancer Res 2003; 63:5821-8.
11. Ho et al., Cancer Res 2007; 67:4827-33.
12. Patrawala et al., Cancer Res 2007; 67:6796-805.
13. Li et al., Cancer Res 2007; 67:1030-7.
14. Hop et al., Nat Immunol 2004; 5:738-43.
15. Ricci-Vitiani et al., Nature 2007; 445:111-5.
16. Prince et al., Proc Natl Acad Sci USA 2007; 104:973-8.
17. Schatton et al., Nature 2008; 451:345-9.
18. Shafee et al., Cancer Res 2008; 68:3243-50.
19. Nandi et al., Cancer Res 2008; 68:5778-84.
20. Naka et al., Nature 2010; 463:676-80.
21. Zhao et al., Nature 2009; 458:776-9.
22. Dallas et al., Cancer Res 2009; 69:1951-7.
23. Yamauchi et al., Cancer Res 2008; 68:516-20.
24. Visus et al., Clin Cancer Res 2011; 17:6174-84.
25. Shackleton et al., Nature 2006; 439:84-8.
26. Arca et al., Cancer Gene Ther 1996; 3:39-47.
27. Ito et al., Cancer Res 2004; 64:8411-9.
28. Li et al., J Immunol 2009; 183:3195-203.
29. Moyer et al., J Immunother 2008; 31:885-95.
30. Ginestier et al., Cell Stem Cell 2007; 1:555-67.
31. Carpentino et al., Cancer Res 2009; 69:8208-15.
32. van den Hoogen et al., Cancer Res 2010; 70:5163-73.
33. Carafe-Jauffret et al., Cancer Res 2009; 69:1302-131.
34. Ginestier et al., J Clin Invest 2010; 120:485-97.
35. Kirk et al., Cancer Res 2001; 61:2062-70.
36. Clay et al., Head Neck 2010; 32:1195-201.
37. Quintana et al., Nature 2008; 456:593-8.
38. Civenni et al., Cancer Res 2011; 71:3098-109.
39. Jacob et al., J Immunol 2009; 182:5873-81.
40. Li et al., Cancer Res 2005; 65:1063-70.
41. Kjaergaard et al., J Neurosurg 2005; 103:156-64.
42. Castriconi et al., J Immunol 2009; 182:3530-9.
43. Contag et al., Cancer Res 2010; 70:9837-45.
44. Todaro et al., J Immunol 2009; 182:7287-96.
45. Pellegatta et al., Cancer Res 2006; 66:10247-52.
46. Xu et al., Stem Cells 2009; 27:1734-40.
47. Boiko et al., Nature 2010; 466:133-7.
48. Schatton et al., Cancer Res 2010; 70:697-708.

REFERENCES (LIST 2)

1. Chang et al., J Clin Oncol. 2003; 21(5):884-890.
2. Chang et al., Clin Cancer Res. 2002; 8(4):1021-1032.
3. Dougan and Dranoff, Annu Rev Immunol. 2009; 27 (83-117.
4. Oldham, J Cell Physiol Suppl. 1986; 4 (91-99.
5. Redman et al., J Immunother. 2008; 31(6):591-598.
6. Kalbasi et al., J Clin Invest. 2013; 123(7):2756-2763.
7. Nandi et al., Cancer Res. 2008; 68(14):5778-5784.
8. Shafee et al., Cancer Res. 2008; 68(9):3243-3250.
9. Laga and Murphy, Arch Pathol Lab Med. 2010; 134(12): 1750-1757.
10. Valent et al., Cancer Res. 2013; 73(3):1037-1045.
11. Asselin-Labat et al., J Natl Cancer I. 2006; 98(14):1011-1014.
12. Wicha et al., Cancer Res. 2006; 66(4):1883-1890.
13. Medema et al., Nat Cell Biol. 2013; 15(4):338-344.
14. Dallas et al., Cancer Res. 2009; 69(5):1951-1957.
15. Naka et al., Nature. 2010; 463(7281):676-U111.
16. Zhao et al., Nature. 2009; 458(7239):776-U117.
17. Yamauchi et al., Cancer Res. 2008; 68(2):516-520.
18. Brown et al., Cancer Res. 2009; 69(23):8886-8893.
19. Jachetti et al., Oncoimmunology. 2013; 2(5):16.
20. Liao et al., J Cancer Res Clin Oncol. 2013; 139(1):159-170.
21. Visus et al., Clin Cancer Res. 2011; 17(19):6174-6184.
22. Castriconi et al., J Immunol. 2009; 182(6):3530-3539.
23. Contag et al., Cancer Res. 2010; 70(23):9837-9845.
24. Tallerico et al., J Immunol. 2013; 190(5):2381-2390.
25. Todaro et al., J Immunol. 2009; 182(11):7287-7296.
26. Bach et al., Cancer Res. 2013; 73(2):865-874.
27. Skubitz et al., Gynecol Oncol. 2013; 130(3):579-587.
28. Ginestier et al., J Clin Invest. 2010; 120(2):485-497.
29. Clay et al., Head Neck-J Sci Spec. 2010; 32(9):1195-1201.
30. Ginestier et al., Cell Stem Cell. 2007; 1(5):555-567.
31. Ning et al., Cancer Res. 2012; 72(7):1853-1864.
32. Yasuda et al., PLoS One. 2013; 8 (8).
33. Almanaa et al., J Cancer. 2013; 4(7):536-548.
34. Awad et al., PLoS One. 2010; 5 (11).
35. Boonyaratanakornkit et al., J Invest Dermatol. 2010; 130(12):2799-2808.
36. Carpentino et al., Cancer Res. 2009; 69(20):8208-8215.
37. Charafe-Jauffret et al., Clinical Cancer Research. 2010; 16(1):45-55.
38. Charafe-Jauffret et al., Cancer Res. 2009; 69(4):1302-1313.
39. Deng et al., PLoS One. 2010; 5 (4).
40. Huang et al., Cancer Res. 2009; 69(8):3382-3389.
41. Januchowski et al., Biomed Pharmacother. 2013.
42. Le Magnen et al., Clin Cancer Res. 2013; 19(19):5361-5371.
43. Luo et al., Cancer Res. 2009; 69(2):466-474.
44. Matsui et al., Blood. 2004; 103(6):2332-2336.
45. Pearce et al., Stem Cells. 2005; 23(6):752-760.
46. Stecca et al., Curr Protoc Stem Cell Biol. 2013; Chapter 3 (Unit 36).
47. van den Hoogen et al., Cancer Res. 2010; 70(12):5163-5173.
48. Prince et al., P Natl Acad Sci USA. 2007; 104(3):973-978.
49. Ito et al., Cancer Res. 2004; 64(22):8411-8419.
50. Tanigawa et al., J Immunother. 2001; 24(6):493-501.
51. Tupchong et al., Int J Radiat Oncol. 1991; 20(1):21-28.

52. Vokes et al., N Engl J Med. 1993; 328(3):184-194.
53. Yu et al., Front Biosci. 2012; 4 (1528-1541.
54. Geiger and Peeper, et al., Biochim Biophys Acta. 2009; 1796(2):293-308.
55. Mina and Sledge, Nat Rev Clin Oncol. 2011; 8(6):325-332.
56. Leung et al., Cancer J. 2012; 18(2):176-184.
57. Agarwala et al., Am J Clin Dermatol. 2003; 4(5):333-346.
58. Schrader, Anticancer Drugs. 2000; 11(3):143-148.
59. de Bree et al., Oral Oncol. 2012; 48(9):780-786.
60. Yi et al., J Surg Oncol. 2012; 106(6):708-712.
61. Ben-Baruch et al., Clin Exp Metastas. 2008; 25(4):345-356.
62. Muller et al., Nature. 2001; 410(6824):50-56.
63. Payne and Cornelius, J Invest Dermatol. 2002; 118(6):915-922.
64. Li et al., J Natl Cancer I. 2008; 100(9):672-679.
65. Bao et al., Nature. 2006; 444(7120):756-760.
66. Bertrand et al., Stem Cell Rev. 2013.
67. Phillips et al., J Natl Cancer I. 2006; 98(24):1777-1785.
68. Duarte et al., Stem Cells. 2013; 31(3):423-432.
69. Garcia-Hernandez et al., Cancer Res. 2008; 68(3):861-869.
70. Pellegatta et al., Cancer Res. 2006; 66(21):10247-10252.
71. Xu et al., Stem Cells. 2009; 27(8):1734-1740.
72. Ben-Baruch et al., Cell Adhes Migr. 2009; 3(4):328-333.
73. Dobner et al., Acta Ophthalmol. 2012; 90 (8):e638-e644.
74. Murakami et al., J Dermatol Sci. 2004; 36(2):71-78.
75. Kai et al., Pathol Res Pract. 2011; 207(1):43-48.
76. Simonetti et al., Eur J Cancer. 2006; 42(8):1181-1187.
77. Wiley et al., J Natl Cancer I. 2001; 93(21):1638-1643.
78. Murakami et al., J Exp Med. 2003; 198(9):1337-1347.
79. Pivarcsi et al., P Natl Acad Sci USA. 2007; 104(48):19055-19060.
80. Zhen-jin et al., Mol Cell Biochem. 2011; 357 (1-2):181-187.
81. Takekoshi et al., Oncogenesis. 2012; 7(1):9.
82. Salazar et al., Crit Rev Eukaryot Gene Expr. 2013; 23(1):77-91.
83. Chen et al., Acta Pharmacol Sin. 2013; 34(6):732-740.
84. Enderling et al. Front Oncol. 2013; 3(76):00076.
85. Schatton and Frank, Pigm Cell Melanoma R. 2008; 21(1):39-55.
86. Teitz-Tennenbaum et al., Cancer Res. 2003; 63(23):8466-8475.
87. Wang et al., PLoS One. 2011; 6(9):26.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:
1. A system comprising:
 a) $ALDH^{high}$-DCs ($ALDH^{high}$-Dendritic Cells), and
 b) a radioactive implant configured for use in internal radiation cancer therapy.
2. A system comprising:
 a) $ALDH^{high}$-DCs ($ALDH^{high}$-Dendritic Cells), and
 b) a device configured to emit radiation used during external radiation cancer therapy.
3. A composition comprising: $ALDH^{high}$-DCs ($ALDH^{high}$-Dendritic Cells) and radionucleotides.

* * * * *

UNITED STATES PATENT AND TRADEMARK OFFICE
CERTIFICATE OF CORRECTION

PATENT NO. : 10,173,074 B2
APPLICATION NO. : 14/437064
DATED : January 8, 2019
INVENTOR(S) : Qiao Li et al.

Page 1 of 1

It is certified that error appears in the above-identified patent and that said Letters Patent is hereby corrected as shown below:

In the Specification

Column 1, Lines 7-9 should read:
This invention was made with government support under grant number CA082529 awarded by the National Institutes of Health. The government has certain rights in the invention.

Signed and Sealed this
Twenty-fifth Day of June, 2019

Andrei Iancu
*Director of the United States Patent and Trademark Office*